United States Patent
Yong et al.

(10) Patent No.: US 12,168,690 B2
(45) Date of Patent: Dec. 17, 2024

(54) ANTI-EGFR/ANTI-4-1BB BISPECIFIC ANTIBODY

(71) Applicants: ABL Bio Inc., Seongnam-si (KR); YUHAN CORPORATION, Seoul (KR)

(72) Inventors: Yeryoung Yong, Seongnam-si (KR); Ui-Jung Jung, Seongnam-si (KR); Hyejin Chung, Seongnam-si (KR); Kyeongsu Park, Seongnam-si (KR); Wonjun Son, Seongnam-si (KR); Yangsoon Lee, Seongnam-si (KR); Yeunju Kim, Seongnam-si (KR); Eunsil Sung, Seongnam-si (KR); Youngkwang Kim, Seongnam-si (KR); Youngdon Pak, Seongnam-si (KR); Minji Park, Seongnam-si (KR); Jaehyun Eom, Seongnam-si (KR); Hyoju Choi, Seongnam-si (KR); Moo Young Song, Suwon-si (KR); Na Rae Lee, Seoul (KR); Young Bong Park, Yongin-si (KR); Eun-Jung Lee, Yongin-si (KR); Eun-Jung Lee, Yongin-si (KR)

(73) Assignees: ABL BIO INC., Seongnam-si (KR); YUHAN CORPORATION, Seoul (KR)

( * ) Notice: Subject to any disclaimer, the term of this patent is extended or adjusted under 35 U.S.C. 154(b) by 0 days.

(21) Appl. No.: 16/939,472

(22) Filed: Jul. 27, 2020

(65) Prior Publication Data
US 2021/0024638 A1  Jan. 28, 2021

Related U.S. Application Data

(60) Provisional application No. 62/878,977, filed on Jul. 26, 2019.

(51) Int. Cl.
*C07K 16/28* (2006.01)
*A61K 39/00* (2006.01)
*A61K 39/395* (2006.01)

(52) U.S. Cl.
CPC ...... *C07K 16/2863* (2013.01); *C07K 16/2878* (2013.01); *A61K 39/39541* (2013.01);
(Continued)

(58) Field of Classification Search
None
See application file for complete search history.

(56) References Cited

U.S. PATENT DOCUMENTS

| | | | |
|---|---|---|---|
| 5,928,893 A | 7/1999 | Kang et al. | |
| 10,280,230 B2 * | 5/2019 | Goletz | C07K 16/2863 |

(Continued)

FOREIGN PATENT DOCUMENTS

| | | |
|---|---|---|
| CN | 113166250 | 7/2021 |
| CN | 113166265 | 7/2021 |

(Continued)

OTHER PUBLICATIONS

Makkouk et al., Characterizing CD137 upregulation on NK cells in patients receiving monoclonal antibody therapy, Annals Oncol. 28:415-520, 2017.*

(Continued)

*Primary Examiner* — Claire Kaufman
(74) *Attorney, Agent, or Firm* — LEX IP MEISTER, PLLC

(57) ABSTRACT

Provided are an anti-4-1BB/anti-EGFR bispecific antibody, and a pharmaceutical composition and a method for treating and/or preventing a cancer using the same.

6 Claims, 21 Drawing Sheets
Specification includes a Sequence Listing.

(52) U.S. Cl.
CPC .... *A61K 2039/505* (2013.01); *C07K 2317/24* (2013.01); *C07K 2317/31* (2013.01); *C07K 2317/565* (2013.01); *C07K 2317/622* (2013.01); *C07K 2317/732* (2013.01); *C07K 2317/75* (2013.01); *C07K 2317/76* (2013.01)

(56) References Cited

U.S. PATENT DOCUMENTS

| | | | |
|---|---|---|---|
| 10,421,758 | B2 * | 9/2019 | Chiosis .................. G16C 20/60 |
| 10,919,977 | B2 * | 2/2021 | Gao .................... C07K 16/2863 |
| 2016/0152722 | A1 | 6/2016 | Sharp et al. |
| 2019/0169308 | A1 * | 6/2019 | Dahlén ............. A61K 39/39558 |
| 2022/0056136 | A1 * | 2/2022 | Park ................... C07K 16/2878 |

FOREIGN PATENT DOCUMENTS

| | | |
|---|---|---|
| RU | 2610688 | 2/2017 |
| WO | 2017-059387 | 4/2017 |
| WO | 2017-173321 | 10/2017 |
| WO | 2018-190719 | 10/2018 |
| WO | 2019-016402 | 1/2019 |
| WO | 2019-129644 | 7/2019 |
| WO | 2020-102233 | 5/2020 |
| WO | 2020-107715 | 6/2020 |

OTHER PUBLICATIONS

Singh et al., Anti-claudin 18.2 antibody as new targeted therapy for advanced gastric cancer, J. Hematol. Oncol. 10:105, DOI 10.1186/s13045-017-0473-4, 2017.*

Clinicaltrials.gov, Study NCT03922204 v1, Retrieved from: <URL:https://clinicaltrials.gov/ct2/history/NCT03922204?A=1&B=1&C=merged#StudyPageTop>, [retrieved on Jun. 10, 2022], Apr. 18, 2019.*

Herold et al., Determinants of the assembly and function of antibody variable domains, Sci. Rep. 7:12276, DOI:10.1038/s41598-017-12519-9, Sep. 2017.*

Kranz et al., Restricted reassociation of heavy and light chains from hapten-specific monoclonal antibodies, Proc. Natl. Acad. Sci. USA, 78(9):5807-5811, Sep. 1981.*

Nezlin, RS, Biochemistry of Antibodies, Plenum Press:New York, p. 160, 1970.*

MacCallum et al.,Antibody-antigen interactions: contact analysis and binding site topography, J. Mol. Biol. 262:732-745, 1996.*

Chen et al., Enhancement and destruction of antibody function by somatic mutation: unequal occurrence is controlled by V gene combinatorial associations, EMBO J. 14(12):2784-2794, 1995.*

Lamminmaki et al., Chrystal structure of a recombinant anti-estradiol Fab fragment in complex with the 17beta-estradiol, J. Blol. Chem. 276:36687-94, 2001.*

Brinkmann et al., The making of bispecific antibodies, mAbs, 9:2:182-212, DOI: 10.1080/19420862.2016.1268307, 2017.*

Chester et al., Immunotherapy targeting 4-1BB: mechanistic rationale, clincial results, andfuture strategies, Blood, 131(1):49-57, 2018.*

KIPO, PCT Search Report & Written Opinion of PCT/KR2020/009870 dated Nov. 2, 2020.

Asano, Ryutaro, et al. "Structural considerations for functional anti-EGFR$^x$ anti-CD3 bispecific diabodies in light of domain order and binding affinity." Oncotarget 9.17 (Feb. 14, 2018): 13884-13893.

Sun Jian. "Cancer Immunotherapy Comes of Age." Progress in Pharmaceutical Sciences 39.12 (Dec. 2015): 921-935, with English Abstract.

EPO, Supplementary Partial European Search Report of the corresponding EP Patent Application No. 20848658.9 dated Jun. 16, 2023.

Compte, Marta, et al. "A tumor-targeted trimeric 4-1BB-agonistic antibody induces potent anti-tumor immunity without systemic toxicity." Nature communications 9.1 (Nov. 15, 2018): 4809.pp. 1-13.

Chen, Ching, et al. "Enhancement and destruction of antibody function by somatic mutation: unequal occurrence is controlled by V gene combinatorial associations." The EMBO journal 14.12 (1995): 2784-2794, Jun. 1995.

Diamond, Betty, et al., "Somatic mutation of the T15 heavy chain gives rise to an antibody with autoantibody specificity." Proceedings of the National Academy of Sciences 81.18 (1984): 5841-5844, Sep. 1984.

On Solopova et al., "Bispecific Antibodies in Clinical Practice and Clinical Trials" (Literature Review). Clinical oncohematology. 2019;12(2):125-44, (2019).

Susumu Ohno et al., "Antigen-binding specificities of antibodies are primarily determined by seven residues of VH." Proceedings of the National Academy of Sciences 82.9 (1985): 2945-2949, May 1985.

Andrew A . Pakula et al., "Genetic analysis of protein stability and function." Annual review of genetics 23.1 (1989): 289-310, Dec. 1989.

A Royt et al., "Immunology", Mosby International Ltd., 1998, pp. 110-111.

Stuart Rudikoff et al., "Single amino acid substitution altering antigen-binding specificity." Proceedings of the National Academy of Sciences 79.6 (1982): 1979-1983, Mar. 1982.

Yarilin A.A., "Fundamentals of Immunology", Moscow, "Medicina", 1999, p. 172 English translation only the relevant part.

Rospatent, Office Action of the corresponding Russian Patent Application No. 2022101057., dated Jan. 24, 2024.

Rospatent, Office Action of RU 2022101057, (National phase of PCT/KR2020/009870), dated Jun. 13, 2024.

Patrick W. B. Derksen et al., "Illegitimate WNT signaling promotes proliferation of multiple myeloma cells", PNAS, vol. 101, No. 16, pp. 6122-6127, Apr. 20, 2004.

Peter B. Dirks, "Brain Tumor Stem Cells: Bringing Order to the Chaos of Brain Cancer", Journal of Clinical Oncology, vol. 26, No. 17, pp. 2916-2924, Jun. 10, 2008.

Miguel López-Lázaro, "The migration ability of stem cells can explain the existence of cancer of unknown primary site. Rethinking metastasis.", Oncoscience 2015, vol. 2, No. 5, pp. 417-421, May 1, 2015.

B. Tran et al., "Survival comparison between glioblastoma multiforme and other incurable cancers", Journal of Clinical Neuroscience, vol. 17, Issue 4, Apr. 2010, pp. 417-421.

* cited by examiner

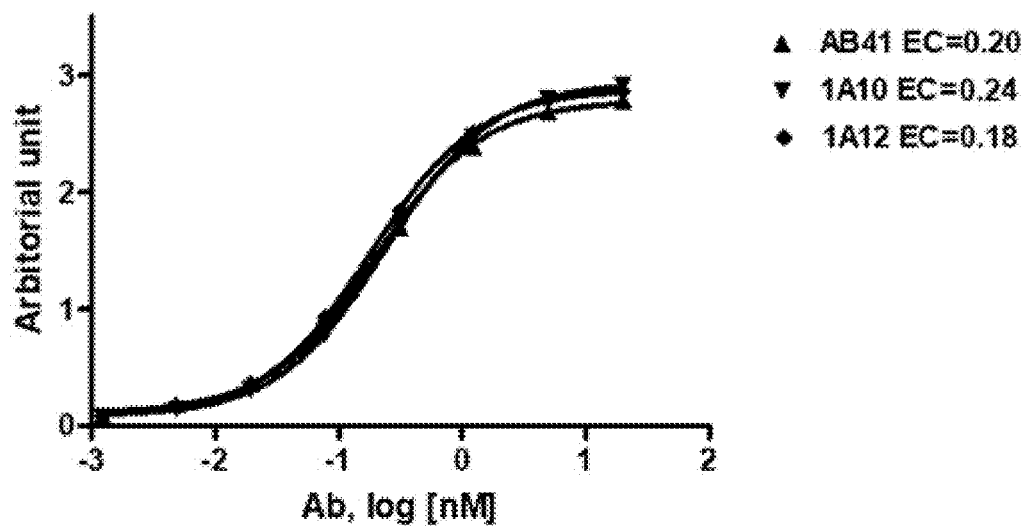
[FIG. 1a]
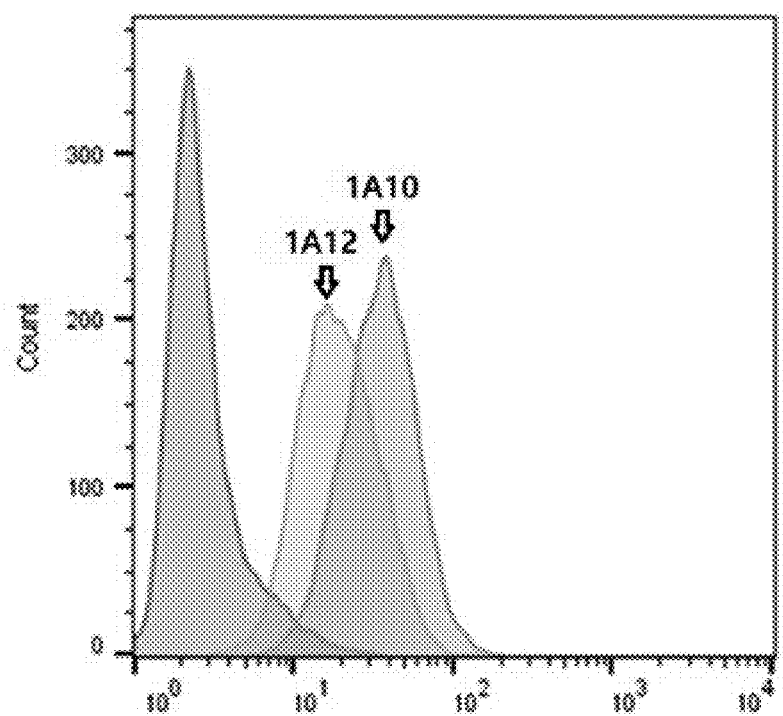
[FIG. 1b]

[FIG. 2a]
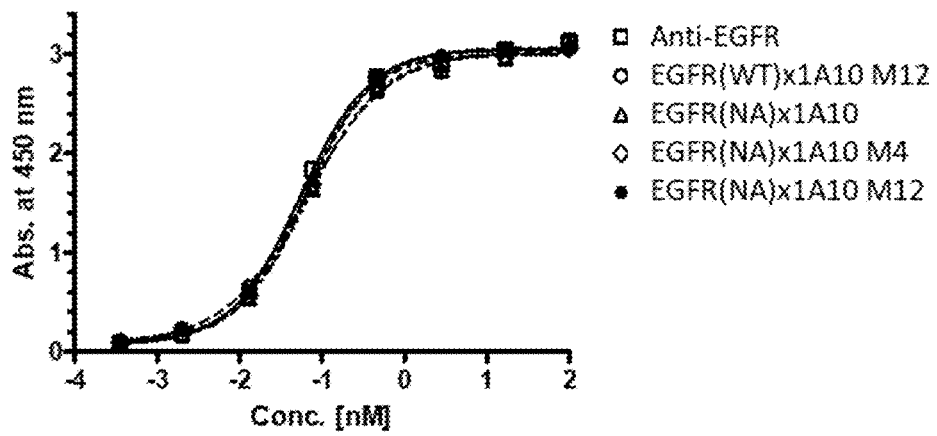
[FIG. 2b]
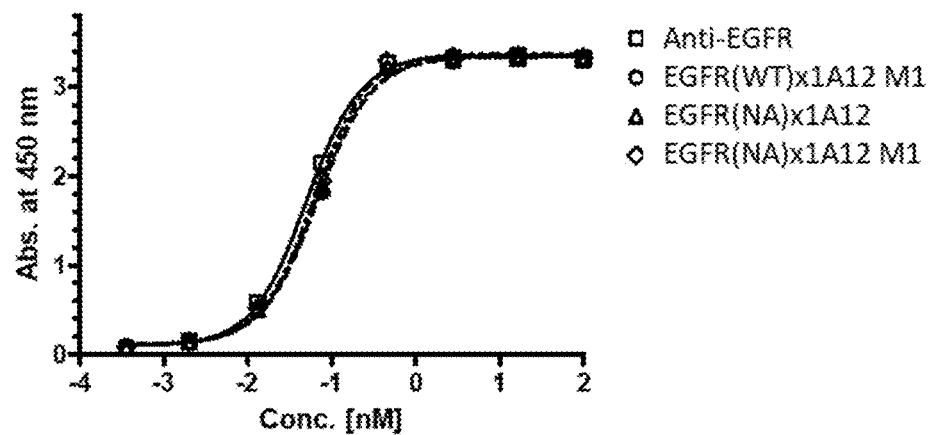

[FIG. 3a]
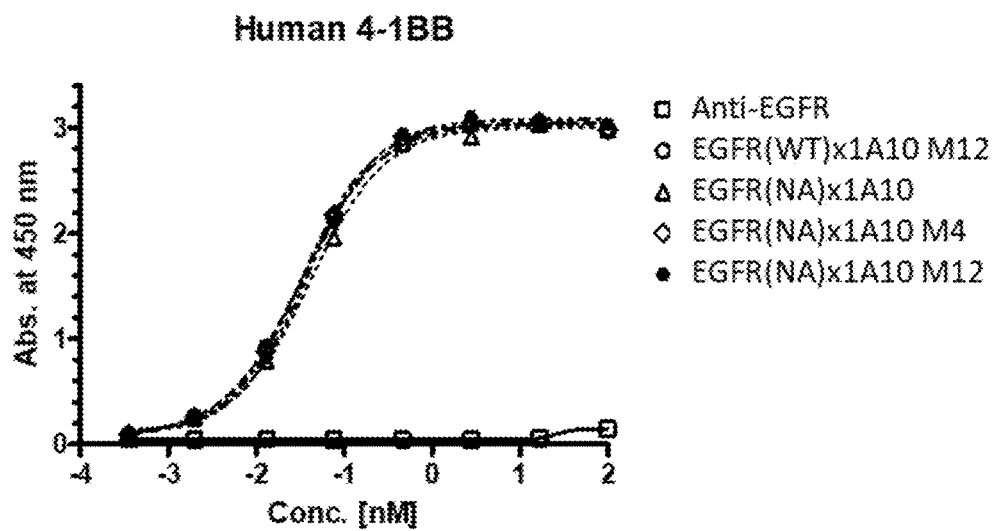
[FIG. 3b]
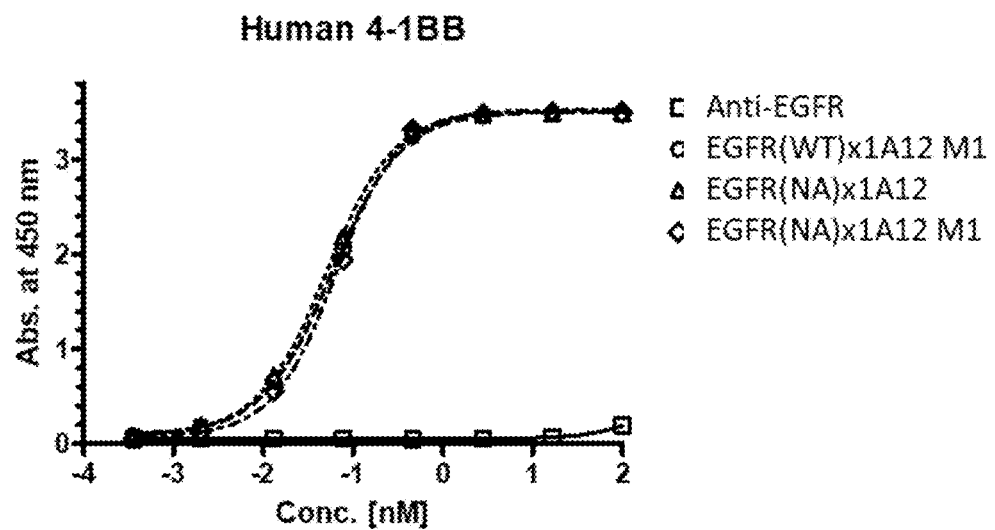

[FIG. 4a]
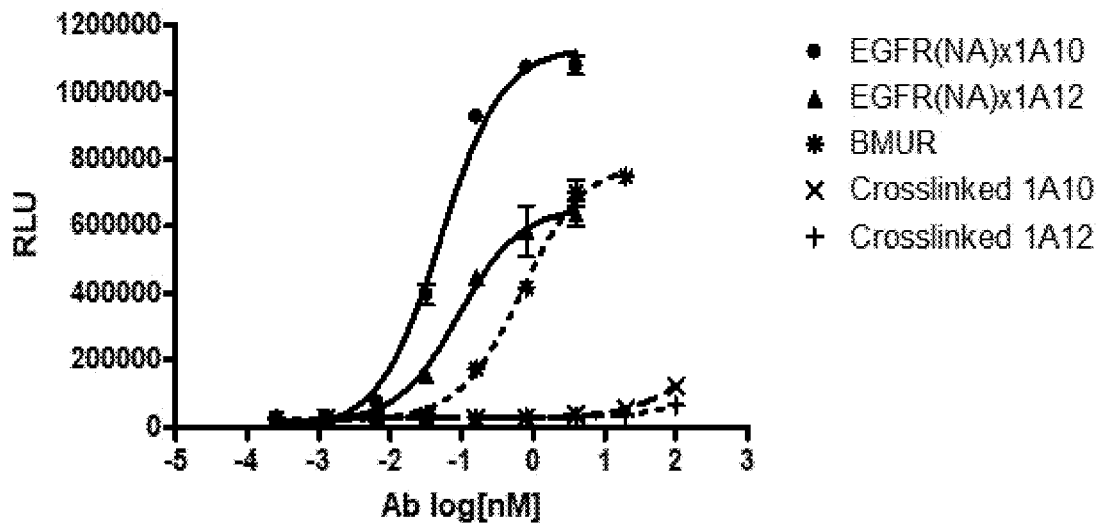
[FIG. 4b]
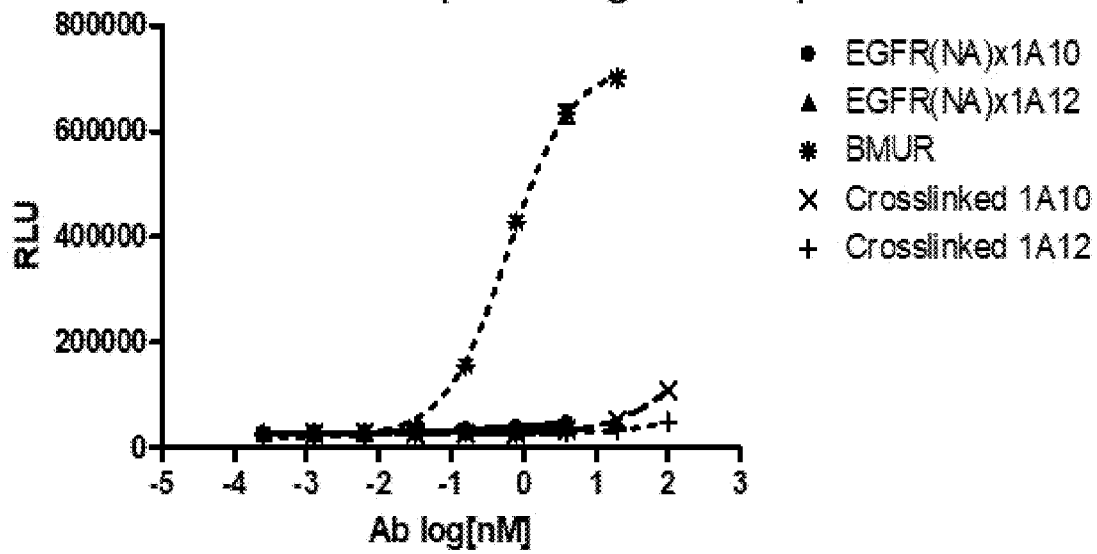

[FIG. 5a]
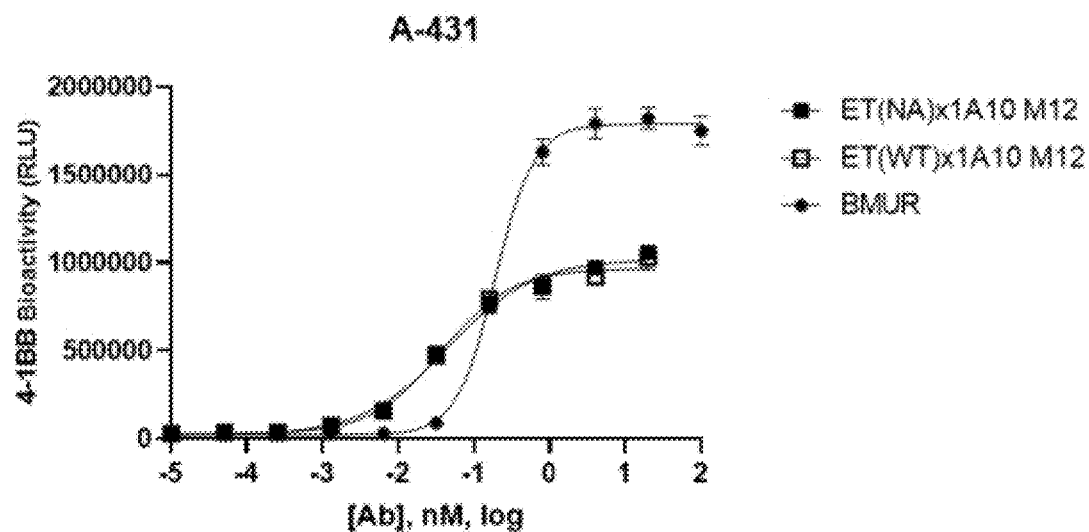
[FIG. 5b]
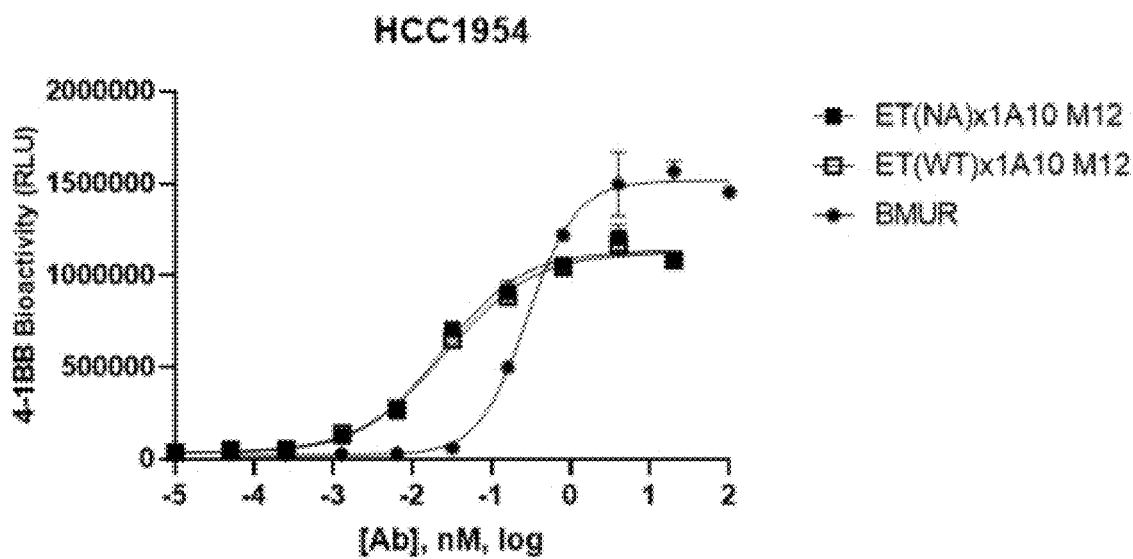

[FIG. 5c]
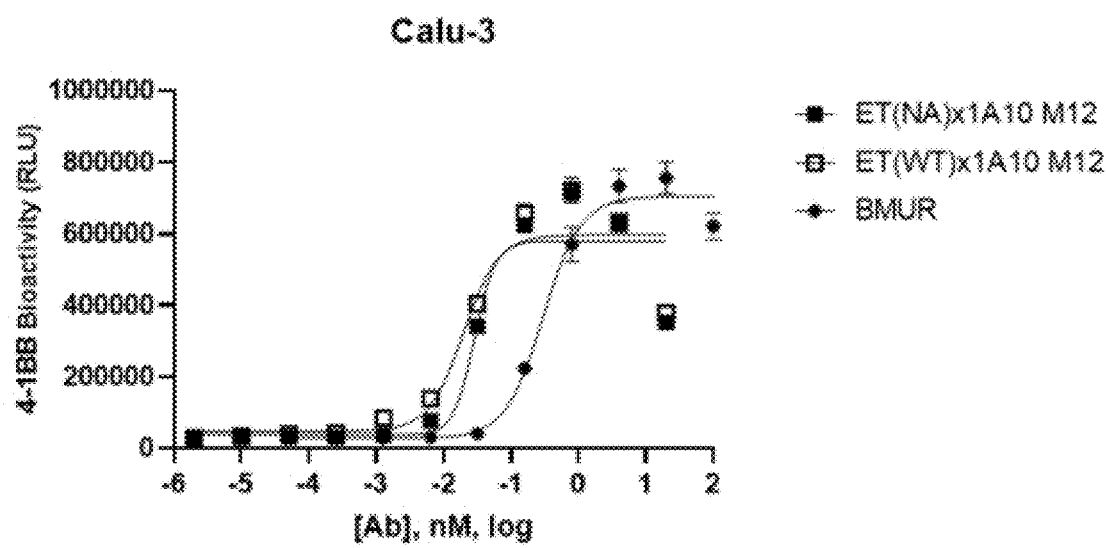
[FIG. 5d]
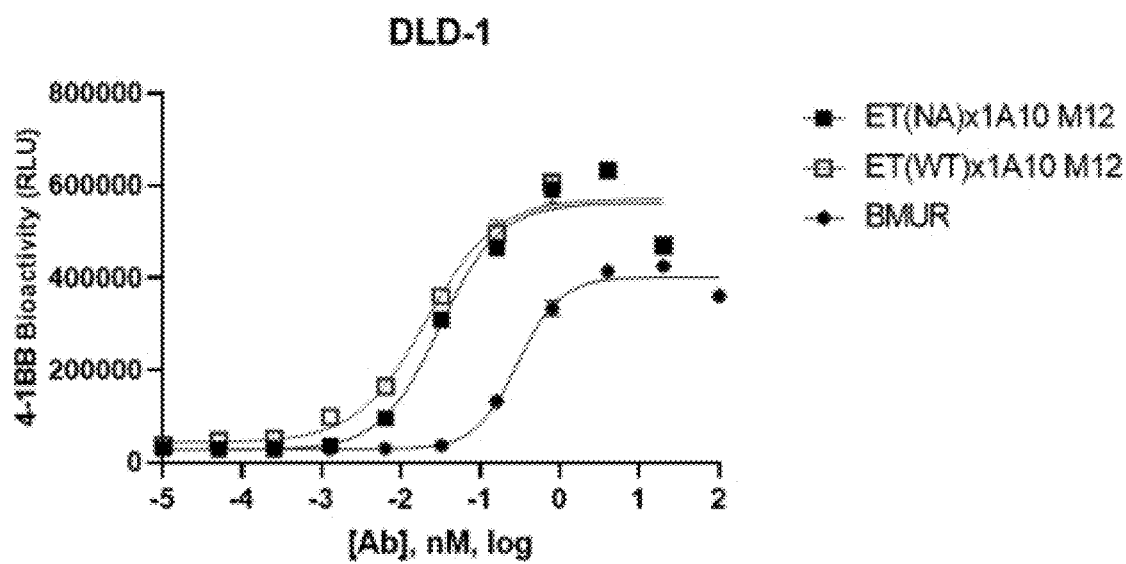

[FIG. 5e]
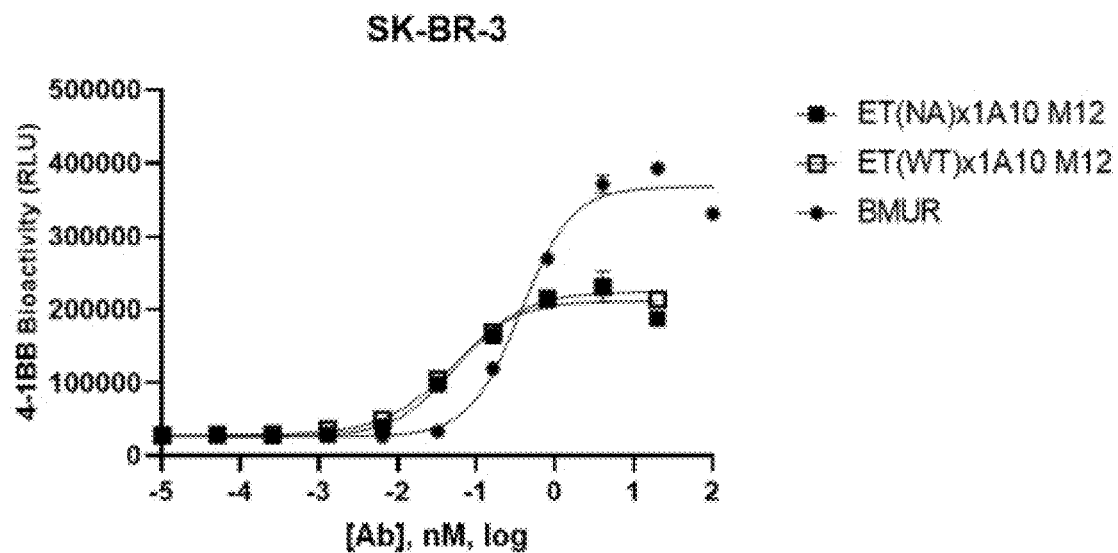
[FIG. 5f]
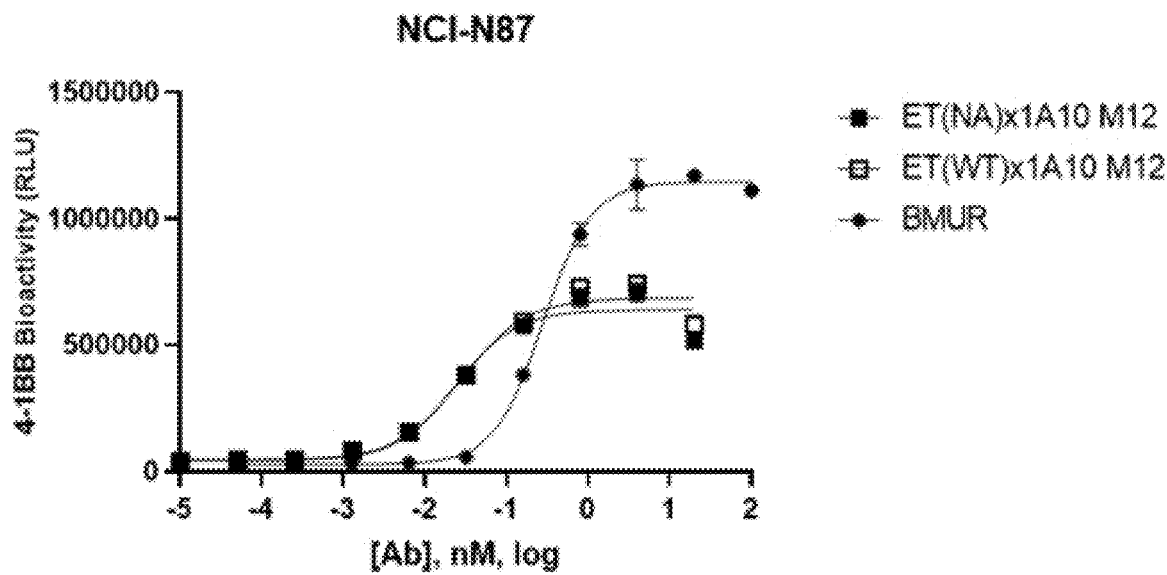

[FIG. 5g]
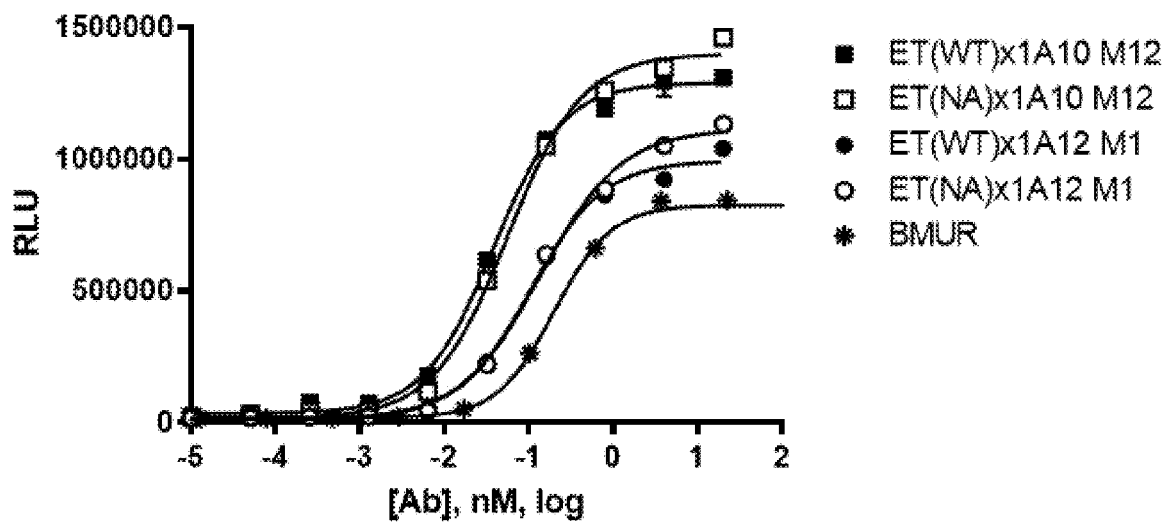
[FIG. 5h]
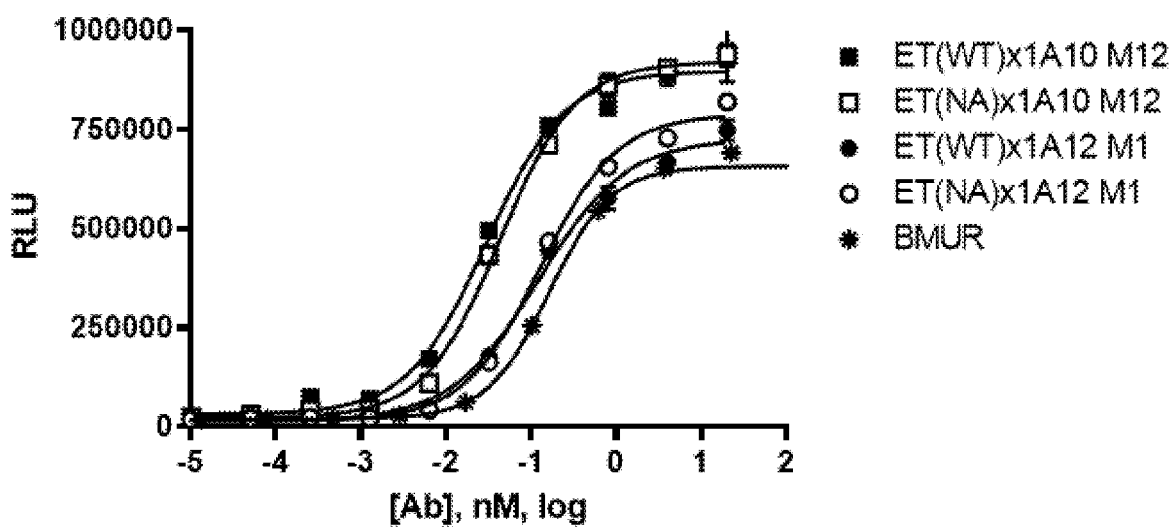

[FIG.6a]
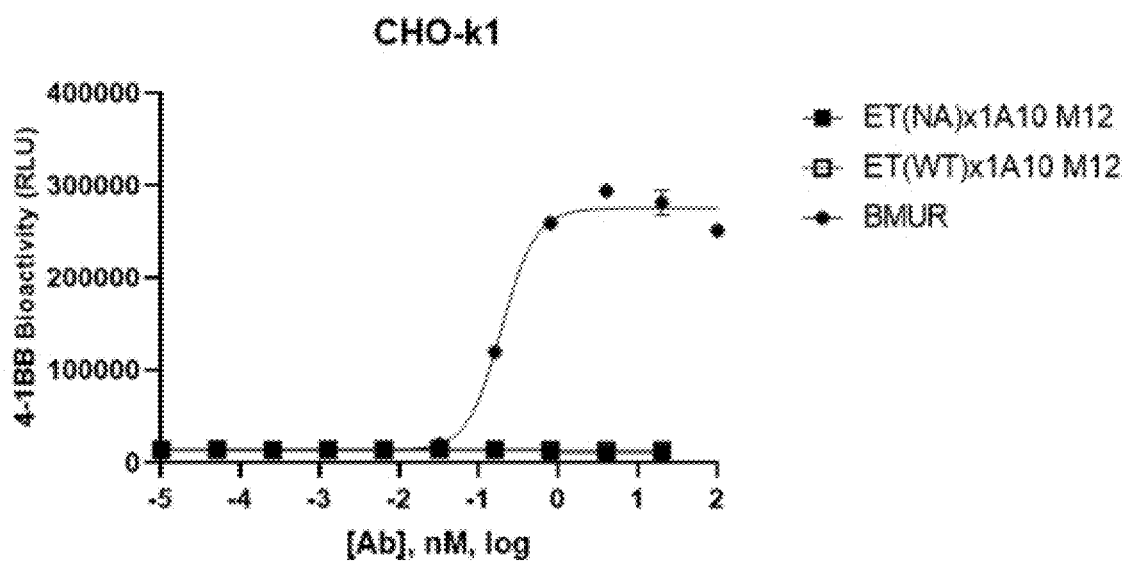
[FIG. 6b]
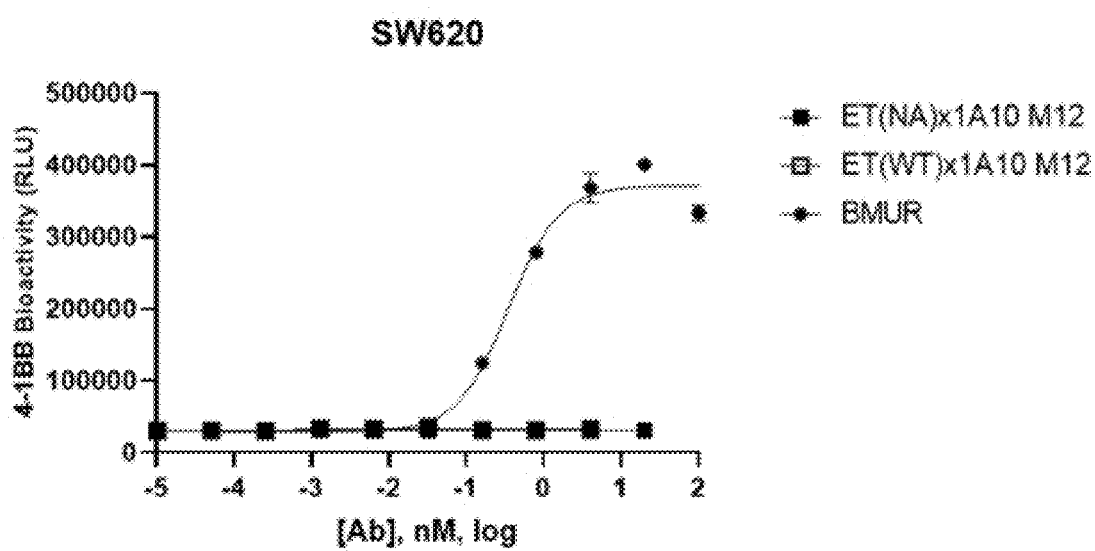

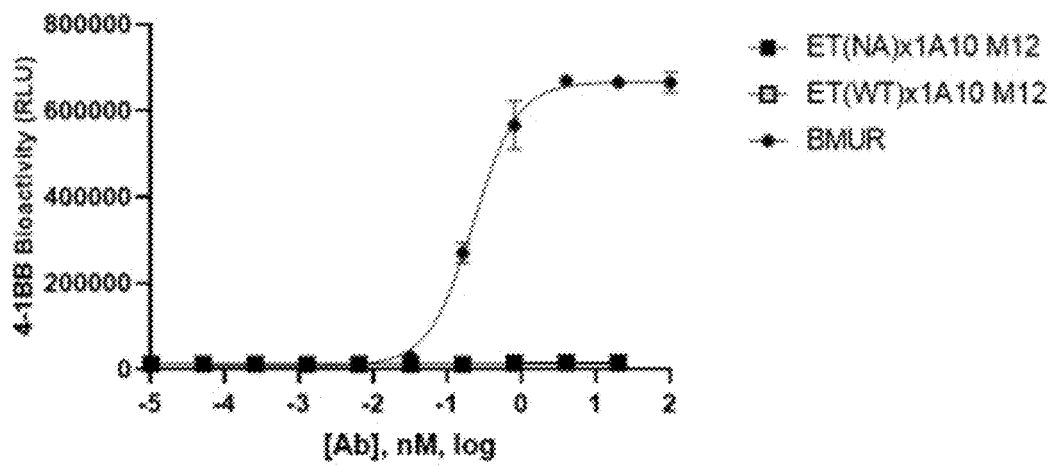
[FIG. 6c]
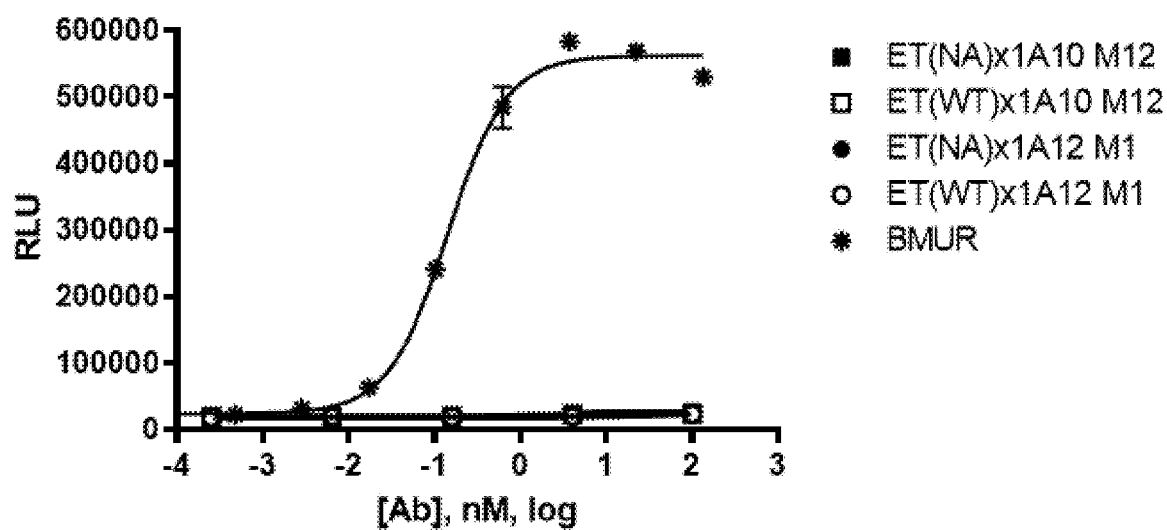
[FIG. 6d]

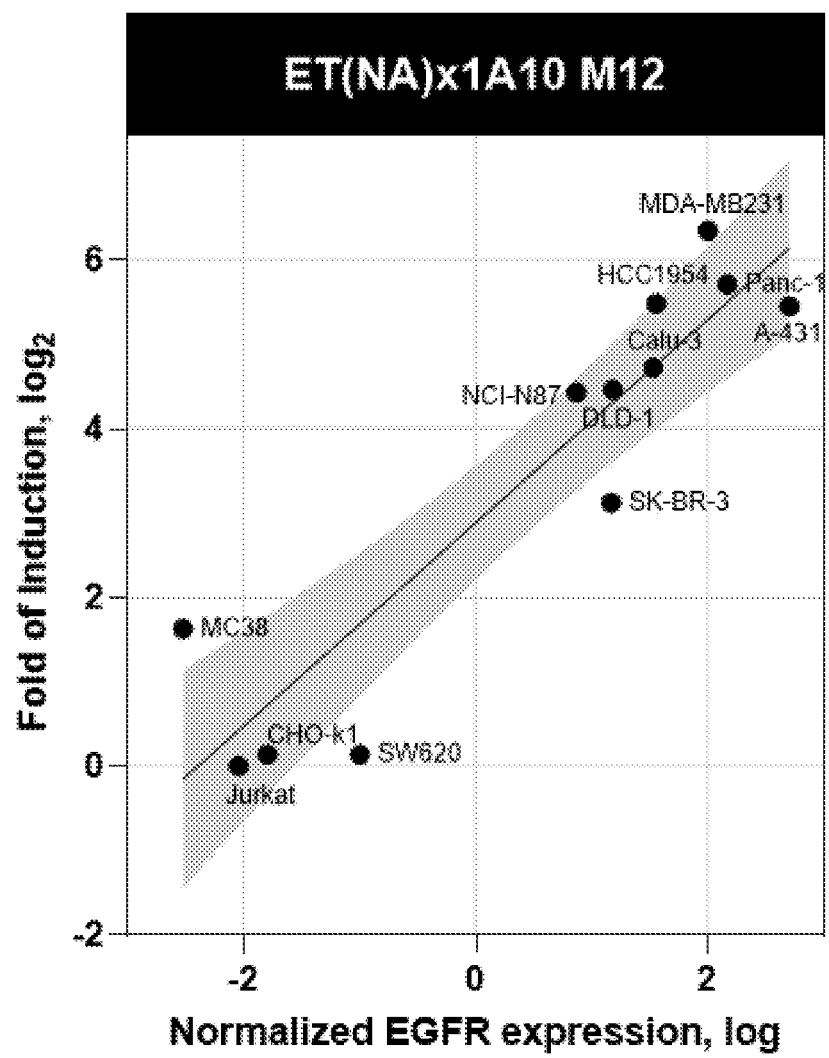
[FIG. 7a]

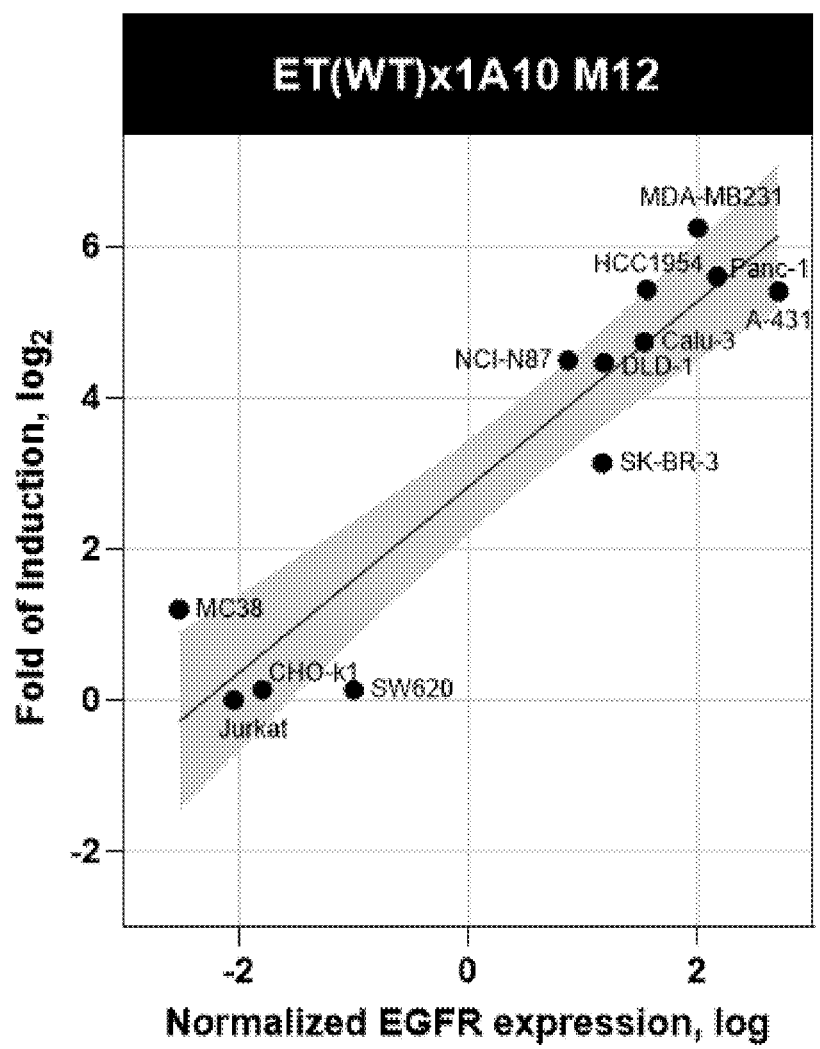
[FIG. 7b]

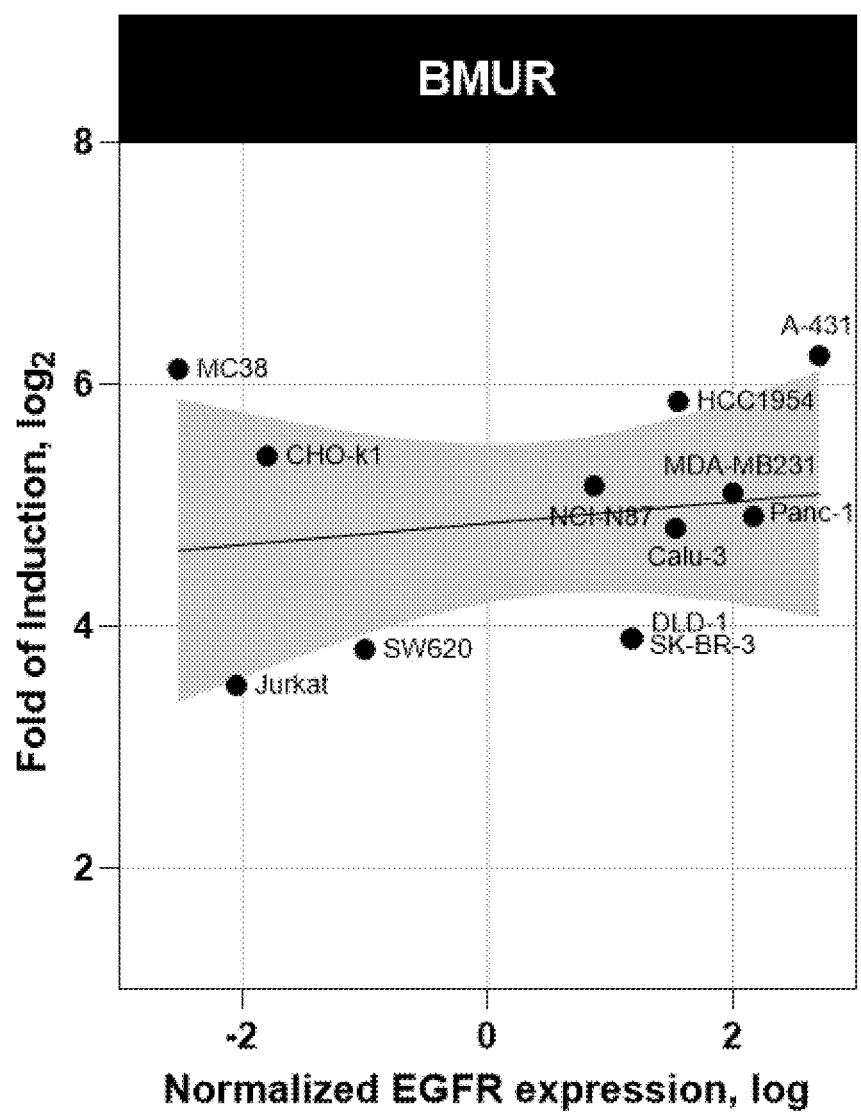
[FIG. 7c]

[FIG. 8a]
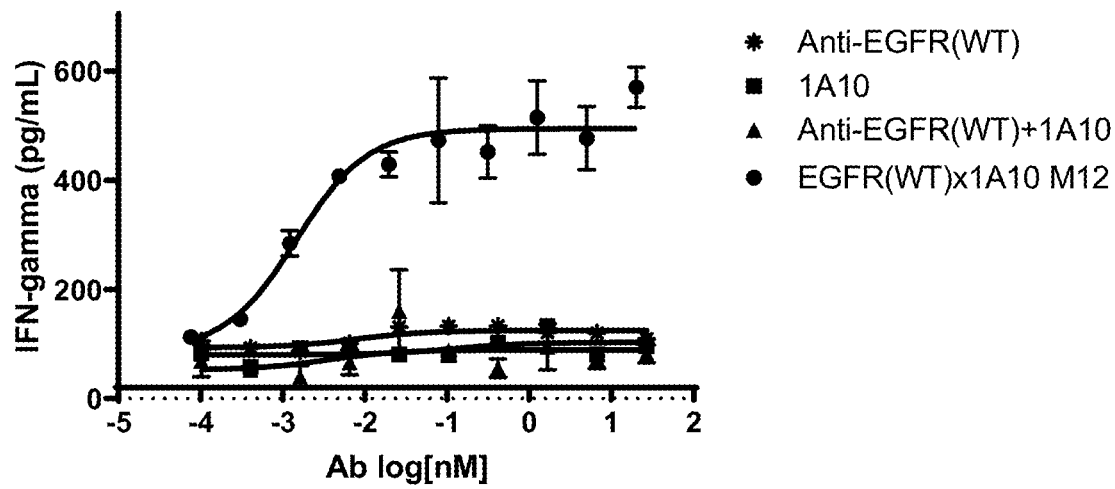
[FIG. 8b]
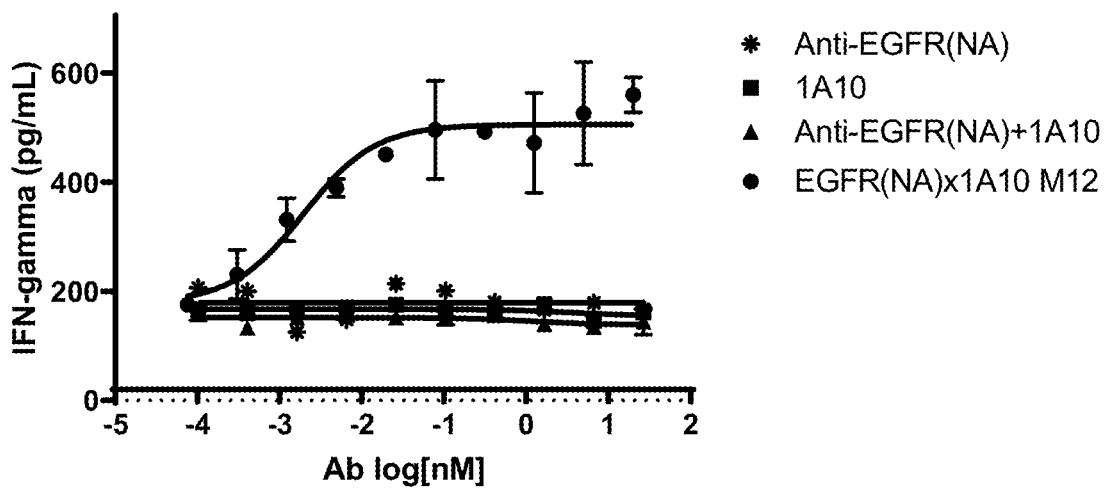

[FIG. 9a]
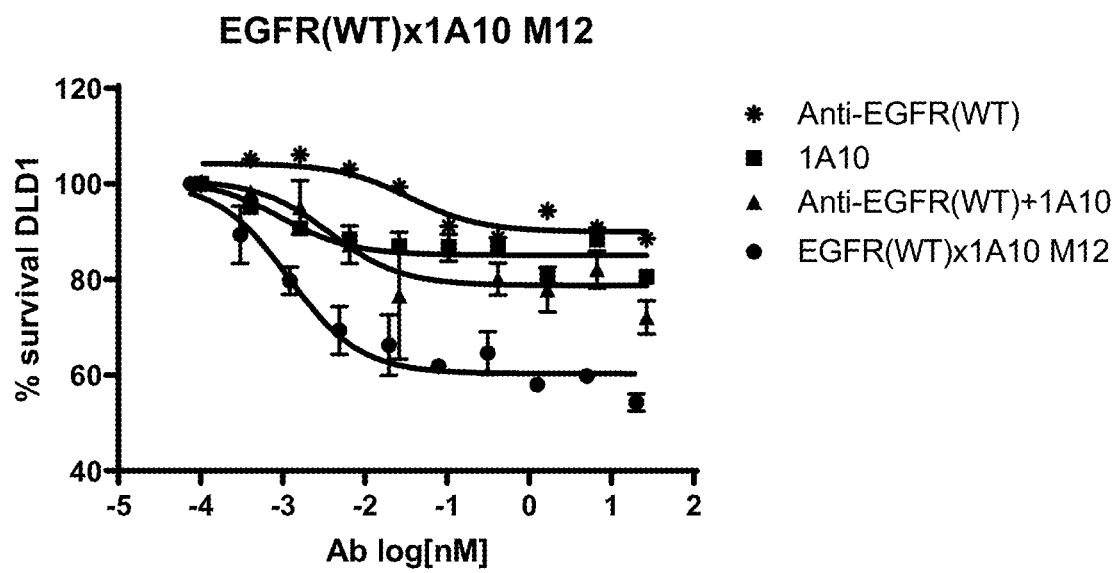
[FIG. 9b]
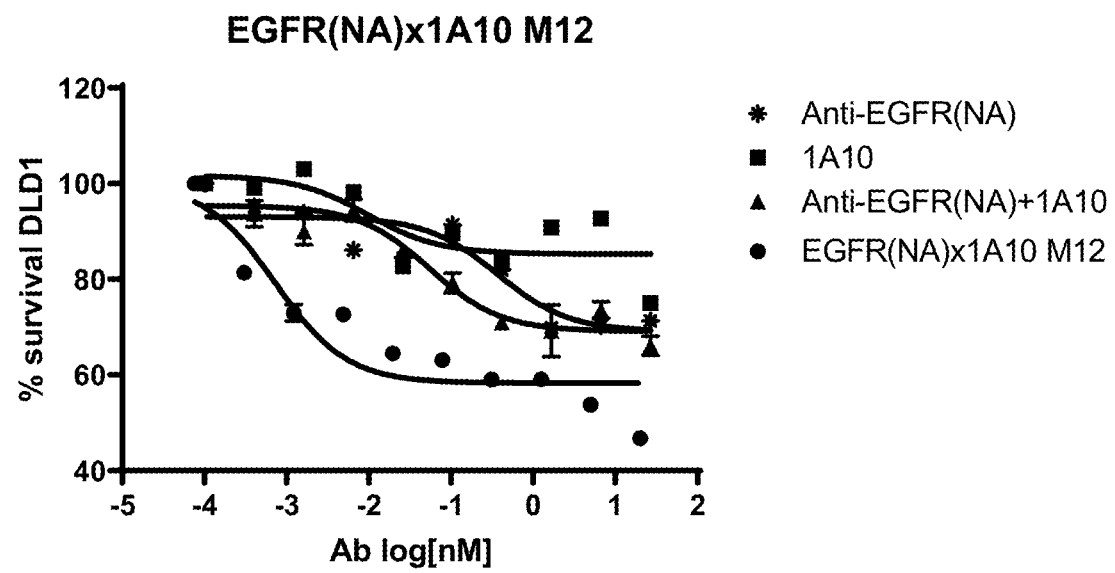

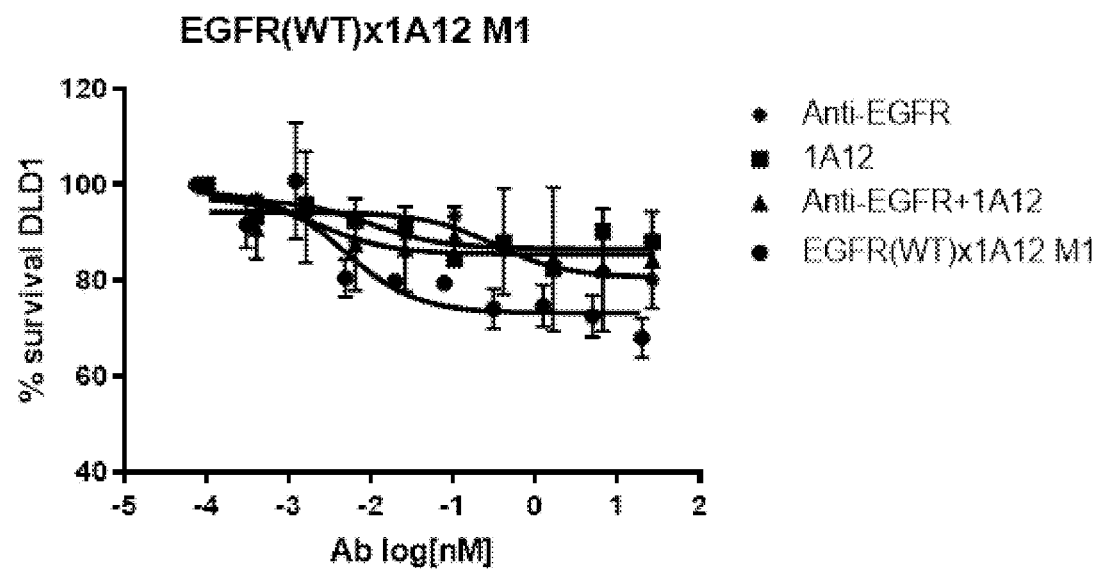
[FIG. 9c]
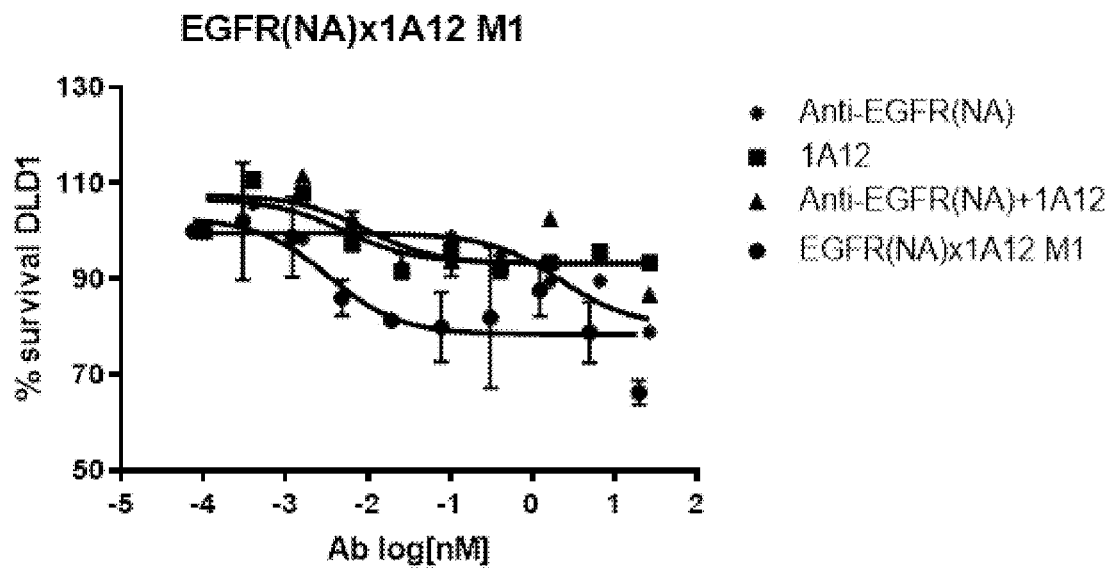
[FIG. 9d]

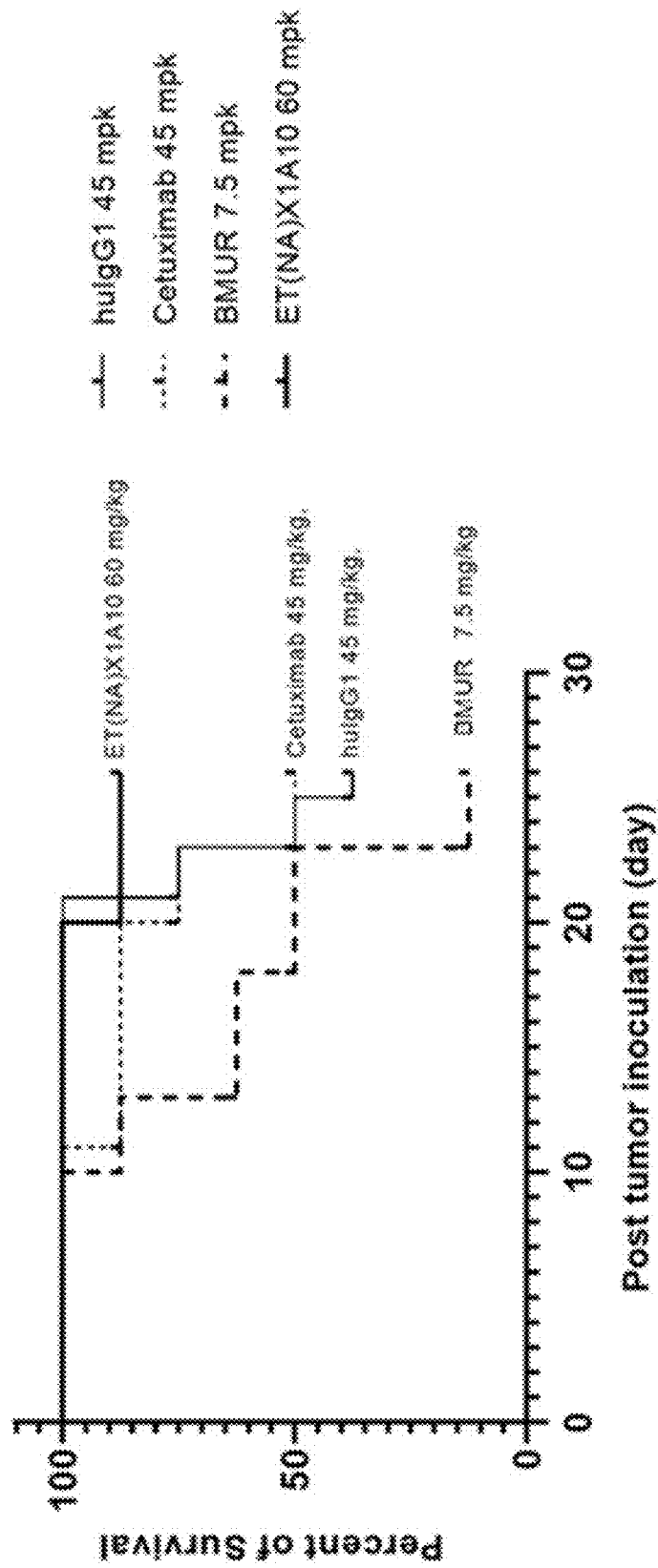
[FIG. 10]

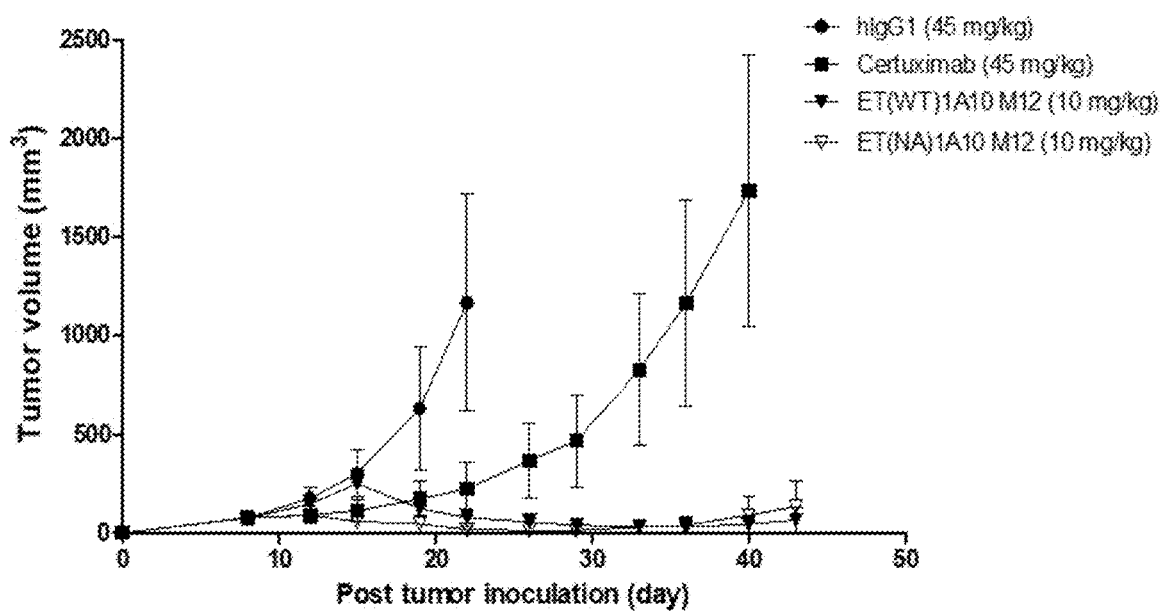
[FIG. 11a]
(Mean±SEM (n=5/group). *; p<0.01, ; p<0.01, *; p<0.001 vs hIgG1 control)

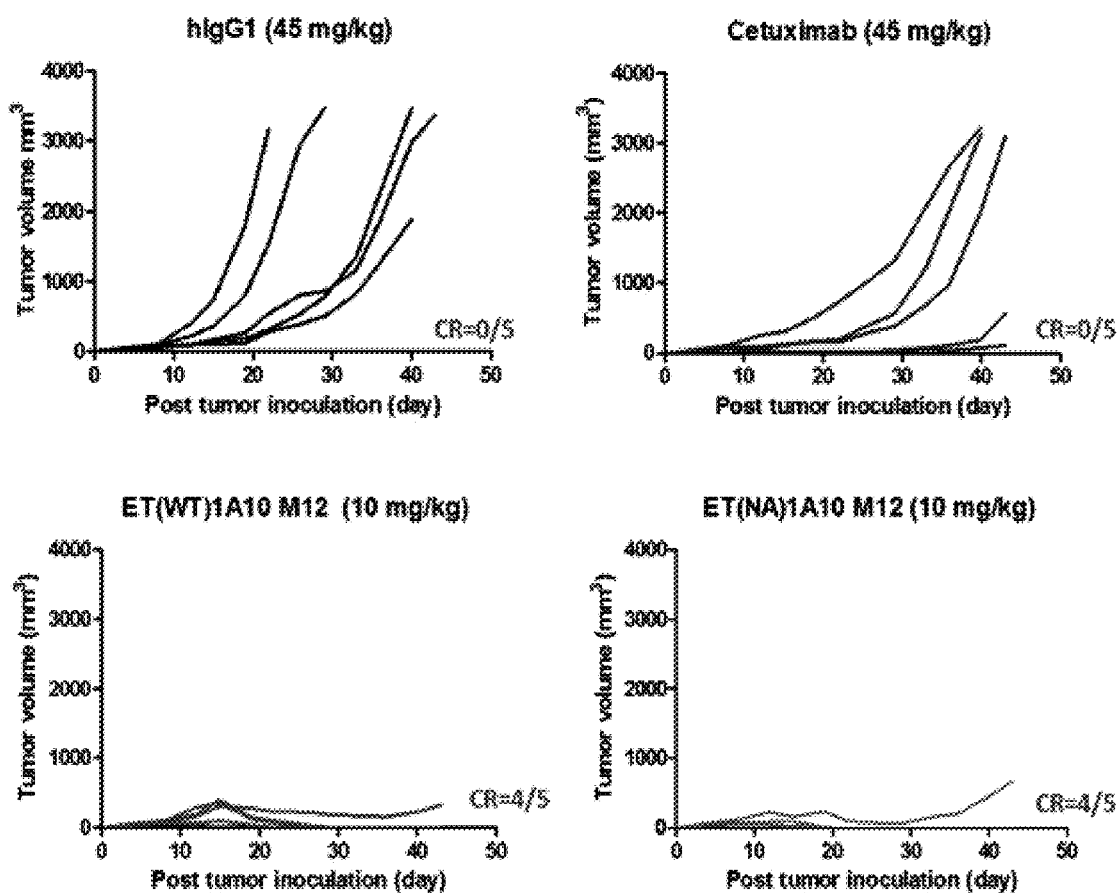
[FIG. 11b]

[FIG. 12]
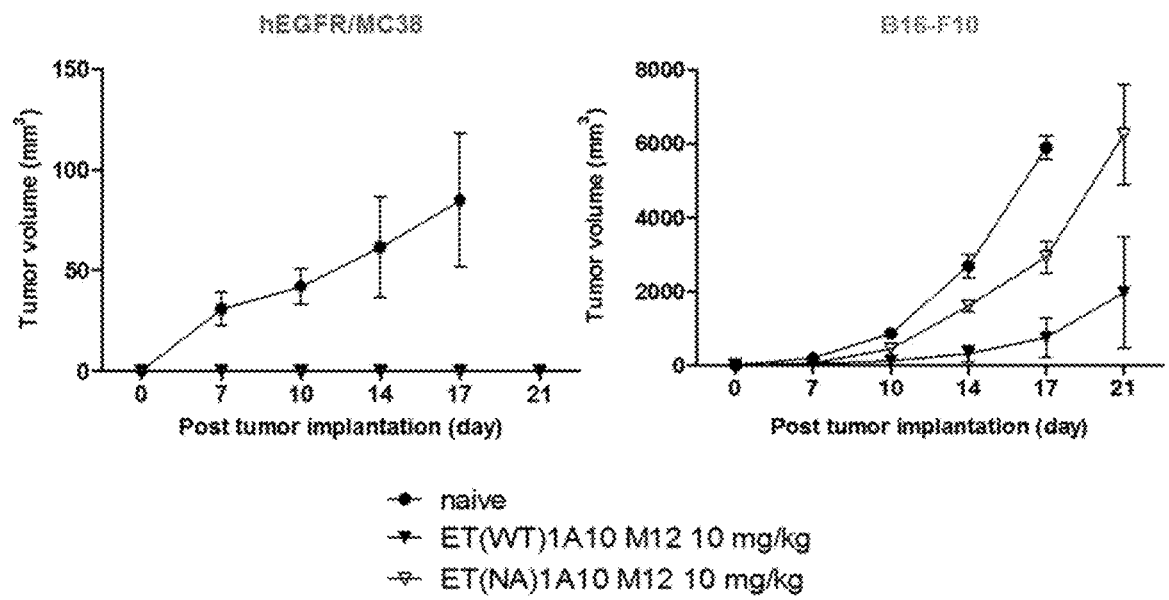
[FIG. 13]
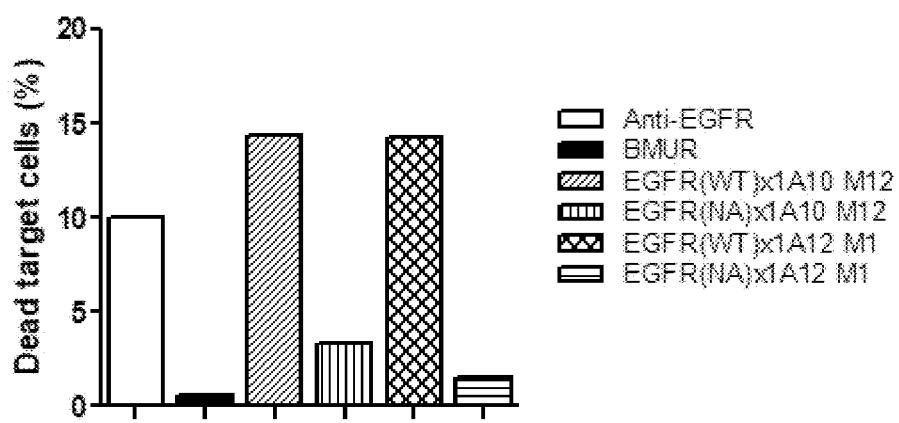

[FIG. 14a]
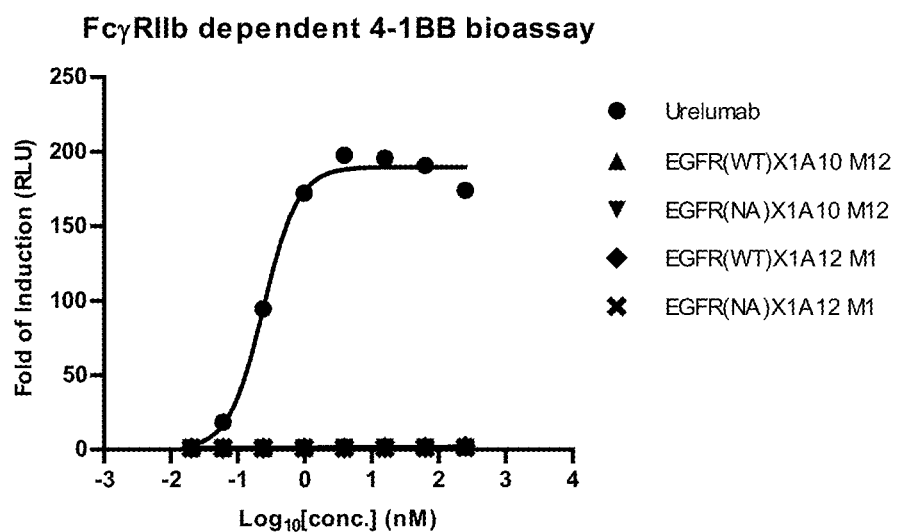
[FIG. 14b]
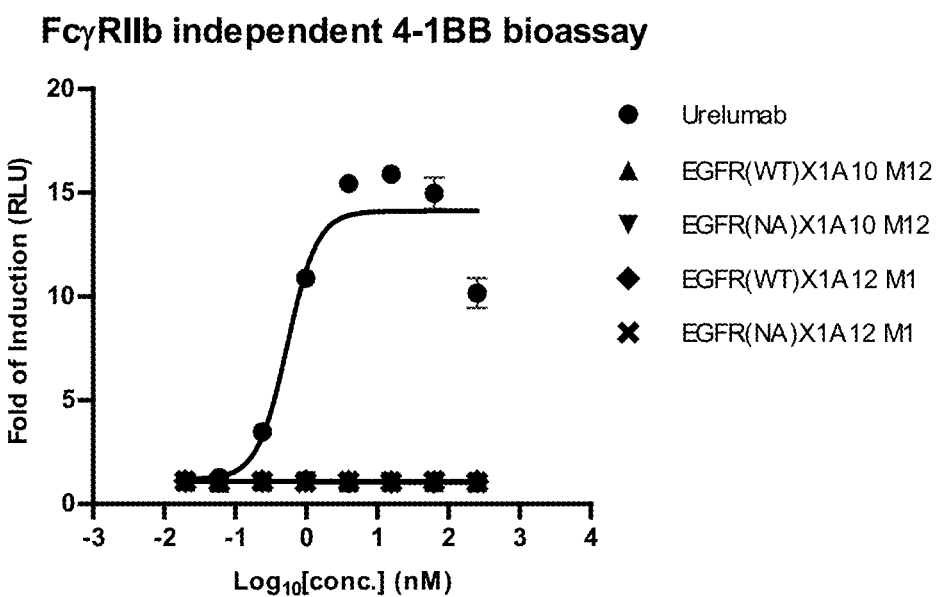

ANTI-EGFR/ANTI-4-1BB BISPECIFIC ANTIBODY

CROSS-REFERENCE TO RELATED APPLICATIONS

This application claims the benefit of U.S. 62/878,977 filed on Jul. 26, 2019 with the United States Patent and Trademark Office, the entire disclosure of which is herein incorporated by reference.

BACKGROUND OF THE INVENTION

1. Field

Provided are an anti-4-1BB/anti-EGFR bispecific antibody, and a pharmaceutical composition and a method for treating and/or preventing a cancer using the same.

2. Description of the Related Art 4-1BB protein is a member of TNF-receptor superfamily (TNFRSF) and is a co-stimulatory molecule which is expressed following the activation of immune cells, both innate and adaptive immune cells. 4-1BB plays important role in modulate the activity of various immune cells. 4-1BB agonists enhance proliferation and survival of immune cells, secretion of cytokines, and cytolytic activity CD8 T cells. Many other studies showed that activation of 4-1BB enhances immune response to eliminate tumors in mice. Therefore, it suggests that 4-1BB is a promising target molecule in cancer immunology. Despite of their anti-tumor efficacy, anti-4-1BB antibody induced severe liver toxicity in clinical application.

EGFR protein is a transmembrane protein that is a receptor for members of the epidermal growth factor family (EGF family) of extracellular protein ligands and involved in various mechanisms related to tumors. EGFR is a typical receptor tyrosine kinase (RTK) present on the surface of cells, and thereby inducing proliferation and penetration of cancer cells, angiogenesis, etc.

Meanwhile, multispecific antibodies targeting two or more antigens have been developed in various kinds and forms and are expected as a new drug antibody having excellent therapeutic effects compared to a monoclonal antibody.

Therefore, there is a need to develop a multispecific antibody capable of recognizing two different antigens wherein one is present on a cancer cell and the other is present on other cell such as an immune cell, for more efficient cancer therapy.

SUMMARY OF THE INVENTION

One embodiment provides an anti-EGFR/anti-4-1BB bispecific antibody, comprising:
(1) an anti-EGFR antibody or an antigen-binding fragment thereof, as an EGFR targeting moiety, which is capable of specifically recognizing and/or binding to EGFR protein; and
(2) an anti-4-1BB antibody or an antigen-binding fragment thereof, as a 4-1BB targeting moiety, which is capable of specifically recognizing and/or binding to 4-1BB protein.

Another embodiment provides a pharmaceutical composition comprising the bispecific antibody. The pharmaceutical composition may further comprise a pharmaceutically acceptable carrier. The pharmaceutical composition may be used for treating and/or preventing a cancer and/or for enhancing immune response.

Another embodiment provides a pharmaceutical composition for treating and/or preventing a cancer and/or for enhancing immune response, the composition comprising the bispecific antibody.

Another embodiment provides a method of treating and/or preventing a cancer in a subject in need thereof, comprising administering to the subject a pharmaceutically effective amount of the bispecific antibody or the pharmaceutical composition to the subject. The method may further comprise a step of identifying the subject in need of treating and/or preventing a cancer, prior to the administering step.

Another embodiment provides a method of enhancing immune response in a subject in need thereof, comprising administering to the subject a pharmaceutically effective amount of the bispecific antibody or the pharmaceutical composition to the subject. The method may further comprise a step of identifying the subject in need of enhancing immune response, prior to the administering step.

Another embodiment provides a use of the bispecific antibody or the pharmaceutical composition in treating and/or preventing a cancer. Another embodiment provides a use of the bispecific antibody in preparing a medicament for treating and/or preventing a cancer.

Another embodiment provides a use of the bispecific antibody or the pharmaceutical composition in enhancing immune response. Another embodiment provides a use of the bispecific antibody in preparing a medicament for enhancing immune response.

An embodiment provides a polynucleotide encoding the bispecific antibody.

An embodiment provides a recombinant vector comprising the polynucleotide. The recombinant vector may be used as an expression vector of a polynucleotide encoding the bispecific antibody.

Another embodiment provides a cell comprising a polynucleotide encoding the bispecific antibody. The cell may be a recombinant cell transfected with a recombinant vector comprising the polynucleotide.

Another embodiment provides a method of preparing the bispecific antibody, comprising expressing the polynucleotide in a cell. The step of expressing the polynucleotide may be conducted by culturing the cell comprising the polynucleotide (for example, in a recombinant vector) under a condition allowing the expression of the polynucleotide.

BRIEF DESCRIPTION OF THE DRAWINGS

FIG. 1a is a graph showing antigen (human 4-1BB) binding activities of anti-4-1BB antibodies measured by ELISA.

FIG. 1b is a graph showing cell binding activities of anti-4-1BB antibodies measured by ELISA.

FIG. 2a is a graph showing antigen (human EGFR) binding activities of anti-EGFR/anti-4-1BB bispecific antibodies measured by ELISA.

FIG. 2b is a graph showing antigen (human EGFR) binding activities of anti-EGFR/anti-4-1BB bispecific antibodies measured by ELISA.

FIG. 3a is a graph showing antigen (human 4-1BB) binding activities of anti-EGFR/anti-4-1BB bispecific antibodies measured by ELISA.

FIG. 3b is a graph showing antigen (human 4-1BB) binding activities of anti-EGFR/anti-4-1BB bispecific antibodies measured by ELISA.

FIG. 4a is a graph showing 4-1BB signal activation level by anti-EGFR/anti-4-1BB bispecific antibodies in MDA-MB231 cell line (EGFR high expressing cells).

FIG. 4b is a graph showing 4-1BB signal activation level by anti-EGFR/anti-4-1BB bispecific antibodies in BT-474 cell line (EGFR negative cells).

FIG. 5a is a graph showing 4-1BB signal activation level by an anti-EGFR/anti-4-1BB bispecific antibody in EGFR-expressing A431 cell line.

FIG. 5b is a graph showing 4-1BB signal activation level by an anti-EGFR/anti-4-1BB bispecific antibody in EGFR-expressing HCC1954 cell line.

FIG. 5c is a graph showing 4-1BB signal activation level by an anti-EGFR/anti-4-1BB bispecific antibody in EGFR-expressing Calu-3 cell line.

FIG. 5d is a graph showing 4-1BB signal activation level by an anti-EGFR/anti-4-1BB bispecific antibody in EGFR-expressing DLD-1 cell line.

FIG. 5e is a graph showing 4-1BB signal activation level by an anti-EGFR/anti-4-1BB bispecific antibody in EGFR-expressing SK-BR-3 cell line.

FIG. 5f is a graph showing 4-1BB signal activation level by an anti-EGFR/anti-4-1BB bispecific antibody in EGFR-expressing NCI-N87 cell line.

FIG. 5g is a graph showing 4-1BB signal activation level by an anti-EGFR/anti-4-1BB bispecific antibody in EGFR-expressing MDA-MB-231 cell line.

FIG. 5h is a graph showing 4-1BB signal activation level by an anti-EGFR/anti-4-1BB bispecific antibody in EGFR-expressing Panc-1 cell line.

FIG. 6a is a graph showing 4-1BB signal activation level by an anti-EGFR/anti-4-1BB bispecific antibody in EGFR-non-expressing CHO-k1 cell line.

FIG. 6b is a graph showing 4-1BB signal activation level by an anti-EGFR/anti-4-1BB bispecific antibody in EGFR-non-expressing SW620 cell line.

FIG. 6c is a graph showing 4-1BB signal activation level by an anti-EGFR/anti-4-1BB bispecific antibody in EGFR-non-expressing MC38 cell line.

FIG. 6d is a graph showing 4-1BB signal activation level by an anti-EGFR/anti-4-1BB bispecific antibody in EGFR-non-expressing Jurkat cell line.

FIGS. 7a-7c are graphs showing correlation between the EGFR sABC and 4-1BB-induced NF-kB signaling by anti-EGFR/anti-4-1BB bispecific antibody (7a, 7b) and control antibody (7c) in various cell lines.

FIGS. 8a and 8b are graphs showing IFN-gamma level released from EGFR-expressing DLD-1 cells treated with anti-EGFR/anti-4-1BB bispecific antibodies.

FIGS. 9a-9d are graphs showing % survival of EGFR-expressing DLD-1 cells treated with anti-EGFR/anti-4-1BB bispecific antibodies.

FIG. 10 is a graph showing in vivo anti-tumor activities by anti-EGFR/anti-4-1BB bispecific antibodies in DLD-1 bearing hPBMC engrafted mice.

FIGS. 11a and 11b are graphs showing in vivo anti-tumor activities by anti-EGFR/anti-4-1BB bispecific antibodies in human EGFR/MC38 tumor bearing 4-1BB knock-in mice.

FIG. 12 is a graph showing in vivo anti-tumor activities by anti-EGFR/anti-4-1BB bispecific antibodies in mice cured by anti-EGFR/anti-4-1BB bispecific antibody and re-challenged with human EGFR/MC38 tumor cells and B16 F10 tumor cells.

FIG. 13 is a graph showing antibody-dependent cellular cytotoxicity (ADCC) effects of anti-EGFR/anti-4-1BB bispecific antibodies.

FIG. 14a is a graph showing results of FcγRIIb-dependent 4-1BB bioassay for anti-EGFR/anti-4-1BB bispecific antibodies.

FIG. 14b is a graph showing results of FcγRIIb-independent 4-1BB bioassay for anti-EGFR/anti-4-1BB bispecific antibodies.

DETAILED DESCRIPTION OF THE INVENTION

The present disclosure relates to bispecific antibodies, each of which comprises an antibody specific to a tumor associated antigen (TAA; EGFR) and an antibody specific to 4-1BB, and uses thereof. These bispecific antibodies activate 4-1BB signaling and boost strong immune cell only in presence of EGFR expressing cells. Due to specific EGFR-mediated immune response, it is expected to have much less liver toxicity by using bispecific antibodies compared to 4-1BB monoclonal antibody.

In the present disclosure, provided is an anti-EGFR/anti-4-1BB bispecific antibody, and uses thereof, wherein the anti-EGFR/anti-4-1BB bispecific antibody may comprise:

(1) an anti-EGFR antibody or an antigen-binding fragment thereof, as an EGFR targeting moiety, which is capable of specifically recognizing and/or binding to EGFR protein, and (2) an anti-4-1BB antibody or an antigen-binding fragment thereof, as a 4-1BB targeting moiety, which is capable of specifically recognizing and/or binding to 4-1BB protein.

Hereinafter, the present invention is described in more detail.

Definition

As used herein, 'consisting of a sequence,' 'consisting essentially of a sequence,' or 'comprising a sequence' may refer to any case comprising the sequence, but it may not be intended to exclude a case comprising further sequence other than the sequence.

As used herein, the term 'a protein or polypeptide comprising or consisting of an amino acid sequence identified by SEQ ID NO' and 'a gene or polynucleotide comprising or consisting of a nucleic acid sequence identified by SEQ ID NO' may refer to a protein (or polypeptide) or gene (or polynucleotide), which consists essentially of the amino acid sequence or nucleic acid sequence, or which has at least 90%, at least 91%, at least 92%, at least 93%, at least 94%, at least 95%, at least 96%, at least 97%, at least 98%, or at least 99% sequence identity with the amino acid sequence or nucleic acid sequence with maintaining its inherent activity and/or function.

As used herein, the term "antibody" may encompass various broad classes of polypeptides that can be distinguished biochemically. Those skilled in the art will appreciate that heavy chains are classified as gamma, mu, alpha, delta, or epsilon (γ, μ, α, δ, ε) with some subclasses among them (e.g., γ1-γ4), and light chains are classified as either kappa or lambda (κ, λ). It is the nature of this chain that determines the "class" of the antibody as IgG, IgM, IgA IgG, or IgE, respectively. The immunoglobulin subclasses (isotypes), e.g., IgG1, IgG2, IgG3, IgG4, IgG5, etc., are well characterized and are known to confer functional specialization.

An intact antibody includes two full-length light chains and two full-length heavy chains, in which each light chain is linked to a heavy chain by disulfide bonds. The antibody has a heavy chain constant region and a light chain constant region. The heavy chain constant region is of a gamma (γ), mu (μ), alpha (α), delta (δ), or epsilon (ε) type, which may be further categorized as gamma 1 (γ1), gamma 2 (γ2), gamma 3 (γ3), gamma 4 (γ4), alpha 1 (α1), or alpha 2 (α2). The light chain constant region is of either a kappa (κ) or lambda (λ) type.

The term "heavy chain" refers to a full-length heavy chain or a fragment thereof, including a variable region $V_H$ that includes amino acid sequences sufficient to provide specificity to antigens, and three constant regions, $C_{H1}$, $C_{H2}$, and $C_{H3}$, and a hinge. The term "light chain" refers to a full-length light chain or a fragment thereof, including a variable region $V_L$ that includes amino acid sequences sufficient to provide specificity to antigens, and a constant region CL.

The term "complementarity determining region (CDR)" refers to an amino acid sequence found in a hyper variable region of a heavy chain or a light chain of immunoglobulin. The heavy and light chains may respectively include three CDRs (CDRH1, CDRH2, and CDRH3; and CDRL1, CDRL2, and CDRL3). The CDR may provide residues that play an important role in the binding of antibodies to an antigens or epitope. The terms "specifically binding" or "specifically recognized" is well known to one of ordinary skill in the art, and indicates that an antibody and an antigen specifically interact with each other to lead to an immunological activity.

In this disclosure, the antibody may include, but not be limited to, polyclonal or monoclonal; and/or human, humanized, animal (e.g., mouse, rabbit, etc.) derived antibody, or chimeric antibodies (e.g., mouse-human chimeric antibody).

An animal-derived antibody which is produced by immunizing an animal with a desired antigen may generally trigger an immune rejection response when administered to humans for treatment purpose, and a chimeric antibody has been developed to suppress such immune rejection response. A chimeric antibody is formed by replacing the constant region of an animal-derived antibody, which is a cause of anti-isotype response, with the constant region of a human antibody using genetic engineering methods. The chimeric antibody has considerably improved anti-isotype response in comparison with animal-derived antibodies, but animal-derived amino acids are still present in its variable regions and thus it still contains potential side effects resulting from an anti-idiotypic response. It is a humanized antibody that has been thus developed to improve such side effects. This is manufactured by grafting CDR (complementarity determining regions) which, of the variable regions of a chimeric antibody, has an important role in antigen binding into a human antibody framework.

As used herein, the term "antigen binding fragment" refers to a fragment derived from a full immunoglobulin structure including a portion capable of binding to an antigen such as CDRs. For example, the antigen binding fragment may be scFv, (scFv)$_2$, Fab, Fab', or F(ab')$_2$, but not be limited thereto. In the present disclosure, the antigen binding fragment may be a fragment derived from an antibody, including at least one complementarity determining region, for example, selected from the group consisting of scFv, (scFv)$_2$, scFv-Fc, Fab, Fab' and F(ab')$_2$.

Of the antigen binding fragments, Fab is a structure having variable regions of a light chain and a heavy chain, a constant region of the light chain, and the first constant region ($C_{H1}$) of the heavy chain, and it has one antigen binding site.

Fab' is different from Fab in that it has a hinge region including one or more cysteine residues at the C-terminal of heavy chain $C_{H1}$ domain. An F(ab')$_2$ antibody is formed through disulfide bond of the cysteine residues at the hinge region of Fab'.

Fv is a minimal antibody piece having only a heavy chain variable region and light chain variable region, and a recombinant technique for producing the Fv fragment is well known in the pertinent art. Two-chain Fv may have a structure in which the heavy chain variable region is linked to the light chain variable region by a non-covalent bond, and single-chain Fv (scFv) may generally have a dimer structure as in the two-chain Fv in which the variable region of a heavy chain and the variable region of a light chain are covalently linked via a peptide linker or they are directly linked to each other at the C-terminal thereof.

The antigen binding fragments may be obtained using proteases (for example, a whole antibody is digested with papain to obtain Fab fragments, and is digested with pepsin to obtain F(ab')2 fragments), and may be prepared by a genetic recombinant technique.

Immunoglobulin (e.g., a human immunoglobulin) or antibody molecules of the disclosure can be of any type (e.g., IgG, IgE, IgM, IgD, IgA, IgY, etc.), class (e.g., IgG1, IgG2, IgG3, IgG4, IgG5, IgA1, IgA2, etc.), or subclass of immunoglobulin molecule.

In the antibody or antibody fragment, portions (e.g., constant regions) except the CDRs or variable regions may be derived from a human antibody and particularly, they may be derived from IgG, IgA, IgD, IgE, IgM, or IgY, for example, IgG1, IgG2, IgG 3, or IgG4.

The antibody or antigen binding fragment may be chemically or recombinantly synthesized (not naturally occurring).

4-1BB Targeting Moiety

The anti-EGFR/anti-4-1BB bispecific antibody may comprise an anti-4-1BB antibody or an antigen-binding fragment thereof, as a 4-1BB targeting moiety.

The term "4-1BB", which is also called as CD137 or TNFRSF9 (TNF Receptor Superfamily Member 9), is a member of TNF-receptor superfamily (TNFRSF) and is a co-stimulatory molecule which is expressed following the activation of immune cells, both innate and adaptive immune cells. 4-1BB plays important role in modulate the activity of various immune cells. As used herein, 4-1BB may be originated from a mammal, for example, *Homo sapiens* (human) (NCBI Accession No. NP_001552.2). For example, the human 4-1BB protein (NP_001552.2) may be represented by the amino acid sequence (SEQ ID NO: 89), as follows:

```
  1 mgnscyniva tlllvlnfer trslqdpcsn cpagtfcdnn rnqicspcpp nsfssaggqr
 61 tcdicrqckg vfrtrkecss tsnaecdctp gfhclgagcs mceqdckqgq eltkkgckdc
121 cfgtfndqkr gicrpwtncs ldgksvlvng tkerdvvcgp spadlspgas svtppapare
181 pghspqiisf flaltstall fllffltlrf swkrgrkkl lyifkqpfmr pvqttqeedg
241 cscrfpeeee ggcel
```

In an embodiment, the anti-4-1BB antibody or an antigen-binding fragment thereof may comprise:
- a CDR (complementarity determining region)-H1 (H-CDR1) comprising an amino acid sequence of SEQ ID NO: 1, 2, or 3;
- an H-CDR2 comprising an amino acid sequence of SEQ ID NO: 4, 5, or 6;
- an H-CDR3 comprising an amino acid sequence of SEQ ID NO: 7, 8, 9, 10, or 11;
- an L-CDR1 comprising an amino acid sequence of SEQ ID NO: 12 or 13;
- an L-CDR2 comprising an amino acid sequence of SEQ ID NO: 14 or 15; and
- an L-CDR3 comprising an amino acid sequence of SEQ ID NO: 16 or 17.

The amino acid sequences of the CDRs of the anti-4-1BB antibody or an antigen-binding fragment are illustrated in Table 1:

TABLE 1

| SEQ ID NO | H-CDR1 | SEQ ID NO | H-CDR2 | SEQ ID NO | H-CDR3 |
|---|---|---|---|---|---|
| 1 | SYDMS | 4 | WISYSGGSIYYADSVKG | 7 | DGQRNSMREFDY |
| | | | | 8 | DAQRNSMREFDY |
| | | | | 9 | DAQRQSMREFDY |
| 2 | GYDMS | 5 | VIYPDDGNTYYADSVKG | 10 | HGGQKPTTKSSSAYGMDG |
| 3 | SYWMH | 6 | EINPGNGHTNYNEKFKS | 11 | SFTTARAFAY |

| SEQ ID NO | L-CDR1 | SEQ ID NO | L-CDR2 | SEQ ID NO | L-CDR3 |
|---|---|---|---|---|---|
| 12 | SGSSSNIGNNYVT | 14 | ADSHRPS | 16 | ATWDYSLSGYV |
| 13 | RASQTISDYLH | 15 | YASQSIS | 17 | QDGHSFPPT |

For example, the anti-4-1BB antibody or an antigen-binding fragment thereof may comprise:
- an H-CDR1 comprising an amino acid sequence of SEQ ID NO: 1, an H-CDR2 comprising an amino acid sequence of SEQ ID NO: 4, an H-CDR3 comprising an amino acid sequence of SEQ ID NO: 7, an L-CDR1 comprising an amino acid sequence of SEQ ID NO: 12, an L-CDR2 comprising an amino acid sequence of SEQ ID NO: 14, and an L-CDR3 comprising an amino acid sequence of SEQ ID NO: 16;
- an H-CDR1 comprising an amino acid sequence of SEQ ID NO: 1, an H-CDR2 comprising an amino acid sequence of SEQ ID NO: 4, an H-CDR3 comprising an amino acid sequence of SEQ ID NO: 8, an L-CDR1 comprising an amino acid sequence of SEQ ID NO: 12, an L-CDR2 comprising an amino acid sequence of SEQ ID NO: 14, and an L-CDR3 comprising an amino acid sequence of SEQ ID NO: 16;
- an H-CDR1 comprising an amino acid sequence of SEQ ID NO: 1, an H-CDR2 comprising an amino acid sequence of SEQ ID NO: 4, an H-CDR3 comprising an amino acid sequence of SEQ ID NO: 9, an L-CDR1 comprising an amino acid sequence of SEQ ID NO: 12, an L-CDR2 comprising an amino acid sequence of SEQ ID NO: 14, and an L-CDR3 comprising an amino acid sequence of SEQ ID NO: 16;
- an H-CDR1 comprising an amino acid sequence of SEQ ID NO: 1, an H-CDR2 comprising an amino acid sequence of SEQ ID NO: 4, an H-CDR3 comprising an amino acid sequence of SEQ ID NO: 7, an L-CDR1 comprising an amino acid sequence of SEQ ID NO: 13, an L-CDR2 comprising an amino acid sequence of SEQ ID NO: 15, and an L-CDR3 comprising an amino acid sequence of SEQ ID NO: 17;
- an H-CDR1 comprising an amino acid sequence of SEQ ID NO: 1, an H-CDR2 comprising an amino acid sequence of SEQ ID NO: 4, an H-CDR3 comprising an amino acid sequence of SEQ ID NO: 8, an L-CDR1 comprising an amino acid sequence of SEQ ID NO: 13, an L-CDR2 comprising an amino acid sequence of SEQ ID NO: 15, and an L-CDR3 comprising an amino acid sequence of SEQ ID NO: 17;
- an H-CDR1 comprising an amino acid sequence of SEQ ID NO: 1, an H-CDR2 comprising an amino acid sequence of SEQ ID NO: 4, an H-CDR3 comprising an amino acid sequence of SEQ ID NO: 9, an L-CDR1 comprising an amino acid sequence of SEQ ID NO: 13, an L-CDR2 comprising an amino acid sequence of SEQ ID NO: 15, and an L-CDR3 comprising an amino acid sequence of SEQ ID NO: 17;
- an H-CDR1 comprising an amino acid sequence of SEQ ID NO: 2, an H-CDR2 comprising an amino acid sequence of SEQ ID NO: 5, an H-CDR3 comprising an amino acid sequence of SEQ ID NO: 10, an L-CDR1 comprising an amino acid sequence of SEQ ID NO: 12, an L-CDR2 comprising an amino acid sequence of SEQ ID NO: 14, and an L-CDR3 comprising an amino acid sequence of SEQ ID NO: 16;
- an H-CDR1 comprising an amino acid sequence of SEQ ID NO: 2, an H-CDR2 comprising an amino acid sequence of SEQ ID NO: 5, an H-CDR3 comprising an amino acid sequence of SEQ ID NO: 10, an L-CDR1 comprising an amino acid sequence of SEQ ID NO: 13, an L-CDR2 comprising an amino acid sequence of SEQ ID NO: 15, and an L-CDR3 comprising an amino acid sequence of SEQ ID NO: 17;
- an H-CDR1 comprising an amino acid sequence of SEQ ID NO: 3, an H-CDR2 comprising an amino acid sequence of SEQ ID NO: 6, an H-CDR3 comprising an amino acid sequence of SEQ ID NO: 11, an L-CDR1 comprising an amino acid sequence of SEQ ID NO: 12, an L-CDR2 comprising an amino acid sequence of SEQ ID NO: 14, and an L-CDR3 comprising an amino acid sequence of SEQ ID NO: 16; or
- an H-CDR1 comprising an amino acid sequence of SEQ ID NO: 3, an H-CDR2 comprising an amino acid sequence of SEQ ID NO: 6, an H-CDR3 comprising an amino acid sequence of SEQ ID NO: 11, an L-CDR1 comprising an amino acid sequence of SEQ ID NO: 13, an L-CDR2 comprising an amino acid sequence of SEQ ID NO: 15, and an L-CDR3 comprising an amino acid sequence of SEQ ID NO: 17.

In another embodiment, the anti-4-1BB antibody or antigen-binding fragment thereof may comprise a heavy chain variable region comprising an H-CDR1 comprising an amino acid sequence of SEQ ID NO: 1, 2, or 3, an H-CDR2 comprising an amino acid sequence of SEQ ID NO: 4, 5, or 6, and an H-CDR3 comprising an amino acid sequence of SEQ ID NO: 7, 8, 9, 10, or 11; and a light chain variable region comprising an L-CDR1 comprising an amino acid sequence of SEQ ID NO: 12, or 13, an L-CDR2 comprising an amino acid sequence of SEQ ID NO: 14, or 15, and an L-CDR3 comprising an amino acid sequence of SEQ ID NO: 16, or 17.

In another embodiment, the anti-4-1BB antibody or antigen-binding fragment thereof may comprise a heavy chain variable region comprising an amino acid sequence of SEQ ID NO: 18, 19, 20, 21, 22, 23, 24, 25, 26, 27, 28, or 29; and a light chain variable region comprising or consisting essentially of an amino acid sequence of SEQ ID NO: 30, 31, 32, 33, 34, or 88.

The amino acid sequences of the variable regions of the anti-4-1BB antibody or an antigen-binding fragment are illustrated in Table 2:

TABLE 2

| SEQ ID NO | Heavy chain variable region targeting 4-1BB |
|---|---|
| 18 | EVQLLESGGGLVQPGGSLRLSCAASGFTFSSYDMSWVRQAPGKGLEWVSWISYSGGSIYYADSVKGRFTISRDNSKNTLYLQMNSLRAEDTAVYYCARDGQRNSMREFDYWGQGTLVTVSS |
| 19 | EVQLLESGGGLVQPGGSLRLSCAASGFTFSSYDMSWVRQAPGKGLEWVSWISYSGGSIYYADSVKGRFTISRDNSKNTLYLQMNSLRAEDTAVYYCARDAQRNSMREFDYWGQGTLVTVSS |
| 20 | EVQLLESGGGLVQPGGSLRLSCAASGFTFSSYDMSWVRQAPGKGLEWVSWISYSGGSIYYADSVKGRFTISRDNSKNTLYLQMNSLRAEDTAVYYCARDAQRQSMREFDYWGQGTLVTVSS |
| 21 | EVQLLESGGGLVQPGGSLRLSCAASGFTFSGYDMSWVRQAPGKGLEWVSVIYPDDGNTYYADSVKGRFTISRDNSKNTLYLQMNSLRAEDAAVYYCAKHGGQKPTTKSSSAYGMDGWGQGTLVTVSS |
| 22 | EVQLLESGGGLVQPGGSLRLSCAASGFTFSGYDMSWVRQAPGKGLEWVSVIYPDDGNTYYADSVKGRFTISRDNSKNTLYLQMNSLRAEDTAVYYCAKHGGQKPTTKSSSAYGMDGWGQGTLVTVSS |
| 23 | QVQLQQSGAEVIKPGASVKLSCKASGYTFSSYWMHWVRQAPGQGLEWIGEINPGNGHTNYNEKFKSRATLTGDTSTSTVYMELSSLRSEDTAVYYCARSFTTARAFAYWGQGTLVTVSS |
| 24 | EVQLLESGGGLVQPGGSLRLSCAASGFTFSSYDMSWVRQAPGKCLEWVSWISYSGGSIYYADSVKGRFTISRDNSKNTLYLQMNSLRAEDTAVYYCARDGQRNSMREFDYWGQGTLVTVSS |
| 25 | EVQLLESGGGLVQPGGSLRLSCAASGFTFSSYDMSWVRQAPGKCLEWVSWISYSGGSIYYADSVKGRFTISRDNSKNTLYLQMNSLRAEDTAVYYCARDAQRNSMREFDYWGQGTLVTVSS |
| 26 | EVQLLESGGGLVQPGGSLRLSCAASGFTFSSYDMSWVRQAPGKCLEWVSWISYSGGSIYYADSVKGRFTISRDNSKNTLYLQMNSLRAEDTAVYYCARDAQRQSMREFDYWGQGTLVTVSS |
| 27 | EVQLLESGGGLVQPGGSLRLSCAASGFTFSGYDMSWVRQAPGKCLEWVSVIYPDDGNTYYADSVKGRFTISRDNSKNTLYLQMNSLRAEDAAVYYCAKHGGQKPTTKSSSAYGMDGWGQGTLVTVSS |
| 28 | EVQLLESGGGLVQPGGSLRLSCAASGFTFSGYDMSWVRQAPGKCLEWVSVIYPDDGNTYYADSVKGRFTISRDNSKNTLYLQMNSLRAEDTAVYYCAKHGGQKPTTKSSSAYGMDGWGQGTLVTVSS |
| 29 | QVQLQQSGAEVIKPGASVKLSCKASGYTFSSYWMHWVRQAPGQCLEWIGEINPGNGHTNYNEKFKSRATLTGDTSTSTVYMELSSLRSEDTAVYYCARSFTTARAFAYWGQGTLVTVSS |

| SEQ ID NO | Light chain variable region targeting 4-1BB |
|---|---|
| 30 | QSVLTQPPSASGTPGRRVTISCSGSSSNIGNNYVTWYQQLPGTAPKLLIYADSHRPSGVPDRFSGSKSGTSASLAISGLRSEDEADYYCATWDYSLSGYVFGGGTKLTVL |
| 31 | QSVLTQPPSASGTPGQRVTISCSGSSSNIGNNYVTWYQQLPGTAPKLLIYADSHRPSGVPDRFSGSKSGTSASLAISGLRSEDEADYYCATWDYSLSGYVFGGGTKLTVL |
| 32 | DIVMTQSPAFLSVTPGEKVTITCRASQTISDYLHWYQQKPDQAPKLLIKYASQSISGIPSRFSGSGSGTDFTFTISSLEAEDAATYYCQDGHSFPPTFGQGTKLEIKR |
| 33 | QSVLTQPPSASGTPGRRVTISCSGSSSNIGNNYVTWYQQLPGTAPKLLIYADSHRPSGVPDRFSGSKSGTSASLAISGLRSEDEADYYCATWDYSLSGYVFGCGTKLTVL |
| 34 | QSVLTQPPSASGTPGQRVTISCSGSSSNIGNNYVTWYQQLPGTAPKLLIYADSHRPSGVPDRFSGSKSGTSASLAISGLRSEDEADYYCATWDYSLSGYVFGCGTKLTVL |
| 88 | DIVMTQSPAFLSVTPGEKVTITCRASQTISDYLHWYQQKPDQAPKLLIKYASQSISGIPSRFSGSGSGTDFTFTISSLEAEDAATYYCQDGHSFPPTFGCGTKLEIKR |

For example, the anti-4-1BB antibody or an antigen-binding fragment thereof may comprise:

a heavy chain variable region comprising an comprising an amino acid sequence of SEQ ID NO: 18, 19, 20, 21, 22, 23, 24, 25, 26, 27, 28, or 29, and a light chain variable region comprising an amino acid sequence of SEQ ID NO: 30;

a heavy chain variable region comprising an comprising an amino acid sequence of SEQ ID NO: 18, 19, 20, 21, 22, 23, 24, 25, 26, 27, 28, or 29, and a light chain variable region comprising an amino acid sequence of SEQ ID NO: 31;

a heavy chain variable region comprising an comprising an amino acid sequence of SEQ ID NO: 18, 19, 20, 21, 22, 23, 24, 25, 26, 27, 28, or 29, and a light chain variable region comprising an amino acid sequence of SEQ ID NO: 32;

a heavy chain variable region comprising an comprising an amino acid sequence of SEQ ID NO: 18, 19, 20, 21, 22, 23, 24, 25, 26, 27, 28, or 29, and a light chain variable region comprising an amino acid sequence of SEQ ID NO: 33;

a heavy chain variable region comprising an comprising an amino acid sequence of SEQ ID NO: 18, 19, 20, 21, 22, 23, 24, 25, 26, 27, 28, or 29, and a light chain variable region comprising an amino acid sequence of SEQ ID NO: 34; or a heavy chain variable region comprising an comprising an amino acid sequence of SEQ ID NO: 18, 19, 20, 21, 22, 23, 24, 25, 26, 27, 28, or 29, and a light chain variable region comprising an amino acid sequence of SEQ ID NO: 88.

The amino acid sequences of frameworks of the variable regions of the anti-4-1BB antibody or an antigen-binding fragment are illustrated in Table 3:

TABLE 3

| SEQ ID NO | H-FR1 | SEQ ID NO | H-FR2 | SEQ ID NO | H-FR3 | SEQ ID NO | H-FR4 |
|---|---|---|---|---|---|---|---|
| 35 | EVQLLESGGGLVQPGGSLRLSCAASGFTFS | 37 | WVRQAPGKGLEWVS | 41 | RFTISRDNSKNTLYLQMNSLRAEDTAVYYCAR | 45 | WGQGTLVTVSS |

TABLE 3-continued

| | | | | | | | |
|---|---|---|---|---|---|---|---|
| 35 | EVQLLESGG GLVQPGGSL RLSCAASGF TFS | 37 | WVRQAP GKGLEWV S | 42 | RFTISRDNS KNTLYLQMN SLRAEDAAV YYCAK | 45 | WGQGT LVTVSS |
| 35 | EVQLLESGG GLVQPGGSL RLSCAASGF TFS | 37 | WVRQAP GKGLEWV S | 43 | RFTISRDNS KNTLYLQMN SLRAEDTAV YYCAK | 45 | WGQGT LVTVSS |
| 36 | QVQLQQSG AEVIKPGAS VKLSCKASG YTFS | 38 | WVRQAP GQGLEWI G | 44 | RATLTGDTS TSTVYMELS SLRSEDTAV YYCAR | 45 | WGQGT LVTVSS |
| 35 | EVQLLESGG GLVQPGGSL RLSCAASGF TFS | 39 | WVRQAP GKCLEWV S | 41 | RFTISRDNS KNTLYLQMN SLRAEDTAV YYCAR | 45 | WGQGT LVTVSS |
| 35 | EVQLLESGG GLVQPGGSL RLSCAASGF TFS | 39 | WVRQAP GKCLEWV S | 42 | RFTISRDNS KNTLYLQMN SLRAEDAAV YYCAK | 45 | WGQGT LVTVSS |
| 35 | EVQLLESGG GLVQPGGSL RLSCAASGF TFS | 39 | WVRQAP GKCLEWV S | 43 | RFTISRDNS KNTLYLQMN SLRAEDTAV YYCAK | 45 | WGQGT LVTVSS |
| 36 | QVQLQQSG AEVIKPGAS VKLSCKASG YTFS | 40 | WVRQAP GQCLEWI G | 44 | RATLTGDTS TSTVYMELS SLRSEDTAV YYCAR | 45 | WGQGT LVTVSS |

| SEQ ID NO | L-FR1 | SEQ ID NO | L-FR2 | SEQ ID NO | L-FR3 | SEQ ID NO | L-FR4 |
|---|---|---|---|---|---|---|---|
| 46 | QSVLTQPPS ASGTPGRR VTISC | 49 | WYQQLP GTAPKLLI Y | 51 | GVPDRFSG SKSGTSASL AISGLRSED EADYYC | 53 | FGGGT KLTVL |
| 47 | QSVLTQPPS ASGTPGQR VTISC | 49 | WYQQLP GTAPKLLI Y | 51 | GVPDRFSG SKSGTSASL AISGLRSED EADYYC | 53 | FGGGT KLTVL |
| 48 | DIVMTQSPA FLSVTPGEK VTITC | 50 | WYQQKP DQAPKLLI K | 52 | GIPSRFSGS GSGTDFTFT ISSLEAEDAA TYYC | 54 | FGQGT KLEIKR |
| 46 | QSVLTQPPS ASGTPGRR VTISC | 49 | WYQQLP GTAPKLLI Y | 51 | GVPDRFSG SKSGTSASL AISGLRSED EADYYC | 55 | FGCGT KLTVL |
| 47 | QSVLTQPPS ASGTPGQR VTISC | 49 | WYQQLP GTAPKLLI Y | 51 | GVPDRFSG SKSGTSASL AISGLRSED EADYYC | 55 | FGCGT KLTVL |

In another embodiment, the anti-4-1BB antibody or antigen-binding fragment thereof may comprise a heavy chain comprising or consisting essentially of an amino acid sequence of SEQ ID NO: 56, 57, 58, 59, 60, or 61; and a light chain comprising or consisting essentially of an amino acid sequence of SEQ ID NO: 62, 63, or 64.

For example, the anti-4-1BB antibody or an antigen-binding fragment thereof may comprise:
  a heavy chain comprising or consisting essentially of an amino acid sequence of SEQ ID NO: 56, 57, 58, 59, 60, or 61; and a light chain comprising or consisting essentially of an amino acid sequence of SEQ ID NO: 62;
  a heavy chain comprising or consisting essentially of an amino acid sequence of SEQ ID NO: 56, 57, 58, 59, 60, or 61; and a light chain comprising or consisting essentially of an amino acid sequence of SEQ ID NO: 63; or
  a heavy chain comprising or consisting essentially of an amino acid sequence of SEQ ID NO: 56, 57, 58, 59, 60, or 61; and a light chain comprising or consisting essentially of an amino acid sequence of SEQ ID NO: 64.

In another embodiment, the anti-4-1BB antibody or antigen-binding fragment thereof may be a scFv (single chain variable fragment), comprising:
  a heavy chain variable region comprising an H-CDR1 comprising an amino acid sequence of SEQ ID NO: 1, 2, or 3, an H-CDR2 comprising an amino acid sequence of SEQ ID NO: 4, 5, or 6, and an H-CDR3 comprising an amino acid sequence of SEQ ID NO: 7, 8, 9, 10, or 11; and
  a light chain variable region comprising an L-CDR1 comprising an amino acid sequence of SEQ ID NO: 12, or 13, an L-CDR2 comprising an amino acid sequence of SEQ ID NO: 14, or 15, and an L-CDR3 comprising an amino acid sequence of SEQ ID NO: 16, or 17,
  wherein the heavy chain variable region and the light chain variable region may be linked to each other in any order directly (i.e., without a linker) or via a peptide linker.

For example, the anti-4-1BB scFv may comprise:
  a heavy chain variable region comprising an amino acid sequence of SEQ ID NO: 18, 19, 20, 21, 22, 23, 24, 25, 26, 27, 28, or 29; and
  a light chain variable region comprising or consisting essentially of an amino acid sequence of SEQ ID NO: 30, 31, 32, 33, 34 or 88,
  wherein the heavy chain variable region and the light chain variable region may be linked to each other in any order directly or via a peptide linker.

For example, the anti-4-1BB scFv may comprise:
  a heavy chain variable region comprising or consisting essentially of an amino acid sequence of SEQ ID NO: 24, 25, 26, 27, 28, or 29; and a light chain variable region comprising or consisting essentially of an amino acid sequence of SEQ ID NO: 33;
  a heavy chain variable region comprising or consisting essentially of an amino acid sequence of SEQ ID NO: 24, 25, 26, 27, 28, or 29; and a light chain variable region comprising or consisting essentially of an amino acid sequence of SEQ ID NO: 34; or
  a heavy chain variable region comprising an comprising an amino acid sequence of SEQ ID NO: 24, 25, 26, 27, 28, or 29, and a light chain variable region comprising an amino acid sequence of SEQ ID NO: 88,
  wherein the heavy chain variable region and the light chain variable region may be linked to each other in any order directly or via a peptide linker.

In the present disclosure, the anti-4-1BB scFv comprise a heavy chain variable region and a light chain variable region, in any order. For example, the anti-4-1BB scFv may comprise a light chain variable region and a heavy chain variable region, in a direction from N-terminus to C-terminus. Alternatively, the anti-4-1BB scFv may comprise a heavy chain variable region and a light chain variable region, in a direction from N-terminus to C-terminus.

EGFR Targeting Moiety

The anti-EGFR/anti-4-1BB bispecific antibody may comprise an anti-EGFR antibody or an antigen-binding fragment thereof as an EGFR targeting moiety.

The "EGFR (Epidermal Growth Factor Receptor; also called as ErbB-1, or HER1 in humans)" is a transmembrane protein that is a receptor for members of the epidermal growth factor family (EGF family) of extracellular protein ligands. The epidermal growth factor receptor is a member of the ErbB family of receptors, a subfamily of four closely related receptor tyrosine kinases: EGFR (ErbB-1), HER2/neu (ErbB-2), Her 3 (ErbB-3) and Her 4 (ErbB-4). In many cancer types, mutations affecting EGFR expression or activity could result in cancer. For instance, the EGFR proteins may be polypeptides deposited under GenBank Accession Number NP_001333826.1, NP_001333827.1, etc., which are encoded by the nucleotide sequences (mRNA) deposited under GenBank Accession Number NM_001346897.2, NM_001346898.2, etc., respectively.

In one embodiment, the anti-EGFR antibody may be cetuximab. The antigen binding region of the anti-EGFR antibody recognizing EGFR as an antigen may be scFv, (scFv)$_2$, Fab, Fab' or F(ab')$_2$ of an anti-EGFR antibody, cetuximab.

The anti-EGFR antibody or an antigen-binding fragment thereof may be an anti-EGFR antibody or an antigen-binding fragment thereof comprising 6 CDRs of Cetuximab.

In an embodiment, the anti-EGFR antibody or antigen-binding fragment (e.g., scFv, (scFv)$_2$, Fab, Fab' or F(ab')$_2$) of the anti-EGFR antibody may be cetuximab or an antigen-binding fragment thereof, or a variant thereof.

For example, the anti-EGFR antibody or antigen-binding fragment thereof may comprise:
- an H-CDR1 comprising an amino acid sequence of SEQ ID NO: 65;
- an H-CDR2 comprising an amino acid sequence of SEQ ID NO: 66;
- an H-CDR3 comprising an amino acid sequence of SEQ ID NO: 67;
- an L-CDR1 comprising an amino acid sequence of SEQ ID NO: 68;
- an L-CDR2 comprising an amino acid sequence of SEQ ID NO: 69; and
- an L-CDR3 comprising an amino acid sequence of SEQ ID NO: 70.

The amino acid sequences of the CDRs of the anti-EGFR antibody or an antigen-binding fragment are illustrated in Table 4:

TABLE 4

| SEQ ID NO | H-CDR1 | SEQ ID NO | H-CDR2 | SEQ ID NO | H-CDR3 |
|---|---|---|---|---|---|
| 65 | NYGVH | 66 | VIWSGGNTDYNTPFTS | 67 | ALTYYDYEFAY |

| SEQ ID NO | L-CDR1L-CDR | SEQ ID NO | L-CDR2L-CDR | SEQ ID NO | L-CDR3L-CDR |
|---|---|---|---|---|---|
| 68 | RASQSIGTNIH | 69 | YASESIS | 70 | QQNNNWPTT |

In another embodiment, the anti-EGFR antibody or antigen-binding fragment thereof may comprise a heavy chain variable region comprising an H-CDR1 comprising an amino acid sequence of SEQ ID NO: 65, an H-CDR2 comprising an amino acid sequence of SEQ ID NO: 66, and an H-CDR3 comprising an amino acid sequence of SEQ ID NO: 67; and a light chain variable region comprising an L-CDR1 comprising an amino acid sequence of SEQ ID NO: 68, an L-CDR2 comprising an amino acid sequence of SEQ ID NO: 69, and an L-CDR3 comprising an amino acid sequence of SEQ ID NO: 70.

In another embodiment, the anti-EGFR antibody or antigen-binding fragment thereof may comprise a heavy chain variable region comprising or consisting essentially of an amino acid sequence of SEQ ID NO: 71, and a light chain variable region comprising or consisting essentially of an amino acid sequence of SEQ ID NO: 72.

The amino acid sequences of the variable regions of the anti-EGFR antibody or an antigen-binding fragment are illustrated in Table 5:

TABLE 5

| SEQ ID NO | Heavy chain variable region targeting EGFR |
|---|---|
| 71 | QVQLKQSGPGLVQPSQSLSITCTVSGFSLTNYGVHWVRQSPGKG LEWLGVIWSGGNTDYNTPFTSRLSINKDNSKSQVFFKMNSLQSN DTAIYYCARALTYYDYEFAYWGQGTLVTVS |

| SEQ ID NO | Light chain variable region targeting EGFR |
|---|---|
| 72 | DILLTQSPVILSVSPGERVSFSCRASQSIGTNIHWYQQRTNGSP RLLIKYASESISGIPSRFSGSGSGTDFTLSINSVESEDIADYYC QQNNNWPTTFGAGTKLELKR |

In another embodiment, the anti-EGFR antibody or antigen-binding fragment thereof may comprise a heavy chain comprising or consisting essentially of an amino acid sequence of SEQ ID NO: 73, or 74; and a light chain comprising or consisting essentially of an amino acid sequence of SEQ ID NO: 75.

In another embodiment, the anti-EGFR antibody or antigen-binding fragment thereof may be a scFv (single chain variable fragment), comprising:
- a heavy chain variable region comprising an H-CDR1 comprising an amino acid sequence of SEQ ID NO: 65, an H-CDR2 comprising an amino acid sequence of SEQ ID NO: 66, and an H-CDR3 comprising an amino acid sequence of SEQ ID NO: 67; and
- a light chain variable region comprising an L-CDR1 comprising an amino acid sequence of SEQ ID NO: 68, an L-CDR2 comprising an amino acid sequence of SEQ ID NO: 69, and an L-CDR3 comprising an amino acid sequence of SEQ ID NO: 70,
- wherein the heavy chain variable region and the light chain variable region may be linked to each other in any order directly (i.e., without a linker) or via a peptide linker.

In another embodiment, the anti-EGFR antibody or antigen-binding fragment thereof may be a scFv (single chain variable fragment), comprising:
- a heavy chain variable region comprising or consisting essentially of an amino acid sequence of SEQ ID NO: 71; and
- a light chain variable region comprising or consisting essentially of an amino acid sequence of SEQ ID NO: 72,
- wherein the heavy chain variable region and the light chain variable region may be linked to each other in any order directly or via a peptide linker.

In the present disclosure, the anti-EGFR scFv comprise a heavy chain variable region and a light chain variable region, in any order. For example, the anti-EGFR scFv may comprise a light chain variable region and a heavy chain variable region, in a direction from N-terminus to C-terminus. Alternatively, the anti-EGFR scFv may comprise a heavy chain variable region and a light chain variable region, in a direction from N-terminus to C-terminus.

Bispecific Antibody

The present disclosure provides an anti-EGFR/anti-4-1BB bispecific antibody comprising:
(1) an anti-EGFR antibody or an antigen-binding fragment thereof, as an EGFR targeting moiety, which is capable of specifically recognizing and/or binding to EGFR protein, and
(2) an anti-4-1BB antibody or an antigen-binding fragment thereof, as a 4-1BB targeting moiety, which is capable of specifically recognizing and/or binding to 4-1BB protein.

The anti-EGFR/anti-4-1BB bispecific antibody may activate 4-1BB signaling only when crosslinked by EGFR-expressing tumor cells. In addition, the anti-4-1BB antibody or an antigen-binding fragment thereof contained in the bispecific antibody may be characterized by localizing and/or activating only in tumor microenvironment (TME), and/or considerably reducing liver toxicities compared to pre-existing anti-4-1BB antibodies, with maintaining the efficacies of immune response enhancement and/or tumor treatment.

In an embodiment, the bispecific antibody may comprise a full-length anti-EGFR antibody and an antigen-binding fragment (e.g., scFv) of an anti-4-1BB antibody, wherein the antigen-binding fragment of an anti-4-1BB antibody may be linked to N-terminus, C-terminus, or both thereof of a full-length anti-EGFR antibody, directly or via a peptide linker. In another embodiment, the bispecific antibody may comprise a full-length anti-4-1BB antibody and an antigen-binding fragment (e.g., scFv) of an anti-EGFR antibody, wherein the antigen-binding fragment of an anti-EGFR antibody may be linked to N-terminus, C-terminus, or both thereof of a full-length anti-4-1BB antibody, directly or via a peptide linker.

In an embodiment, the scFv contained in the bispecific antibody may comprise a heavy chain variable region and a light chain variable region in any order. For example, the scFv contained in the bispecific antibody may comprise a light chain variable region and a heavy chain variable region, in a direction from N-terminus to C-terminus, and optionally a peptide linker therebetween, or alternatively, the scFv contained in the bispecific antibody may comprise a heavy chain variable region and a light chain variable region, in a direction from N-terminus to C-terminus, and optionally a peptide linker therebetween.

When the bispecific antibody comprises a full-length anti-EGFR antibody and an anti-4-1BB scFv, the bispecific antibody may comprise:
(i) a first polypeptide comprising, in a direction from N-terminus to C-terminus:
a heavy chain of an anti-EGFR antibody,
optionally, a peptide linker (a first peptide linker), and
an anti-4-1BB scFv; and
(ii) a second polypeptide comprising a light chain of the anti-EGFR antibody,
wherein the anti-4-1BB scFv may comprise, in a direction from N-terminus to C-terminus:
a light chain variable region of an anti-4-1BB antibody,
optionally, a peptide linker (a second peptide linker), and
a heavy chain variable region of the anti-4-1BB antibody.
Alternatively, the bispecific antibody may comprise:
(i) a first polypeptide comprising, in a direction from N-terminus to C-terminus:
an anti-4-1BB scFv,
optionally, a peptide linker (a first peptide linker), and
a heavy chain of an anti-EGFR antibody; and
(ii) a second polypeptide comprising a light chain of the anti-EGFR antibody,
wherein the anti-4-1BB scFv may comprise, in a direction from N-terminus to C-terminus:
a light chain variable region of an anti-4-1BB antibody,
optionally, a peptide linker (a second peptide linker), and
a heavy chain variable region of the anti-4-1BB antibody.
Alternatively, the bispecific antibody may comprise:
(i) a first polypeptide comprising, in a direction from N-terminus to C-terminus:
a heavy chain of an anti-EGFR antibody,
optionally, a peptide linker (a first peptide linker), and
an anti-4-1BB scFv; and
(ii) a second polypeptide comprising a light chain of the anti-EGFR antibody,
wherein the anti-4-1BB scFv may comprise, in a direction from N-terminus to C-terminus:
a heavy chain variable region of the anti-4-1BB antibody,
optionally, a peptide linker (a second peptide linker), and
a light chain variable region of an anti-4-1BB antibody.
Alternatively, the bispecific antibody may comprise:
(i) a first polypeptide comprising, in a direction from N-terminus to C-terminus:
an anti-4-1BB scFv,
optionally, a peptide linker (a first peptide linker), and
a heavy chain of an anti-EGFR antibody; and
(ii) a second polypeptide comprising a light chain of the anti-EGFR antibody,
wherein the anti-4-1BB scFv may comprise, in a direction from N-terminus to C-terminus:
a heavy chain variable region of the anti-4-1BB antibody,
optionally, a peptide linker (a second peptide linker), and
a light chain variable region of an anti-4-1BB antibody.

When the bispecific antibody comprises a full-length anti-4-1BB antibody and an anti-EGFR scFv, the bispecific antibody may comprise:
(i) a first polypeptide comprising, in a direction from N-terminus to C-terminus:
a heavy chain of an anti-4-1BB antibody,
optionally, a peptide linker (a first peptide linker), and
an anti-EGFR scFv; and
(ii) a second polypeptide comprising a light chain of the anti-4-1BB antibody,
wherein the anti-EGFR scFv may comprise, in a direction from N-terminus to C-terminus:
a light chain variable region of an anti-EGFR antibody,
optionally, a peptide linker (a second peptide linker), and
a heavy chain variable region of the anti-EGFR antibody.
Alternatively, the bispecific antibody may comprise:
(i) a first polypeptide comprising, in a direction from N-terminus to C-terminus:
an anti-EGFR scFv,
optionally, a peptide linker (a first peptide linker), and
a heavy chain of an anti-4-1BB antibody; and
(ii) a second polypeptide comprising a light chain of the anti-4-1BB antibody, wherein the anti-EGFR scFv may comprise, in a direction from N-terminus to C-terminus:
a light chain variable region of an anti-EGFR antibody,
optionally, a peptide linker (a second peptide linker), and
a heavy chain variable region of the anti-EGFR antibody.
Alternatively, the bispecific antibody may comprise:
(i) a first polypeptide comprising, in a direction from N-terminus to C-terminus:
a heavy chain of an a anti-4-1BB antibody,
optionally, a peptide linker (a first peptide linker), and
an anti-EGFR scFv; and
(ii) a second polypeptide comprising a light chain of the anti-4-1BB antibody,
wherein the anti-EGFR scFv may comprise, in a direction from N-terminus to C-terminus:
a heavy chain variable region of the anti-EGFR antibody,
optionally, a peptide linker (a second peptide linker), and
a light chain variable region of an anti-EGFR antibody.
Alternatively, the bispecific antibody may comprise:
(i) a first polypeptide comprising, in a direction from N-terminus to C-terminus:
an anti-EGFR scFv,
optionally, a peptide linker (a first peptide linker), and
a heavy chain of an anti-4-1BB antibody; and
(ii) a second polypeptide comprising a light chain of the anti-4-1BB antibody,
wherein the anti-EGFR scFv may comprise, in a direction from N-terminus to C-terminus:
a heavy chain variable region of the anti-EGFR antibody,
optionally, a peptide linker (a second peptide linker), and
a light chain variable region of an anti-EGFR antibody.

The first peptide linker and the second peptide linker may be, independently, present or absent in the bispecific antibody, and the same with or different from each other.

In another embodiment, both of the EGFR targeting moiety and the 4-1BB targeting moiety contained in the bispecific antibody may be a full-length antibody or an antigen-binding fragment comprising heavy chain CDRs, light chain CDRs, or a combination thereof, which are linked to each other directly or via a peptide linker.

Given that each of antibodies can bind to both of 4-1BB (such as, human 4-1BB) and EGFR (such as, human EGFR), the CDR sequences, or $V_H$ (heavy chain variable region) and $V_L$ (light chain variable region) sequences as disclosed herein can be "mixed and matched" to create other anti-EGFR/anti-4-1BB binding bispecific molecules.

Peptide Linker

For high purity of the antibody, the bispecific antibody may comprise a peptide linker between a heavy chain and scFv in a first polypeptide (a first peptide linker), and/or between heavy and light variable regions in scFv (a second peptide linker).

As used herein, the term "peptide linker" may refer to an oligopeptide including 1 to 100 amino acids, particularly 2 to 50 amino acids, each of which may be any kind of amino acids without any restrictions. Any conventional peptide linker may be used with or without an appropriate modification to comply with specific purposes. In a specific embodiment, the peptide linker may comprise, for example, Gly, Asn and/or Ser residues, and/or comprise neutral amino acids such as Thr and/or Ala. The amino acid sequences suitable for the peptide linker may be known in the relevant art. The length of the peptide linker can be properly determined within such a limit that the functions of the polypeptide and/or scFv will not be affected. For instance, the peptide linker may be formed by including a total of about 1 to about 100 amino acids, about 2 to about 50 amino acids, or about 5 to about 25 (e.g., 1, 2, 3, 4, 5, 6, 7, 8, 9, 10, 11, 12, 13, 14, 15, 16, 17, 18, 19, 20, 21, 22, 23, 24, or 25) amino acids, each of which is independently selected from the group consisting of Gly, Asn, Ser, Thr, and Ala. In one embodiment, the peptide linker may be represented as $(G_mS_l)_n$ (m, l, and n are the number of "G", "S", and "$(G_mS_l)$", respectively, and independently selected from integers of about 1 to about 10, particularly, 1, 2, 3, 4, 5, 6, 7, 8, 9, or 10). In one embodiment, the peptide linker can be amino acids of (GGGGS)2 (SEQ ID NO: 91), (GGGGS)3 (SEQ ID NO: 85), (GGGGS)4 (SEQ ID NO: 87), or (GS)9 (SEQ ID NO: 86), but not be limited thereto.

Medical Use

Provided is a medical use of the bispecific antibody for enhancing immune response, and/or treating and/or preventing a cancer.

More specifically, an embodiment provides a pharmaceutical composition comprising the bispecific antibody as an active ingredient. The pharmaceutical composition may further comprise a pharmaceutically acceptable carrier. The pharmaceutical composition may be used for enhancing immune response, and/or for treating and/or preventing a cancer.

Another embodiment provides a pharmaceutical composition for treating and/or preventing a cancer, the composition comprising the bispecific antibody as an active ingredient.

Another embodiment provides a method of treating and/or preventing a cancer in a subject in need thereof, comprising administering to the subject a pharmaceutically effective amount of the bispecific antibody or the pharmaceutical composition. The method may further step of identifying the subject in need of treating and/or preventing a cancer, prior to the administering step.

Another embodiment provides a use of the bispecific antibody or the pharmaceutical composition in treating and/or preventing a cancer. Another embodiment provides a use of the bispecific antibody in preparing a medicament for treating and/or preventing a cancer.

In some embodiment, the cancer may be characterized by EGFR expression or EGFR overexpression (compared to normal).

Another embodiment provides a pharmaceutical composition for enhancing immune response, the composition comprising the bispecific antibody as an active ingredient.

Another embodiment provides a method of enhancing immune response in a subject in need thereof, comprising administering to the subject a pharmaceutically effective amount of the bispecific antibody or the pharmaceutical composition to the subject. The method may further comprise a step of identifying the subject in need of enhancing immune response, prior to the administering step.

Another embodiment provides a use of the bispecific antibody or the pharmaceutical composition in enhancing immune response. Another embodiment provides a use of the bispecific antibody in preparing a medicament for enhancing immune response.

In some embodiment, the bispecific antibody or the pharmaceutical composition may enhance immune response with the proviso of the presence of EGFR. For example, in the method of enhancing immune response, the subject may have an EGFR-expressing or EGFR-overexpressing cell (e.g., an EGFR-expressing or EGFR-overexpressing cancer cell).

The cancer to be prevented and/or treated by the bispecific antibody or the pharmaceutical composition may be associated with 4-1BB and/or EGFR, especially, EGFR-expressed or EGFR-overexpressed cancer. The cancer may be selected from solid cancers and blood cancers. The cancer may be, but not limited to, one or more selected from the group consisting of breast cancer, colon cancer, gastric cancer, lung cancer (e.g., squamous cell carcinoma of the lung, small-cell lung cancer, non-small-cell lung cancer, adenocarcinoma of the lung), peritoneal carcinoma, skin cancer, squamous cell carcinoma, melanoma in the skin or eyeball, rectal cancer, cancer near the anus, esophagus cancer, small intestinal tumor, endocrine gland cancer, parathyroid cancer, adrenal cancer, soft-tissue sarcoma, urethral cancer, chronic or acute leukemia, lymphocytic lymphoma, hepatoma, gastrointestinal cancer, pancreatic cancer, glioblastoma, cervical cancer, ovarian cancer, liver cancer, bladder cancer, hepatocellular adenoma, large intestine cancer, endometrial carcinoma or uterine carcinoma, salivary gland tumor, kidney cancer, cervix cancer, prostate cancer, vulvar cancer, thyroid cancer, head and neck cancer, brain cancer, biliary tract cancer, gallbladder cancer, and the like. The cancer may be a primary cancer or a metastatic cancer.

As used herein, the term "prevention and/or treatment of cancer" may refer to cancer cell death, inhibition of cancer cell proliferation, alleviation of symptoms associated with cancer, inhibition of metastasis of cancer, etc.

As used herein, the term "enhancement of immune response" may refer to 4-1BB signal activation, enhancement in any immune response associated with 4-1BB, such as 4-1BB-induced signal activation (e.g., 4-1BB-induced NF-kB signal activation, increase in release of cytokine, target cell killing by immune cell, such as T cell, and the like, but not be limited thereto. In some embodiment, the enhancement of immune response by the bispecific antibody provided by this disclosure may occur be in the presence of EGFR.

The pharmaceutical composition may further comprise a pharmaceutically acceptable carrier, diluent, and/or excipient, in addition to the bispecific antibody as an active ingredient. The pharmaceutically acceptable carrier, diluent, and/or excipient may be anyone selected from those commonly used for the formulation of antibodies. For example, the pharmaceutically acceptable carrier may be one or more selected from the group consisting of lactose, dextrose, sucrose, sorbitol, mannitol, starch, gum acacia, calcium phosphate, alginates, gelatin, calcium silicate, micro-crystalline cellulose, polyvinylpyrrolidone, cellulose, water, syrup, methyl cellulose, methylhydroxy benzoate, propylhydroxy benzoate, talc, magnesium stearate, and mineral oil, but are not limited thereto.

The pharmaceutical composition may further comprise one or more selected from the group consisting of a lubricant, a wetting agent, a sweetener, a flavor enhancer, an emulsifying agent, a suspension agent, preservative, and the like.

The bispecific antibody or the pharmaceutical composition may be administered to the subject orally or parenterally. The parenteral administration may be intravenous injection, subcutaneous injection, muscular injection, intraperitoneal injection, endothelial administration, local administration, intranasal administration, intrapulmonary administration, or rectal administration. Since oral administration leads to digestion of proteins or peptides, an active ingredient in the compositions for oral administration must be coated or formulated to prevent digestion in stomach. In addition, the compositions may be administered using an optional device that enables the active ingredient to be delivered to target cells (e.g., cancer cells).

As used herein, the term "the pharmaceutically effective amount" may refer to an amount at which the active ingredient, bispecific antibody, can exert pharmaceutically meaningful effects in preventing or treating cancer. The pharmaceutically effective amount of the bispecific antibody, or a suitable dosage of the pharmaceutical composition indicated by an amount of the bispecific antibody, may be prescribed in a variety of ways, depending on various factors, such as age, body weight, gender, pathologic conditions, diets, excretion speed, and/or reaction sensitivity of a patient, formulation types, administration time, administration route, administration manner, and the like. For example, the pharmaceutically effective amount of the bispecific antibody, or a suitable dosage of the pharmaceutical composition, may be in the range from about 0.001 to about 1000 mg (amount of the bispecific antibody)/kg (body weight), about 0.01 to about 100 mg/kg, or 0.1 to 50 mg/kg per day for an adult.

The subject to which the bispecific antibody or the pharmaceutical composition is administered may be one selected from mammals, for example, humans, monkeys, rats, mice, dogs, cats, guinea pigs, rabbits, rats, mice, horses, cattle, cows, and so on, or a cell or tissue obtained therefrom, but are not limited thereto, and it may be one suffering from cancer.

The pharmaceutical composition may be formulated with a pharmaceutically acceptable carrier and/or excipient into a unit or a multiple dosage form by a method easily carried out by a skilled person in the pertinent art. The dosage form may be a solution in oil or an aqueous medium, a suspension, syrup, an emulsifying solution, an extract, powder, granules, a tablet, or a capsule, and may further include a dispersing or a stabilizing agent.

Polynucleotide, Recombinant Vector, and Preparation of Antibody

An embodiment provides a polynucleotide encoding the bispecific antibody. For example, the polypeptide may comprise a first polynucleotide encoding a heavy chain of an anti-EGFR antibody as described herein and a scFv of an anti-4-1BB antibody as described herein, which are linked directly or via a peptide linker; and a second polynucleotide encoding a light chain of the anti-EGFR antibody. Alternatively, the polypeptide may comprise a first polynucleotide encoding a heavy chain of an anti-4-1BB antibody as described herein and a scFv of an anti-EGFR antibody as described herein, which are linked directly or via a peptide linker; and a second polynucleotide encoding a light chain of the anti-4-1BB antibody.

Another embodiment provides a recombinant vector comprising the polynucleotide. For example, the recombinant vector may comprise the first polynucleotide and the second polynucleotide together in one vector or separately in two vectors. Another embodiment provides a recombinant cell comprising the first polynucleotide and the second polynucleotide. For example, the recombinant cell may be a cell transfected with the recombinant vector.

Another embodiment provides a method of preparing the bispecific antibody, comprising expressing the polynucleotide, for example the first polynucleotide and the second polynucleotide, in a cell. The step of expressing the polynucleotide may be conducted by culturing the cell comprising the polynucleotide (for example, in a recombinant vector) under a condition allowing the expression of the polynucleotide. The method may further comprise isolating and/or purifying the anti-4-1BB antibody or an antigen-binding fragment thereof from the cell culture, after the step of expressing or culturing.

The term "vector" refers to a means for expressing a target gene in a host cell, as exemplified by a plasmid vector, a cosmid vector, and a viral vector such as a bacteriophage vector, an adenovirus vector, a retrovirus vector, and an adeno-associated virus vector. The recombinant vector may be constructed from plasmids frequently used in the art (for example, pSC101, pGV1106, pACYC177, ColE1, pKT230, pME290, pBR322, pUC8/9, pUC6, pBD9, pHC79, pIJ61, pLAFR1, pHV14, pGEX series, pET series, and pUC19), phages (for example, λgt4λB, λ-Charon, λΔz1, and M13) or by manipulating viruses (for example, SV40, etc.).

In the recombinant vector, the polynucleotide may be operatively linked to a promoter. The term "operatively linked" is intended to pertain to a functional linkage between a nucleotide sequence of interest and an expression regulatory sequence (for example, a promoter sequence). When being "operatively linked", the regulatory element can control the transcription and/or translation of the nucleotide of interest.

The recombinant vector may be constructed typically as a cloning vector or an expression vector. For recombinant expression vectors, a vector generally available in the relevant art for expressing a foreign protein in plant, animal, or microbial cells may be employed. Various methods well known in the art may be used for the construction of recombinant vectors.

For use in hosts, such as prokaryotic or eukaryotic cells, the recombinant vector may be constructed accordingly. For example, when a vector is constructed as an expression vector for use in a prokaryotic host, the vector typically includes a strong promoter for transcription (e.g., a pLκλ promoter, a CMV promoter, a trp promoter, a lac promoter, a tac promoter, a T7 promoter, etc.), a ribosomal binding site for initiating translation, and transcriptional/translational termination sequences. On the other hand, an expression vector for use in a eukaryotic host includes an origin of replication operable in a eukaryotic cell, such as an f1 origin of replication, an SV40 origin of replication, a pMB1 origin of replication, an adeno origin of replication, an AAV origin of replication, and a BBV origin of replication, but is not limited thereto. In addition, the expression vector typically includes a promoter derived from genomes of mammalian cells (for example, metallothionein promoter) or from mammalian viruses (for example, adenovirus late promoter, vaccinia virus 7.5K promoter, SV40 promoter, cytomegalovirus promoter, and tk promoter of HSV), and a polyadenylation sequence as a transcription termination sequence.

The recombinant cell may be prepared by introducing the recombinant vector into a suitable host cell. As long as it allows the sequential cloning and expression of the recombinant vector in a stable manner, any host cell known in the art may be employed in the present disclosure. Examples of the prokaryotic host cell available for the present disclosure may be selected from *E. coli*, *Bacillus* spp. such as *Bacillus subtilis* and *Bacillus thuringiensis*, and enterobacteriaceae strains such as *Salmonella typhimurium*, *Serratia marcescens* and various *Pseudomonas* species. Eukaryotic host cells that may be used for transformation may selected from, but are not limited to, *Saccharomyces cerevisiae*, insect cells, and animal cells, such as Sp2/0, CHO (Chinese hamster ovary) K1, CHO DG44, PER.C6, W138, BHK, COS-7, 293, HepG2, Huh7, 3T3, RIN, and MDCK.

The polynucleotide or a recombinant vector carrying the same may be introduced (transfected) into a host cell using a method well known in the relevant art. For example, this transfection may be carried out using a CaCl2) or electroporation method when the host cell is prokaryotic. For eukaryotic host cells, the genetic introduction may be achieved using, but not limited to, microinjection, calcium phosphate precipitation, electroporation, liposome-mediated transfection, or particle bombardment.

To select a transformed host cell, advantage may be taken of a phenotype associated with a selection marker according to methods well known in the art. For example, when the selection marker is a gene conferring resistance to a certain antibiotic, the host cells may be grown in the presence of the antibiotic in a medium to select a transformant of interest.

Another embodiment provides a method for production of the bispecific antibody, the method comprising a step of expressing the polynucleotide or the recombinant vector in a host cell. In one embodiment, the production method may comprise culturing a recombinant cell harboring the polynucleotide or the recombinant vector thereat, and optionally isolating and/or purifying the antibody from the culture medium.

EXAMPLES

Hereafter, the present invention will be described in detail by examples.

The following examples are intended merely to illustrate the invention and are not construed to restrict the invention.

Example 1. Anti-4-1BB Antibodies 1.1 Preparation of Full Human Monoclonal Antibodies Against 4-1BB Full human monoclonal anti-4-1BB antibodies in a full-length IgG form were screened by phage library (obtained from KBio Health) immunotube panning against 4-1BB. For panning of the phage library against target molecules, four rounds of panning were carried out in total using 4-1BB (NCBI Accession No. NP_001552.2) coated immunotubes.

Bacterial colonies from the 3 rounds of panning output were grown in SB-Carbenicillin (Biomatik cat #A2311-5g) in 96 deepwell plate until turbid, at which point $10^{11}$ pfu of VCSM13 helper phage (K-Bio Health) was added to each well. After 1 h infection at 37° C. with gentle shaking (80 rpm), 70 µg/mL of kanamycin was added and the cells were cultured overnight at 30° C. with shaking at 200 rpm.

Next day, the plates were centrifuged and the supernatants containing the phages were added to 4-1BB antigen-coated ELISA plates blocked with 3% (v/v) BSA (bovine serum albumin) in PBST (Phosphate Buffered Saline with Tween 20). After 1 h incubation at room temperature, the plates were washed three times with PBST and anti M13 antibody (Sino Biological cat #11973-MM05) was added. The plates were incubated for 1 h, washed three times with PBST, and the binding activity was measured using tetramethylbenzidine (TMB).

The 4-1BB specific binders were amplified for plasmid DNA sequencing. The light chain- and heavy chain-variable region (VL and VH) sequences were analyzed to identify unique sequences and determine sequence diversity, as shown in Tables 6 to 13 (Underline: CDR1, CDR2, and CDR3, in order). The anti-4-1BB antibody indicated as BMUR (BMS's Urelumab, U.S. Pat. No. 7,288,638) is used for comparing agonistic activity in following examples.

TABLE 6

1A10

| | |
|---|---|
| 1A10 | Amino acid sequence (N'→C') |
| Heavy Chain | EVQLLESGGGLVQPGGSLRLSCAASGFTFSSYDMSWVRQAP GKGLEWVSWISYSGGSIYYADSVKGRFTISRDNSKNTLYLQMN SLRAEDTAVYYCARDGQRNSMREFDYWGQGTLVTVSSASTK GPSVFPLAPCSRSTSESTAALGCLVKDYFPEPVTVSWNSGALT SGVHTFPAVLQSSGLYSLSSVVTVPSSSLGTKTYTCNVDHKPS NTKVDKRVESKYGPPCPPCPAPEFLGGPSVFLFPPKPKDTLMI SRTPEVTCVVVDVSQEDPEVQFNWYVDGVEVHNAKTKPREE QFNSTYRVVSVLTVLHQDWLNGKEYKCKVSNKGLPSSIEKTIS KAKGQPREPQVYTLPPSQEEMTKNQVSLTCLVKGFYPSDIAVE WESNGQPENNYKTTPPVLDSDGSFFLYSRLTVDKSRWQEGN VFSCSVMHEALHNHYTQKSLSLSLGK (SEQ ID NO: 56) |
| Heavy Chain Variable Region (VH) | EVQLLESGGGLVQPGGSLRLSCAASGFTFSSYDMSWVRQAP GKGLEWVSWISYSGGSIYYADSVKGRFTISRDNSKNTLYLQMN SLRAEDTAVYYCARDGQRNSMREFDYWGQGTLVTVSS (SEQ ID NO: 18) |
| H-CDR1 | SYDMS (SEQ ID NO: 1) |
| H-CDR2 | WISYSGGSIYYADSVKG (SEQ ID NO: 4) |
| H-CDR3 | DGQRNSMREFDY (SEQ ID NO: 7) |
| Light Chain | QSVLTQPPSASGTPGRRVTISCSGSSSNIGNNYVTWYQQLPG TAPKLLIYADSHRPSGVPDRFSGSKSGTSASLAISGLRSEDEA DYYCATWDYSLSGYVFGGGTKLTVLGQPKAAPSVTLFPPSSEE LQANKATLVCLISDFYPGAVTVAWKADSSPVKAGVETTTPSKQ SNNKYAASSYLSLTPEQWKSHRSYSCQVTHEGSTVEKTVAPAE CS (SEQ ID NO: 62) |
| Light Chain Variable Region (VL) | QSVLTQPPSASGTPGRRVTISCSGSSSNIGNNYVTWYQQLPGT APKLLIYADSHRPSGVPDRFSGSKSGTSASLAISGLRSEDEAD YYCATWDYSLSGYVFGGGTKLTVL (SEQ ID NO: 30) |
| L-CDR1 | SGSSSNIGNNYVT (SEQ ID NO: 12) |
| L-CDR2 | ADSHRPS (SEQ ID NO: 14) |
| L-CDR3 | ATWDYSLSGYV (SEQ ID NO: 16) |

TABLE 7

1A10 M4

| | |
|---|---|
| 1A10 M4 | Amino acid sequence (N'→C') |
| Heavy Chain | EVQLLESGGGLVQPGGSLRLSCAASGFTFSSYDMSWVRQAP GKGLEWVSWISYSGGSIYYADSVKGRFTISRDNSKNTLYLQMN SLRAEDTAVYYCARDAQRNSMREFDYWGQGTLVTVSSASTK GPSVFPLAPCSRSTSESTAALGCLVKDYFPEPVTVSWNSGALT SGVHTFPAVLQSSGLYSLSSVVTVPSSSLGTKTYTCNVDHKPS NTKVDKRVESKYGPPCPPCPAPEFLGGPSVFLFPPKPKDTLMI SRTPEVTCVVVDVSQEDPEVQFNWYVDGVEVHNAKTKPREE QFNSTYRVVSVLTVLHQDWLNGKEYKCKVSNKGLPSSIEKTIS KAKGQPREPQVYTLPPSQEEMTKNQVSLTCLVKGFYPSDIAVE WESNGQPENNYKTTPPVLDSDGSFFLYSRLTVDKSRWQEGN VFSCSVMHEALHNHYTQKSLSLSLGK (SEQ ID NO: 57) |
| Heavy Chain Variable Region (VH) | EVQLLESGGGLVQPGGSLRLSCAASGFTFSSYDMSWVRQAP GKGLEWVSWISYSGGSIYYADSVKGRFTISRDNSKNTLYLQMN SLRAEDTAVYYCARDAQRNSMREFDYWGQGTLVTVSS (SEQ ID NO: 19) |
| H-CDR1 | SYDMS (SEQ ID NO: 1) |
| H-CDR2 | WISYSGGSIYYADSVKG (SEQ ID NO: 4) |
| H-CDR3 | DAQRNSMREFDY (SEQ ID NO: 8) |

TABLE 7-continued

1A10 M4

| | |
|---|---|
| 1A10 M4 | Amino acid sequence (N'→C') |
| Light Chain | QSVLTQPPSASGTPGRRVTISCSGSSSNIGNNYVTWYQQLPGT APKLLIYADSHRPSGVPDRFSGSKSGTSASLAISGLRSEDEAD YYCATWDYSLSGYVFGGGTKLTVLGQPKAAPSVTLFPPSSEEL QANKATLVCLISDFYPGAVTVAWKADSSPVKAGVETTTPSKQS NNKYAASSYLSLTPEQWKSHRSYSCQVTHEGSTVEKTVAPAEC S (SEQ ID NO: 62) |
| Light Chain Variable Region (VL) | QSVLTQPPSASGTPGRRVTISCSGSSSNIGNNYVTWYQQLPGT APKLLIYADSHRPSGVPDRFSGSKSGTSASLAISGLRSEDEAD YYCATWDYSLSGYVFGGGTKLTVL (SEQ ID NO: 30) |
| L-CDR1 | SGSSSNIGNNYVT (SEQ ID NO: 12) |
| L-CDR2 | ADSHRPS (SEQ ID NO: 14) |
| L-CDR3 | ATWDYSLSGYV (SEQ ID NO: 16) |

TABLE 8

1A10 M11

| | |
|---|---|
| 1A10 M11 | Amino acid sequence (N'→C') |
| Heavy Chain | EVQLLESGGGLVQPGGSLRLSCAASGFTFSSYDMSWVRQAP GKGLEWVSWISYSGGSIYYADSVKGRFTISRDNSKNTLYLQMN SLRAEDTAVYYCARDAQRQSMREFDYWGQGTLVTVSSASTK GPSVFPLAPCSRSTSESTAALGCLVKDYFPEPVTVSWNSGALT SGVHTFPAVLQSSGLYSLSSVVTVPSSSLGTKTYTCNVDHKPS NTKVDKRVESKYGPPCPPCPAPEFLGGPSVFLFPPKPKDTLMI SRTPEVTCVVVDVSQEDPEVQFNWYVDGVEVHNAKTKPREE QFNSTYRVVSVLTVLHQDWLNGKEYKCKVSNKGLPSSIEKTIS KAKGQPREPQVYTLPPSQEEMTKNQVSLTCLVKGFYPSDIAVE WESNGQPENNYKTTPPVLDSDGSFFLYSRLTVDKSRWQEGN VFSCSVMHEALHNHYTQKSLSLSLGK (SEQ ID NO: 58) |
| Heavy Chain Variable Region (VH) | EVQLLESGGGLVQPGGSLRLSCAASGFTFSSYDMSWVRQAP GKGLEWVSWISYSGGSIYYADSVKGRFTISRDNSKNTLYLQMN SLRAEDTAVYYCARDAQRQSMREFDYWGQGTLVTVSS (SEQ ID NO: 20) |
| H-CDR1 | SYDMS (SEQ ID NO: 1) |
| H-CDR2 | WISYSGGSIYYADSVKG (SEQ ID NO: 4) |
| H-CDR3 | DAQRQSMREFDY (SEQ ID NO: 9) |
| Light Chain | QSVLTQPPSASGTPGRRVTISCSGSSSNIGNNYVTWYQQLPGT APKLLIYADSHRPSGVPDRFSGSKSGTSASLAISGLRSEDEAD YYCATWDYSLSGYVFGGGTKLTVLGQPKAAPSVTLFPPSSEEL QANKATLVCLISDFYPGAVTVAWKADSSPVKAGVETTTPSKQS NNKYAASSYLSLTPEQWKSHRSYSCQVTHEGSTVEKTVAPAEC S(SEQ ID NO: 62) |
| Light Chain Variable Region (VL) | QSVLTQPPSASGTPGRRVTISCSGSSSNIGNNYVTWYQQLPGT APKLLIYADSHRPSGVPDRFSGSKSGTSASLAISGLRSEDEAD YYCATWDYSLSGYVFGGGTKLTVL (SEQ ID NO: 30) |
| L-CDR1 | SGSSSNIGNNYVT (SEQ ID NO: 12) |
| L-CDR2 | ADSHRPS (SEQ ID NO: 14) |
| L-CDR3 | ATWDYSLSGYV (SEQ ID NO: 16) |

TABLE 9

1A10 M12

| | |
|---|---|
| 1A10 M12 Amino acid sequence (N'→C') | |
| Heavy Chain | EVQLLESGGGLVQPGGSLRLSCAASGFTFSSYDMSWVRQAP GKGLEWVSWISYSGGSIYYADSVKGRFTISRDNSKNTLYLQMN SLRAEDTAVYYCARDAQRNSMREFDYWGQGTLVTVSSASTK GPSVFPLAPCSRSTSESTAALGCLVKDYFPEPVTVSWNSGALT SGVHTFPAVLQSSGLYSLSSVVTVPSSSLGTKTYTCNVDHKPS NTKVDKRVESKYGPPCPPCPAPEFLGGPSVFLFPPKPKDTLMI SRTPEVTCVVVDVSQEDPEVQFNWYVDGVEVHNAKTKPREE QFNSTYRVVSVLTVLHQDWLNGKEYKCKVSNKGLPSSIEKTIS KAKGQPREPQVYTLPPSQEEMTKNQVSLTCLVKGFYPSDIAVE WESNGQPENNYKTTPPVLDSDGSFFLYSRLTVDKSRWQEGN VFSCSVMHEALHNHYTQKSLSLSLGK (SEQ ID NO: 57) |
| Heavy Chain Variable Region (VH) | EVQLLESGGGLVQPGGSLRLSCAASGFTFSSYDMSWVRQAP GKGLEWVSWISYSGGSIYYADSVKGRFTISRDNSKNTLYLQMN SLRAEDTAVYYCARDAQRNSMREFDYWGQGTLVTVSS (SEQ ID NO: 19) |
| H-CDR1 | SYDMS (SEQ ID NO: 1) |
| H-CDR2 | WISYSGGSIYYADSVKG (SEQ ID NO: 4) |
| H-CDR3 | DAQRNSMREFDY (SEQ ID NO: 8) |
| Light Chain | QSVLTQPPSASGTPGQRVTISCSGSSSNIGNNYVTWYQQLPGT APKLLIYADSHRPSGVPDRFSGSKSGTSASLAISGLRSEDEAD YYCATWDYSLSGYVFGGGTKLTVLGQPKAAPSVTLFPPSSEEL QANKATLVCLISDFYPGAVTVAWKADSSPVKAGVETTTPSKQS NNKYAASSYLSLTPEQWKSHRSYSCQVTHEGSTVEKTVAPAEC S (SEQ ID NO: 63) |
| Light Chain Variable Region (VL) | QSVLTQPPSASGTPGQRVTISCSGSSSNIGNNYVTWYQQLPG TAPKLLIYADSHRPSGVPDRFSGSKSGTSASLAISGLRSEDE ADYYCATWDYSLSGYVFGGGTKLTVL (SEQ ID NO: 31) |
| L-CDR1 | SGSSSNIGNNYVT (SEQ ID NO: 12) |
| L-CDR2 | ADSHRPS (SEQ ID NO: 14) |
| L-CDR3 | ATWDYSLSGYV (SEQ ID NO: 16) |

TABLE 10

1A10 M13

| | |
|---|---|
| 1A10 M13 Amino acid sequence (N'→C') | |
| Heavy Chain | EVQLLESGGGLVQPGGSLRLSCAASGFTFSSYDMSWVRQAP GKGLEWVSWISYSGGSIYYADSVKGRFTISRDNSKNTLYLQMN SLRAEDTAVYYCARDAQRQSMREFDYWGQGTLVTVSSASTK GPSVFPLAPCSRSTSESTAALGCLVKDYFPEPVTVSWNSGALT SGVHTFPAVLQSSGLYSLSSVVTVPSSSLGTKTYTCNVDHKPS NTKVDKRVESKYGPPCPPCPAPEFLGGPSVFLFPPKPKDTLMI SRTPEVTCVVVDVSQEDPEVQFNWYVDGVEVHNAKTKPREE QFNSTYRVVSVLTVLHQDWLNGKEYKCKVSNKGLPSSIEKTIS KAKGQPREPQVYTLPPSQEEMTKNQVSLTCLVKGFYPSDIAVE WESNGQPENNYKTTPPVLDSDGSFFLYSRLTVDKSRWQEGN VFSCSVMHEALHNHYTQKSLSLSLGK (SEQ ID NO: 58) |
| Heavy Chain Variable Region (VH) | EVQLLESGGGLVQPGGSLRLSCAASGFTFSSYDMSWVRQAP GKGLEWVSWISYSGGSIYYADSVKGRFTISRDNSKNTLYLQMN SLRAEDTAVYYCARDAQRQSMREFDYWGQGTLVTVSS (SEQ ID NO: 20) |
| H-CDR1 | SYDMS (SEQ ID NO: 1) |
| H-CDR2 | WISYSGGSIYYADSVKG (SEQ ID NO: 4) |
| H-CDR3 | DAQRQSMREFDY (SEQ ID NO: 9) |

TABLE 10-continued

1A10 M13

| | |
|---|---|
| 1A10 M13 Amino acid sequence (N'→C') | |
| Light Chain | QSVLTQPPSASGTPGQRVTISCSGSSSNIGNNYVTWYQQLPGT APKLLIYADSHRPSGVPDRFSGSKSGTSASLAISGLRSEDEAD YYCATWDYSLSGYVFGGGTKLTVLGQPKAAPSVTLFPPSSEEL QANKATLVCLISDFYPGAVTVAWKADSSPVKAGVETTTPSKQS NNKYAASSYLSLTPEQWKSHRSYSCQVTHEGSTVEKTVAPAEC S (SEQ ID NO: 63) |
| Light Chain Variable Region (VL) | QSVLTQPPSASGTPGQRVTISCSGSSSNIGNNYVTWYQQLPG TAPKLLIYADSHRPSGVPDRFSGSKSGTSASLAISGLRSEDE ADYYCATWDYSLSGYVFGGGTKLTVL (SEQ ID NO: 31) |
| L-CDR1 | SGSSSNIGNNYVT (SEQ ID NO: 12) |
| L-CDR2 | ADSHRPS (SEQ ID NO: 14) |
| L-CDR3 | ATWDYSLSGYV (SEQ ID NO: 16) |

TABLE 11

1A12

| | |
|---|---|
| 1A12 Amino acid sequence (N'→C') | |
| Heavy Chain | EVQLLESGGGLVQPGGSLRLSCAASGFTFSGYDMSWVRQAP GKGLEWVSVIYPDDGNTYYADSVKGRFTISRDNSKNTLYLQMN SLRAEDAAVYYCAKHGGQKPTTKSSSAYGMDGWGQGTLVTV SSASTKGPSVFPLAPCSRSTSESTAALGCLVKDYFPEPVTVSW NSGALTSGVHTFPAVLQSSGLYSLSSVVTVPSSSLGTKTYTCN VDHKPSNTKVDKRVESKYGPPCPPCPAPEFLGGPSVFLFPPK PKDTLMISRTPEVTCVVVDVSQEDPEVQFNWYVDGVEVHNAK TKPREEQFNSTYRVVSVLTVLHQDWLNGKEYKCKVSNKGLPS SIEKTISKAKGQPREPQVYTLPPSQEEMTKNQVSLTCLVKGFY PSDIAVEWESNGQPENNYKTTPPVLDSDGSFFLYSRLTVDKSR WQEGNVFSCSVMHEALHNHYTQKSLSLSLGK (SEQ ID NO: 59) |
| Heavy Chain Variable Region (VH) | EVQLLESGGGLVQPGGSLRLSCAASGFTFSGYDMSWVRQAP GKGLEWVSVIYPDDGNTYYADSVKGRFTISRDNSKNTLYLQMN SLRAEDAAVYYCAKHGGQKPTTKSSSAYGMDGWGQGTLVTV SS (SEQ ID NO: 21) |
| H-CDR1 | GYDMS (SEQ ID NO: 2) |
| H-CDR2 | VIYPDDGNTYYADSVKG (SEQ ID NO: 5) |
| H-CDR3 | HGGQKPTTKSSSAYGMDG (SEQ ID NO: 10) |
| Light Chain | QSVLTQPPSASGTPGRRVTISCSGSSSNIGNNYVTWYQQLPGT APKLLIYADSHRPSGVPDRFSGSKSGTSASLAISGLRSEDEAD YYCATWDYSLSGYVFGGGTKLTVLGQPKAAPSVTLFPPSSEEL QANKATLVCLISDFYPGAVTVAWKADSSPVKAGVETTTPSKQS NNKYAASSYLSLTPEQWKSHRSYSCQVTHEGSTVEKTVAPAEC S (SEQ ID NO: 62) |
| Light Chain Variable Region (VL) | QSVLTQPPSASGTPGRRVTISCSGSSSNIGNNYVTWYQQLPGT APKLLIYADSHRPSGVPDRFSGSKSGTSASLAISGLRSEDEAD YYCATWDYSLSGYVFGGGTKLTVL (SEQ ID NO: 30) |
| L-CDR1 | SGSSSNIGNNYVT (SEQ ID NO: 12) |
| L-CDR2 | ADSHRPS (SEQ ID NO: 14) |
| L-CDR3 | ATWDYSLSGYV (SEQ ID NO: 16) |

TABLE 12

1A12 M1

| | 1A12 M1 Amino acid sequence (N'→C') |
|---|---|
| Heavy Chain | EVQLLESGGGLVQPGGSLRLSCAASGFTFSGYDMSWVRQAP GKGLEWVSVIYPDDGNTYYADSVKGRFTISRDNSKNTLYLQMN SLRAEDTAVYYCAKHGGQKPTTKSSSAYGMDGWGQGTLVTV SSASTKGPSVFPLAPCSRSTSESTAALGCLVKDYFPEPVTVSW NSGALTSGVHTFPAVLQSSGLYSLSSVVTVPSSSLGTKTYTCN VDHKPSNTKVDKRVESKYGPPCPPCPAPEFLGGPSVFLFPPK PKDTLMISRTPEVTCVVVDVSQEDPEVQFNWYVDGVEVHNAK TKPREEQFNSTYRVVSVLTVLHQDWLNGKEYKCKVSNKGLPS SIEKTISKAKGQPREPQVYTLPPSQEEMTKNQVSLTCLVKGFY PSDIAVEWESNGQPENNYKTTPPVLDSDGSFFLYSRLTVDKSR WQEGNVFSCSVMHEALHNHYTQKSLSLSLGK (SEQ ID NO: 60) |
| Heavy Chain Variable Region (VH) | EVQLLESGGGLVQPGGSLRLSCAASGFTFSGYDMSWVRQAP GKGLEWVSVIYPDDGNTYYADSVKGRFTISRDNSKNTLYLQMN SLRAEDTAVYYCAKHGGQKPTTKSSSAYGMDGWGQGTLVTV SS (SEQ ID NO: 22) |
| H-CDR1 | GYDMS (SEQ ID NO: 2) |
| H-CDR2 | VIYPDDGNTYYADSVKG (SEQ ID NO: 5) |
| H-CDR3 | HGGQKPTTKSSSAYGMDG (SEQ ID NO: 10) |
| Light Chain | QSVLTQPPSASGTPGQRVTISCSGSSSNIGNNYVTWYQQLPGT APKLLIYADSHRPSGVPDRFSGSKSGTSASLAISGLRSEDEAD YYCATWDYSLSGYVFGGGTKLTVLGQPKAAPSVTLFPPSSEEL QANKATLVCLISDFYPGAVTVAWKADSSPVKAGVETTTPSKQS NNKYAASSYLSLTPEQWKSHRSYSCQVTHEGSTVEKTVAPAEC S (SEQ ID NO: 63) |
| Light Chain Variable Region (VL) | QSVLTQPPSASGTPGQRVTISCSGSSSNIGNNYVTWYQQLPG TAPKLLIYADSHRPSGVPDRFSGSKSGTSASLAISGLRSEDE ADYYCATWDYSLSGYVFGGGTKLTVL (SEQ ID NO: 31) |
| L-CDR1 | SGSSSNIGNNYVT (SEQ ID NO: 12) |
| L-CDR2 | ADSHRPS (SEQ ID NO: 14) |
| L-CDR3 | ATWDYSLSGYV (SEQ ID NO: 16) |

TABLE 13

AB41

| | AB41 Amino acid sequence (N'→C') |
|---|---|
| Heavy Chain | QVQLQQSGAEVIKPGASVKLSCKASGYTFSSYWMHWVRQAP GQGLEWIGEINPGNGHTNYNEKFKSRATLTGDTSTSTVYMELS SLRSEDTAVYYCARSFTTARAFAYWGQGTLVTVSSASTKGPS VFPLAPCSRSTSESTAALGCLVKDYFPEPVTVSWNSGALTSGV HTFPAVLQSSGLYSLSSVVTVPSSSLGTKTYTCNVDHKPSNTK VDKRVESKYGPPCPPCPAPEFLGGPSVFLFPPKPKDTLMISRT PEVTCVVVDVSQEDPEVQFNWYVDGVEVHNAKTKPREEQFN STYRVVSVLTVLHQDWLNGKEYKCKVSNKGLPSSIEKTISKAK GQPREPQVYTLPPSQEEMTKNQVSLTCLVKGFYPSDIAVEWE SNGQPENNYKTTPPVLDSDGSFFLYSRLTVDKSRWQEGNVFS CSVMHEALHNHYTQKSLSLSLGK (SEQ ID NO: 61) |
| Heavy Chain Variable Region (VH) | QVQLQQSGAEVIKPGASVKLSCKASGYTFSSYWMHWVRQAP GQGLEWIGEINPGNGHTNYNEKFKSRATLTGDTSTSTVYMELS SLRSEDTAVYYCARSFTTARAFAYWGQGTLVTVSS (SEQ ID NO: 23) |
| H-CDR1 | SYWMH (SEQ ID NO: 3) |
| H-CDR2 | EINPGNGHTNYNEKFKS (SEQ ID NO: 6) |
| H-CDR3 | SFTTARAFAY (SEQ ID NO: 11) |
| Light Chain | DIVMTQSPAFLSVTPGEKVTITCRASQTISDYLHWYQQKPDQA PKLLIKYASQSISGIPSRFSGSGSGTDFTFTISSLEAEDAATY YCQDGHSFPPTFGQGTKLEIKRTVAAPSVFIFPPSDEQLKSGT ASVVCLLNNFYPREAKVQWKVDNALQSGNSQESVTEQDSKDST YSLSSTLTLSKADYEKHKVYACEVTHQGLSSPVTKSFNRGEC (SEQ ID NO: 64) |
| Light Chain Variable Region (VL) | DIVMTQSPAFLSVTPGEKVTITCRASQTISDYLHWYQQKPDQA PKLLIKYASQSISGIPSRFSGSGSGTDFTFTISSLEAEDAATY YCQDGHSFPPTFGQGTKLEIKR (SEQ ID NO: 32) |
| L-CDR1 | RASQTISDYLH (SEQ ID NO: 13) |
| L-CDR2 | YASQSIS (SEQ ID NO: 15) |
| L-CDR3 | QDGHSFPPT (SEQ ID NO: 17) |

1.2. Preparation of scFv Antibodies Against 4-1BB

Anti-4-1BB scFv antibodies with a structure of (N')-VL-linker-VH-(C') were prepared using the variable regions of the full human monoclonal antibodies against 4-1BB shown in Tables 6 to 13 of Example 1.1, wherein the amino acid residue "G" at the position 44 of a heavy chain variable region was substituted with "C", and the amino acid residue "G" at the position 103 of a light chain variable region was substituted with "C". Such amino acid substitution from "G" to "C" in scFv can contribute to increase in stabilities of bispecific antibodies comprising the scFv as one target-specific moiety. The amino acid sequences of the prepared anti-4-1BB scFvs were illustrated in following Tables 14 to 19, while skilled persons in the art may apply changes or modifications of amino acid sequences in the following embodiments to meet specific purposes, including applying various types of peptide linkers such as (GGGGS)2 (SEQ ID NO: 91), (GGGGS)3 (SEQ ID NO: 85), (GGGGS)4 (SEQ ID NO: 87), or (GS)9 (SEQ ID NO: 86).

TABLE 14

1A10 (scFv)

| | Amino acid sequence (N'→C') |
|---|---|
| Light chain variable region (VL) | QSVLTQPPSASGTPGRRVTISCSGSSSNIGNNYVT WYQQLPGTAPKLLIYADSHRPSGVPDRFSGSKSGT SASLAISGLRSEDEADYYCATWDYSLSGYVFGCGT KLTVL (SEQ ID NO: 33) |
| Linker | GGGGSGGGGSGGGGSGGGGS (SEQ ID NO: 87) |
| Heavy chain variable region (VH) | EVQLLESGGGLVQPGGSLRLSCAASGFTFSSYDMS WVRQAPGKCLEWVSWISYSGGSIYYADSVKGRFTI SRDNSKNTLYLQMNSLRAEDTAVYYCARDGQRNSM REFDYWGQGTLVTVSS (SEQ ID NO: 24) |

TABLE 15

1A10 M4 (scFv)

| | Amino acid sequence (N'→C') |
|---|---|
| Light chain variable region (VL) | QSVLTQPPSASGTPGRRVTISCSGSSSNIGNNYVTWYQQLPGTAPKLLIYADSHRPSGVPDRFSGSKSGTSASLAISGLRSEDEADYYCATWDYSLSGYVFGCGTKLTVL (SEQ ID NO: 33) |
| Linker | GGGGSGGGGSGGGGSGGGGS (SEQ ID NO: 87) |
| Heavy chain variable region (VH) | EVQLLESGGGLVQPGGSLRLSCAASGFTFSSYDMSWVRQAPGKCLEWVSWISYSGGSIYYADSVKGRFTISRDNSKNTLYLQMNSLRAEDTAVYYCARDAQRNSMREFDYWGQGTLVTVSS (SEQ ID NO: 25) |

TABLE 16

1A10 M12 (scFv)

| | Amino acid sequence (N'→C') |
|---|---|
| Light chain variable region (VL) | QSVLTQPPSASGTPGQRVTISCSGSSSNIGNNYVTWYQQLPGTAPKLLIYADSHRPSGVPDRFSGSKSGTSASLAISGLRSEDEADYYCATWDYSLSGYVFGCGTKLTVL (SEQ ID NO: 34) |
| Linker | GGGGSGGGGSGGGGSGGGGS (SEQ ID NO: 87) |
| Heavy chain variable region (VH) | EVQLLESGGGLVQPGGSLRLSCAASGFTFSSYDMSWVRQAPGKCLEWVSWISYSGGSIYYADSVKGRFTISRDNSKNTLYLQMNSLRAEDTAVYYCARDAQRNSMREFDYWGQGTLVTVSS (SEQ ID NO: 25) |

TABLE 17

1A12 (scFv)

| | Amino acid sequence (N'→C') |
|---|---|
| Light chain variable region (VL) | QSVLTQPPSASGTPGRRVTISCSGSSSNIGNNYVTWYQQLPGTAPKLLIYADSHRPSGVPDRFSGSKSGTSASLAISGLRSEDEADYYCATWDYSLSGYVFGCGTKLTVL (SEQ ID NO: 33) |
| Linker | GGGGSGGGGSGGGGSGGGGS (SEQ ID NO: 87) |
| Heavy chain variable region (VH) | EVQLLESGGGLVQPGGSLRLSCAASGFTFSSYDMSWVRQAPGKCLEWVSVIYPDDGNTYYADSVKGRFTISRDNSKNTLYLQMNSLRAEDAAVYYCAKHGGQKPTTKSSSAYGMDGWGQGTLVTVSS (SEQ ID NO: 27) |

TABLE 18

1A12 M1 (scFv)

| | Amino acid sequence (N'→C') |
|---|---|
| Light chain variable region (VL) | QSVLTQPPSASGTPGQRVTISCSGSSSNIGNNYVTWYQQLPGTAPKLLIYADSHRPSGVPDRFSGSKSGTSASLAISGLRSEDEADYYCATWDYSLSGYVFGCGTKLTVL (SEQ ID NO: 34) |
| Linker | GGGGSGGGGSGGGGSGGGGS (SEQ ID NO: 67) |
| Heavy chain variable region (VH) | EVQLLESGGGLVQPGGSLRLSCAASGFTFSSYDMSWVRQAPGKCLEWVSVIYPDDGNTYYADSVKGRFTISRDNSKNTLYLQMNSLRAEDTAVYYCAKHGGQKPTTKSSSAYGMDGWGQGTLVTVSS (SEQ ID NO: 28) |

TABLE 19

AB41 (scFv)

| | Amino acid sequence (N'→C') |
|---|---|
| Light chain variable region (VL) | DIVMTQSPAFLSVTPGEKVTITCRASQTISDYLHWYQQKPDQAPKLLIKYASQSISGIPSRFSGSGSGTDFTFTISSLEAEDAATYYCQDGHSFPPTFGCGTKLEIKR (SEQ ID NO: 88) |
| Linker | GGGGSGGGGSGGGGSGGGGS (SEQ ID NO: 67) |
| Heavy chain variable region (VH) | QVQLQQSGAEVIKPGASVKLSCKASGYTFSSYWMHWVRQAPGQCLEWIGEINPGNGHTNYNEKFKSRATLTGDTSTSTVYMELSSLRSEDTAVYYCARSFTTARAFAYWGQGTLVTVSS (SEQ ID NO: 29) |

1.3. Antigen Binding Abilities of Anti-4-1BB Antibodies (Full-Length IgG Form) to Human 4-1BB (1) Antigen Binding Activity Measured by ELISA To evaluate the antigen binding activity, the antibody candidates prepared in Example 1.1 were subjected to ELISA test. Briefly, microtiter plates were coated with human 4-1BB-Fc protein (Sino Biological) at 0.1 µg/ml in PBS, 100 µl/well at 4° C. overnight, and then blocked with 100 µl/well of 5% (v/v) BSA. Five-fold dilutions of humanized antibodies (1A10, 1A12, and AB41) starting from 10 µg/ml were added to each well and incubated for 1-2 hours at room temperature (RT). The plates were washed with PBS/Tween and then incubated with goat-anti-human IgG antibody conjugated with Horse Radish Peroxidase (HRP) (Thermo) for 1 hour at RT. After washing, the plates were developed with TMB substrate and analyzed by spectrophotometer at OD 450-630 nm.

The obtained results are shown in FIG. 1a. As shown in FIG. 1a, all the anti-4-1BB antibodies tested show 4-1BB binding abilities.

(2) Cell Binding Activity Measured by FACS

To evaluate the cell binding activity, the antibody candidates were analyzed for its binding to mammalian expressed 4-1BB by fluorescence-activated cell sorting (FACS). Briefly, GloResponse™ NFκB-luc2/4-1BB Jurkat cell line (Promega; 3×10⁵ of cells), which are Jurkat cells expressing 4-1BB on their surface, were incubated with antibodies (1A10 and 1A12; each 10 ug/mL). After wash by FACS buffer (1% (v/v) BSA in PBS), the FITC-anti-human IgG antibody (Sigma, F9512, concentration: 2.0 mg/ml) was added to each well and incubated at 4° C. for 1 hour. The mean fluorescence intensity (MFI) of FITC was evaluated by FACSCalibur (BD Biosciences).

The obtained results are shown in FIG. 1b. As shown in FIG. 1b, all the anti-4-1BB antibodies tested show binding abilities to 4-1BB which expressed on cell surface and can efficiently bind to 4-1BB expressed on mammalian cells.

Example 2. Preparation of Anti-EGFR Antibodies

As an EGFR targeting moiety for anti-EGFR/Anti-4-1BB bispecific antibodies, Cetuximab (ERBITUX®: BMS", DrugBank Accession No. DB00002; human IgG1 Kappa monoclonal antibody), or its antigen-binding fragment, such as scFv, was employed.

The sequences of Cetuximab are summarized as follows:

Heavy Chain:

(SEQ ID NO: 90)
QVQLKQSGPGLVQPSQSLSITCTVSGFSLTNYGVHWVRQSPGKGLEWLGV

IWSGGNITDYNTPFTSRLSINKDNSKSQVFFKMNSLOSNDTANYCARALT

YYDYEFAYWGQGTLVTVSAASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLFPPKPK

DTLMISRTPEVICVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSRDELTKNQVSLICLVKGFYPSDIAVEWESNGQPENNYKTTPPVL

DSOGSFFLYSKLTVDKSRWQQGNVFSCSVMHEALHNHYTQKSLSLSPGK

Light Chain:

(SEQ ID NO: 75)
DILLTQSPVILSVSPGERVSFSCRASQSIGTNIHWYQQRTNGSPRLLIKY

ASESISGIPSRFSGSGSGTDFTLSINSVESEDIADYYCQQNNNWPTTFGA

GTKLELKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

The constant region of the anti-EGFR antibody contained in the bispecific antibody can be modified by introducing more than one mutation or change into human IgG1, one exemplary embodiment (hereinafter, indicated as "ET(WT)") being illustrated in Table 20:

TABLE 20

| ET(WT) | Sequence |
|---|---|
| Heavy Chain | QVQLKQSGPGLVQPSQSLSITCTVSGFSLTNYGVHWVRQS PGKGLEWLGVIWSGGNTDYNTPFTSRLSINKDNSKSQVFFK MNSLQSNDTAIYYCARALTYYDYEFAYWGQGTLVTVSSAST KGPSVFPLAPSSKSTSGGTAALGCLVKDYFPEPVTVSWNSG ALTSGVHTFPAVLQSSGLYSLSSVVTVPSSSLGTQTYICNVN HKPSNTKVDKKVEPKSCDKTHTCPPCPAPELLGGPSVFLFP PKPKDTLMISRTPEVTCVVVDVSHEDPEVKFNWYVDGVEVH NAKTKPREEQYNSTYRVVSVLTVLHQDWLNGKEYKCKVSN KALPAPIEKTISKAKGQPREPQVYTLPPSREEMTKNQVSLTC LVKGFYPSDIAVEWESNGQPENNYKTTPPVLDSDGSFFLYS KLTVDKSRWQQGNVFSCSVMHEALHNHYTQKSLSLSPGK (SEQ ID NO: 73) |
| Light Chain | DILLTQSPVILSVSPGERVSFSCRASQSIGTNIHWYQQRTNG SPRLLIKYASESISGIPSRFSGSGSGTDFTLSINSVESEDIA DYYCQQNNNWPTTFGAGTKLELKRTVAAPSVFIFPPSDEQLK SGTASVVCLLNNFYPREAKVQWKVDNALQSGNSQESVTEQD SKDSTYSLSSTLTLSKADYEKHKVYACEVTHQGLSSPVTKSF NRGEC (SEQ ID NO: 75) |

The constant region of the anti-EGFR antibody contained in the bispecific antibody can be modified by introducing more than one mutation or change into human IgG1, one exemplary embodiment, EGFR(NA or N297A) being presented in Table 21 below:

TABLE 21

| ET(NA) (N297A) | Sequence |
|---|---|
| Heavy Chain | QVQLKQSGPGLVQPSQSLSITCTVSGFSLTNYGVHWVRQS PGKGLEWLGVIWSGGNTDYNTPFTSRLSINKDNSKSQVFFK MNSLQSNDTAIYYCARALTYYDYEFAYWGQGTLVTVSSAST KGPSVFPLAPSSKSTSGGTAALGCLVKDYFPEPVTVSWNSG ALTSGVHTFPAVLQSSGLYSLSSVVTVPSSSLGTQTYICNV NHKPSNTKVDKKVEPKSCDKTHTCPPCPAPELLGGPSVFLF PPKPKDTLMISRTPEVTCVVVDVSHEDPEVKFNWYVDGVEV HNAKTKPREEQYASTYRVVSVLTVLHQDWLNGKEYKCKVSN KALPAPIEKTISKAKGQPREPQVYTLPPSREEMTKNQVSLT CLVKGFYPSDIAVEWESNGQPENNYKTTPPVLDSDGSFFLY SKLTVDKSRWQQGNVFSCSVMHEALHNHYTQKSLSLSPGK (SEQ ID NO: 74) |
| Light Chain | DILLTQSPVILSVSPGERVSFSCRASQSIGTNIHWYQQRTN GSPRLLIKYASESISGIPSRFSGSGSGTDFTLSINSVESED IADYYCQQNNNWPTTFGAGTKLELKRTVAAPSVFIFPPSDE QLKSGTASVVCLLNNFYPREAKVQWKVDNALQSGNSQESVT EQDSKDSTYSLSSTLTLSKADYEKHKVYACEVTHQGLSSPV TKSFNRGEC (SEQ ID NO: 75) |

Example 3. Preparation of Anti-EGFR/Anti-4-1BB Bispecific Antibodies

Various anti-EGFR/Anti-4-1BB bispecific antibody candidates were prepared in full-length IgG (anti-EGFR antibody)-scFv (anti-4-1BB antibody) format or in full-length IgG (anti-4-1BB antibody)-scFv (anti-EGFR antibody) format: In this example, the anti-EGFR IgG and 4-1BB scFv clones prepared in Example 2 and Example 1.2, respectively, were exemplarily selected, to prepare anti-EGFR/anti-4-1BB bispecific antibodies in a IgG-scFv fusion form (an scFv antibody fragment of one antigen is fused to c-terminal of IgG of another antigen). When EGFR is placed in full IgG part, IgG1 with ADCC reduced mutant backbone (N297A mutation; Cancer Cell, vol. 19, issue 1, pp. 101-113, etc.) was used, and when 4-1BB is placed in full IgG part, IgG4 was used.

A DNA segment 1 having a nucleotide sequence encoding a heavy chain of an IgG antibody of the anti-EGFR/anti-4-1BB bispecific antibody was inserted into pcDNA 3.4 (Invitrogen, A14697; plasmid 1), and a DNA segment 2 having a nucleotide sequence encoding a light chain of an IgG antibody of the anti-EGFR/anti-4-1BB bispecific antibody was inserted into pcDNA 3.4 (Invitrogen, A14697; plasmid 2). Thereafter, a DNA segment 3 encoding a scFv was fused at a part of the DNA segment 1 corresponding to the c-terminus of the Fc region of the IgG antibody inserted into the plasmid 1, using a DNA segment 4 encoding a linker peptide having 15 amino acid lengths consisting of (GGGGS)3 or using a DNA segment 5 encoding a linker peptide having 18 amino acid lengths consisting of (GS)9, to construct vectors for the expression of bispecific antibodies. Furthermore, in order to stabilize scFv, as described in Example 1.2, additional modification was applied to generate disulfide bridge fusing VL103-VH44 (VL103: VL having G→C mutation at the position 103; VH 44: VH having G→C mutation at the position 44) to C-terminus of light chain and C-terminus of heavy chain, respectively.

Among the prepared bispecific antibodies, sequences of the heavy chains, light chains, scFvs and DNA segments used in preparing some several exemplary bispecific antibodies are illustrated in Tables 22 to 30. One or more than one point mutations in amino acid sequences can be applied in the antibodies presented below, for the purpose of improved stability and potency, decreased immunogenicity, and etc.

TABLE 22

EGFR(NA)x1A10 bispecific antibody-1

Amino acid sequence (N'→C')

| Heavy component | ① Heavy chain of anti-EGFR antibody | QVQLKQSGPGLVQPSQSLSITCTVSGFSLTNYGV HWVRQSPGKGLEWLGVIWSGGNTDYNTPFTSRL SINKDNSKSQVFFKMNSLQSNDTAIYYCARALTYY DYEFAYWGQGTLVTVSSASTKGPSVFPLAPSSKS TSGGTAALGCLVKDYFPEPVTVSWNSGALTSGVH TFPAVLQSSGLYSLSSVVTVPSSSLGTQTYICNVN HKPSNTKVDKKVEPKSCDKTHTCPPCPAPELLGG PSVFLFPPKPKDTLMISRTPEVTCVVVDVSHEDPE VKFNWYVDGVEVHNAKTKPREEQYASTYRVVSV LTVLHQDWLNGKEYKCKVSNKALPAPIEKTISKAK GQPREPQVYTLPPSREEMTKNQVSLTCLVKGFYP SDIAVEWESNGQPENNYKTTPPVLDSDGSFFLYS KLTVDKSRWQQGNVFSCSVMHEALHNHYTQKSL SLSPGK (SEQ ID NO: 74) |
|---|---|---|
| | ② Linker | GGGGSGGGGSGGGGS (SEQ ID NO: 85) |
| | ③ scFv VL of anti-4-1BB antibody | QSVLTQPPSASGTPGRRVTISCSGSSSNIGNNYVT WYQQLPGTAPKLLIYADSHRPSGVPDRFSGSKSG TSASLAISGLRSEDEADYYCATWDYSLSGYVFGC GTKLTVL (SEQ ID NO: 33) |
| | Linker | GGGGSGGGGSGGGGSGGGGS (SEQ ID NO: 87) |
| | VH | EVQLLESGGGLVQPGGSLRLSCAASGFTFSSYDM SWVRQAPGKCLEWVSWISYSGGSIYYADSVKGR FTISRDNSKNTLYLQMNSLRAEDTAVYYCARDGQ RNSMREFDYWGQGTLVTVSS (SEQ ID NO: 24) |
| | Heavy component (① + ② + ③) | QVQLKQSGPGLVQPSQSLSITCTVSGFSLTNYGV HWVRQSPGKGLEWLGVIWSGGNTDYNTPFTSRL SINKDNSKSQVFFKMNSLQSNDTAIYYCARALTYY DYEFAYWGQGTLVTVSSASTKGPSVFPLAPSSKS TSGGTAALGCLVKDYFPEPVTVSWNSGALTSGVH TFPAVLQSSGLYSLSSVVTVPSSSLGTQTYICNVN HKPSNTKVDKKVEPKSCDKTHTCPPCPAPELLGG PSVFLFPPKPKDTLMISRTPEVTCVVVDVSHEDPE VKFNWYVDGVEVHNAKTKPREEQYASTYRVVSV LTVLHQDWLNGKEYKCKVSNKALPAPIEKTISKAK GQPREPQVYTLPPSREEMTKNQVSLTCLVKGFYP SDIAVEWESNGQPENNYKTTPPVLDSDGSFFLYS KLTVDKSRWQQGNVFSCSVMHEALHNHYTQKSL SLSPGKGGGGSGGGGSGGGGSQSVLTQPPSAS GTPGRRVTISCSGSSSNIGNNYVTWYQQLPGTAP KLLIYADSHRPSGVPDRFSGSKSGTSASLAISGLR SEDEADYYCATWDYSLSGYVFGCGTKLTVLGGG GSGGGGSGGGGSGGGGSEVQLLESGGGLVQPG GSLRLSCAASGFTFSSYDMSWVRQAPGKCLEWV SWISYSGGSIYYADSVKGRFTISRDNSKNTLYLQM NSLRAEDTAVYYCARDGQRNSMREFDYWGQGTL VTVSS (SEQ ID NO: 76) |
| Light component | Light chain of anti-EGFR antibody | DILLTQSPVILSVSPGERVSFSCRASQSIGTNIHW YQQRTNGSPRLLIKYASESISGIPSRFSGSGSGTD FTLSINSVESEDIADYYCQQNNNWPTTFGAGTKLE LKRTVAAPSVFIFPPSDEQLKSGTASVVCLLNNFY PREAKVQWKVDNALQSGNSQESVTEQDSKDSTYS LSSTLTLSKADYEKHKVYACEVTHQGLSSPVTKSF NRGEC (SEQ ID NO: 75) |

TABLE 23

EGFR(NA)x1A10 bispecific antibody-2

Amino acid sequence (N'→C')

| Heavy component | ① Heavy chain of anti-EGFR antibody | QVQLKQSGPGLVQPSQSLSITCTVSGFSLTNYG VHWVRQSPGKGLEWLGVIWSGGNTDYNTPFTS RLSINKDNSKSQVFFKMNSLQSNDTAIYYCARAL TYYDYEFAYWGQGTLVTVSSASTKGPSVFPLAP SSKSTSGGTAALGCLVKDYFPEPVTVSWNSGAL TSGVHTFPAVLQSSGLYSLSSVVTVPSSSLGTQT YICNVNHKPSNTKVDKKVEPKSCDKTHTCPPCP APELLGGPSVFLFPPKPKDTLMISRTPEVTCVVV DVSHEDPEVKFNWYVDGVEVHNAKTKPREEQY ASTYRVVSVLTVLHQDWLNGKEYKCKVSNKALP APIEKTISKAKGQPREPQVYTLPPSREEMTKNQV SLTCLVKGFYPSDIAVEWESNGQPENNYKTTPP |

TABLE 23-continued

EGFR(NA)x1A10 bispecific antibody-2

Amino acid sequence (N'→C')

| | | |
|---|---|---|
| | ② Linker | VLDSDGSFFLYSKLTVDKSRWQQGNVFSCSVM<br>HEALHNHYTQKSLSLSPGK (SEQ ID NO: 74)<br>GSGSGSGSGSGSGSGS (SEQ ID NO: 86) |
| | ③ scFv VL<br>of anti-<br>4-1BB<br>antibody | QSVLTQPPSASGTPGRRVTISCSGSSSNIGNNYV<br>TWYQQLPGTAPKLLIYADSHRPSGVPDRFSGSK<br>SGTSASLAISGLRSEDEADYYCATWDYSLSGYVF<br>GCGTKLTVL (SEQ ID NO: 33) |
| | Linker | GGGGSGGGGSGGGGSGGGGS (SEQ ID NO: 87) |
| | VH | EVQLLESGGGLVQPGGSLRLSCAASGFTFSSYD<br>MSWVRQAPGKCLEWVSWISYSGGSIYYADSVK<br>GRFTISRDNSKNTLYLQMNSLRAEDTAVYYCAR<br>DGQRNSMREFDYWGQGTLVTVSS (SEQ ID<br>NO: 24) |
| | Heavy component<br>(① + ② + ③) | QVQLKQSGPGLVQPSQSLSITCTVSGFSLTNYG<br>VHWVRQSPGKGLEWLGVIWSGGNTDYNTPFTS<br>RLSINKDNSKSQVFFKMNSLQSNDTAIYYCARAL<br>TYYDYEFAYWGQGTLVTVSSASTKGPSVFPLAP<br>SSKSTSGGTAALGCLVKDYFPEPVTVSWNSGAL<br>TSGVHTFPAVLQSSGLYSLSSVVTVPSSSLGTQT<br>YICNVNHKPSNTKVDKKVEPKSCDKTHTCPPCP<br>APELLGGPSVFLFPPKPKDTLMISRTPEVTCVVV<br>DVSHEDPEVKFNWYVDGVEVHNAKTKPREEQY<br>ASTYRVVSVLTVLHQDWLNGKEYKCKVSNKALP<br>APIEKTISKAKGQPREPQVYTLPPSREEMTKNQV<br>SLTCLVKGFYPSDIAVEWESNGQPENNYKTTPP<br>VLDSDGSFFLYSKLTVDKSRWQQGNVFSCSVM<br>HEALHNHYTQKSLSLSPGKGSGSGSGSGSGSG<br>SGSGSGQSVLTQPPSASGTPGRRVTISCSGSSSNI<br>GNNYVTWYQQLPGTAPKLLIYADSHRPSGVPDR<br>FSGSKSGTSASLAISGLRSEDEADYYCATWDYSL<br>SGYVFGCGTKLTVLGGGGSGGGGSGGGGSGG<br>GGSEVQLLESGGGLVQPGGSLRLSCAASGFTFS<br>SYDMSWVRQAPGKCLEWVSWISYSGGSIYYAD<br>SVKGRFTISRDNSKNTLYLQMNSLRAEDTAVYY<br>CARDGQRNSMREFDYWGQGTLVTVSS (SEQ ID<br>NO: 77) |
| Light<br>component | Light chain of<br>anti-EGFR<br>antibody | DILLTQSPVILSVSPGERVSFSCRASQSIGTNIHW<br>YQQRTNGSPRLLIKYASESISGIPSRFSGSGSGT<br>DFTLSINSVESEDIADYYCQQNNNWPTTFGAGT<br>KLELKRTVAAPSVFIFPPSDEQLKSGTASVVCLL<br>NNFYPREAKVQWKVDNALQSGNSQESVTEQDS<br>KDSTYSLSSTLTLSKADYEKHKVYACEVTHQGLS<br>SPVTKSFNRGEC (SEQ ID NO: 75) |

TABLE 24

EGFR(NA)x1A10 M4 bispecific antibody

Amino acid sequence (N'→C')

| | | |
|---|---|---|
| Heavy<br>component | ① Heavy chain of<br>anti-EGFR<br>antibody | QVQLKQSGPGLVQPSQSLSITCTVSGFSLTNYG<br>VHWVRQSPGKGLEWLGVIWSGGNTDYNTPFTS<br>RLSINKDNSKSQVFFKMNSLQSNDTAIYYCARAL<br>TYYDYEFAYWGQGTLVTVSSASTKGPSVFPLAP<br>SSKSTSGGTAALGCLVKDYFPEPVTVSWNSGAL<br>TSGVHTFPAVLQSSGLYSLSSVVTVPSSSLGTQT<br>YICNVNHKPSNTKVDKKVEPKSCDKTHTCPPCP<br>APELLGGPSVFLFPPKPKDTLMISRTPEVTCVVV<br>DVSHEDPEVKFNWYVDGVEVHNAKTKPREEQY<br>ASTYRVVSVLTVLHQDWLNGKEYKCKVSNKALP<br>APIEKTISKAKGQPREPQVYTLPPSREEMTKNQV<br>SLTCLVKGFYPSDIAVEWESNGQPENNYKTTPP<br>VLDSDGSFFLYSKLTVDKSRWQQGNVFSCSVM<br>HEALHNHYTQKSLSLSPGK (SEQ ID NO: 74) |
| | ② Linker | GSGSGSGSGSGSGSGS (SEQ ID NO: 86) |
| | ③ scFv VL<br>of anti-<br>4-1BB<br>antibody | QSVLTQPPSASGTPGRRVTISCSGSSSNIGNNYV<br>TWYQQLPGTAPKLLIYADSHRPSGVPDRFSGSK<br>SGTSASLAISGLRSEDEADYYCATWDYSLSGYVF<br>GCGTKLTVL (SEQ ID NO: 33) |
| | Linker | GGGGSGGGGSGGGGSGGGGS (SEQ ID NO: 87) |
| | VH | EVQLLESGGGLVQPGGSLRLSCAASGFTFSSYD<br>MSWVRQAPGKCLEWVSWISYSGGSIYYADSVK |

TABLE 24-continued

EGFR(NA)x1A10 M4 bispecific antibody

Amino acid sequence (N'→C')

|  |  |  |
|---|---|---|
|  |  | GRFTISRDNSKNTLYLQMNSLRAEDTAVYYCAR DAQRNSMREFDYWGQTLVTVSS (SEQ ID NO: 25) |
|  | Heavy component (① + ② + ③) | QVQLKQSGPGLVQPSQSLSITCTVSGFSLTNYG VHWVRQSPGKGLEWLGVIWSGGNTDYNTPFTS RLSINKDNSKSQVFFKMNSLQSNDTAIYYCARAL TYYDYEFAYWGQGTLVTVSSASTKGPSVFPLAP SSKSTSGGTAALGCLVKDYFPEPVTVSWNSGAL TSGVHTFPAVLQSSGLYSLSSVVTVPSSSLGTQT YICNVNHKPSNTKVDKKVEPKSCDKTHTCPPCP APELLGGPSVFLFPPKPKDTLMISRTPEVTCVVV DVSHEDPEVKFNWYVDGVEVHNAKTKPREEQY ASTYRVVSVLTVLHQDWLNGKEYKCKVSNKALP APIEKTISKAKGQPREPQVYTLPPSREEMTKNQV SLTCLVKGFYPSDIAVEWESNGQPENNYKTTPP VLDSDGSFFLYSKLTVDKSRWQQGNVFSCSVM HEALHNHYTQKSLSLSPGKGSGSGSGSGSGSG SGSGSQSVLTQPPSASGTPGRRVTISCSGSSSNI GNNYVTWYQQLPGTAPKLLIYADSHRPSGVPDR FSGSKSGTSASLAISGLRSEDEADYYCATWDYSL SGYVFGCGTKLTVLGGGGSGGGGSGGGGSGG GGSEVQLLESGGGLVQPGGSLRLSCAASGFTFS SYDMSWVRQAPGKCLEWVSWISYSGGSIYYAD SVKGRFTISRDNSKNTLYLQMNSLRAEDTAVYY CARDAQRNSMREFDYWGQGTLVTVSS (SEQ ID NO: 78) |
| Light component | Light chain of anti-EGFR antibody | DILLTQSPVILSVSPGERVSFSCRASQSIGTNIHW YQQRTNGSPRLLIKYASESISGIPSRFSGSGSGT DFTLSINSVESEDIADYYCQQNNNWPTTFGAGT KLELKRTVAAPSVFIFPPSDEQLKSGTASVVCLL NNFYPREAKVQWKVDNALQSGNSQESVTEQDS KDSTYSLSSTLTLSKADYEKHKVYACEVTHQGLS SPVTKSFNRGEC (SEQ ID NO: 75) |

TABLE 25

EGFR(NA)x1A10 M12 bispecific antibody

Amino acid sequence (N'→C')

|  |  |  |  |
|---|---|---|---|
| Heavy component | ① | Heavy chain of anti-EGFR antibody | QVQLKQSGPGLVQPSQSLSITCTVSGFSLTNYG VHWVRQSPGKGLEWLGVIWSGGNTDYNTPFTS RLSINKDNSKSQVFFKMNSLQSNDTAIYYCARAL TYYDYEFAYWGQGTLVTVSSASTKGPSVFPLAP SSKSTSGGTAALGCLVKDYFPEPVTVSWNSGAL TSGVHTFPAVLQSSGLYSLSSVVTVPSSSLGTQT YICNVNHKPSNTKVDKKVEPKSCDKTHTCPPCP APELLGGPSVFLFPPKPKDTLMISRTPEVTCVVV DVSHEDPEVKFNWYVDGVEVHNAKTKPREEQY ASTYRVVSVLTVLHQDWLNGKEYKCKVSNKALP APIEKTISKAKGQPREPQVYTLPPSREEMTKNQV SLTCLVKGFYPSDIAVEWESNGQPENNYKTTPP VLDSDGSFFLYSKLTVDKSRWQQGNVFSCSVM HEALHNHYTQKSLSLSPGK (SEQ ID NO: 74) |
|  | ② ③ | Linker scFv VL of anti-4-1BB antibody | GSGSGSGSGSGSGSGS (SEQ ID NO: 86) QSVLTQPPSASGTPGQRVTISCSGSSSNIGNNY VTWYQQLPGTAPKLLIYADSHRPSGVPDRFSGS KSGTSASLAISGLRSEDEADYYCATWDYSLSGY VFGCGTKLTVL (SEQ ID NO: 34) |
|  |  | Linker VH | GGGGSGGGGSGGGGSGGGGS (SEQ ID NO: 87) EVQLLESGGGLVQPGGSLRLSCAASGFTFSSYD MSWVRQAPGKCLEWVSWISYSGGSIYYADSVK GRFTISRDNSKNTLYLQMNSLRAEDTAVYYCAR DAQRNSMREFDYWGQGTLVTVSS (SEQ ID NO: 25) |
|  | Heavy component (① + ② + ③) |  | QVQLKQSGPGLVQPSQSLSITCTVSGFSLTNYG VHWVRQSPGKGLEWLGVIWSGGNTDYNTPFTS RLSINKDNSKSQVFFKMNSLQSNDTAIYYCARAL TYYDYEFAYWGQGTLVTVSSASTKGPSVFPLAP SSKSTSGGTAALGCLVKDYFPEPVTVSWNSGAL TSGVHTFPAVLQSSGLYSLSSVVTVPSSSLGTQT YICNVNHKPSNTKVDKKVEPKSCDKTHTCPPCP |

TABLE 25-continued

EGFR(NA)x1A10 M12 bispecific antibody

Amino acid sequence (N'→C')

|   |   |   |
|---|---|---|
| | | APELLGGPSVFLFPPKPKDTLMISRTPEVTCVVV<br>DVSHEDPEVKFNWYVDGVEVHNAKTKPREEQY<br>ASTYRVVSVLTVLHQDWLNGKEYKCKVSNKALP<br>APIEKTISKAKGQPREPQVYTLPPSREEMTKNQV<br>SLTCLVKGFYPSDIAVEWESNGQPENNYKTTPP<br>VLDSDGSFFLYSKLTVDKSRWQQGNVFSCSVM<br>HEALHNHYTQKSLSLSPGKGSGSGSGSGSGSG<br>SGSGSQSVLTQPPSASGTPGQRVTISCSGSSSN<br>IGNNYVTWYQQLPGTAPKLLIYADSHRPSGVPD<br>RFSGSKSGTSASLAISGLRSEDEADYYCATWDY<br>SLSGYVFGCGTKLTVLGGGGSGGGGSGGGGS<br>GGGGSEVQLLESGGGLVQPGGSLRLSCAASGF<br>TFSSYDMSWVRQAPGKCLEWVSWISYSGGSIY<br>YADSVKGRFTISRDNSKNTLYLQMNSLRAEDTA<br>VYYCARDAQRNSMREFDYWGQGTLVTVSS<br>(SEQ ID NO: 79) |
| Light<br>component | Light chain of<br>anti-EGFR<br>antibody | DILLTQSPVILSVSPGERVSFSCRASQSIGTNIHW<br>YQQRTNGSPRLLIKYASESISGIPSRFSGSGSGT<br>DFTLSINSVESEDIADYYCQQNNNWPTTFGAGT<br>KLELKRTVAAPSVFIFPPSDEQLKSGTASVVCLL<br>NNFYPREAKVQWKVDNALQSGNSQESVTEQDS<br>KDSTYSLSSTLTLSKADYEKHKVYACEVTHQGLS<br>SPVTKSFNRGEC (SEQ ID NO: 75) |

TABLE 26

EGFR(NA)x1A12 bispecific antibody-1

Amino acid sequence (N'→C')

| | | |
|---|---|---|
| Heavy<br>component | ① Heavy chain of<br>anti-EGFR<br>antibody | QVQLKQSGPGLVQPSQSLSITCTVSGFSLTNYG<br>VHWVRQSPGKGLEWLGVIWSGGNTDYNTPFTS<br>RLSINKDNSKSQVFFKMNSLQSNDTAIYYCARAL<br>TYYDYEFAYWGQGTLVTVSSASTKGPSVFPLAP<br>SSKSTSGGTAALGCLVKDYFPEPVTVSWNSGAL<br>TSGVHTFPAVLQSSGLYSLSSVVTVPSSSLGTQT<br>YICNVNHKPSNTKVDKKVEPKSCDKTHTCPPCP<br>APELLGGPSVFLFPPKPKDTLMISRTPEVTCVVV<br>DVSHEDPEVKFNWYVDGVEVHNAKTKPREEQY<br>ASTYRVVSVLTVLHQDWLNGKEYKCKVSNKALP<br>APIEKTISKAKGQPREPQVYTLPPSREEMTKNQV<br>SLTCLVKGFYPSDIAVEWESNGQPENNYKTTPP<br>VLDSDGSFFLYSKLTVDKSRWQQGNVFSCSVM<br>HEALHNHYTQKSLSLSPGK (SEQ ID NO: 74) |
| | ② Linker | GGGGSGGGGSGGGGS (SEQ ID NO: 85) |
| | ③ scFv VL<br>of anti-<br>4-1BB<br>antibody | QSVLTQPPSASGTPGRRVTISCSGSSSNIGNNYV<br>TWYQQLPGTAPKLLIYADSHRPSGVPDRFSGSK<br>SGTSASLAISGLRSEDEADYYCATWDYSLSGYVF<br>GCGTKLTVL (SEQ ID NO: 33) |
| | Linker | GGGGSGGGGSGGGGSGGGGS (SEQ ID NO: 87) |
| | VH | EVQLLESGGGLVQPGGSLRLSCAASGFTFSGYD<br>MSWVRQAPGKCLEWVSVIYPDDGNTYYADSVK<br>GRFTISRDNSKNTLYLQMNSLRAEDAAVYYCAK<br>HGGQKPTTKSSSAYGMDGWGQGTLVTVSS<br>(SEQ ID NO: 27) |
| | Heavy component<br>(① + ② + ③) | QVQLKQSGPGLVQPSQSLSITCTVSGFSLTNYG<br>VHWVRQSPGKGLEWLGVIWSGGNTDYNTPFTS<br>RLSINKDNSKSQVFFKMNSLQSNDTAIYYCARAL<br>TYYDYEFAYWGQGTLVTVSSASTKGPSVFPLAP<br>SSKSTSGGTAALGCLVKDYFPEPVTVSWNSGAL<br>TSGVHTFPAVLQSSGLYSLSSVVTVPSSSLGTQT<br>YICNVNHKPSNTKVDKKVEPKSCDKTHTCPPCP<br>APELLGGPSVFLFPPKPKDTLMISRTPEVTCVVV<br>DVSHEDPEVKFNWYVDGVEVHNAKTKPREEQY<br>ASTYRVVSVLTVLHQDWLNGKEYKCKVSNKALP<br>APIEKTISKAKGQPREPQVYTLPPSREEMTKNQV<br>SLTCLVKGFYPSDIAVEWESNGQPENNYKTTPP<br>VLDSDGSFFLYSKLTVDKSRWQQGNVFSCSVM<br>HEALHNHYTQKSLSLSPGKGGGGSGGGGSGG<br>GGSQSVLTQPPSASGTPGRRVTISCSGSSSNIG<br>NNYVTWYQQLPGTAPKLLIYADSHRPSGVPDRF<br>SGSKSGTSASLAISGLRSEDEADYYCATWDYSL |

TABLE 26-continued

EGFR(NA)x1A12 bispecific antibody-1

Amino acid sequence (N'→C')

| | | |
|---|---|---|
| | | SGYVFGCGTKLTVLGGGGSGGGGSGGGGSGG<br>GGSEVQLLESGGGLVQPGGSLRLSCAASGFTFS<br>GYDMSWVRQAPGKCLEWVSVIYPDDGNTYYAD<br>SVKGRFTISRDNSKNTLYLQMNSLRAEDAAVYY<br>CAKHGGQKPTTKSSSAYGMDWGQGTLVTVSS<br>(SEQ ID NO: 80) |
| Light<br>component | Light chain of<br>anti-EGFR<br>antibody | DILLTQSPVILSVSPGERVSFSCRASQSIGTNIHW<br>YQQRTNGSPRLLIKYASESISGIPSRFSGSGSGT<br>DFTLSINSVESEDIADYYCQQNNNWPTTFGAGT<br>KLELKRTVAAPSVFIFPPSDEQLKSGTASVVCLL<br>NNFYPREAKVQWKVDNALQSGNSQESVTEQDS<br>KDSTYSLSSTLTLSKADYEKHKVYACEVTHQGLS<br>SPVTKSFNRGEC (SEQ ID NO: 75) |

TABLE 27

EGFR(NA)x1A12 bispecific antibody-2

Amino acid sequence (N'→C')

| | | |
|---|---|---|
| Heavy<br>component | ① Heavy chain of<br>anti-EGFR<br>antibody | QVQLKQSGPGLVQPSQSLSITCTVSGFSLTNYG<br>VHWVRQSPGKGLEWLGVIWSGGNTDYNTPFTS<br>RLSINKDNSKSQVFFKMNSLQSNDTAIYYCARAL<br>TYYDYEFAYWGQGTLVTVSSASTKGPSVFPLAP<br>SSKSTSGGTAALGCLVKDYFPEPVTVSWNSGAL<br>TSGVHTFPAVLQSSGLYSLSSVVTVPSSSLGTQT<br>YICNVNHKPSNTKVDKKVEPKSCDKTHTCPPCP<br>APELLGGPSVFLFPPKPKDTLMISRTPEVTCVVV<br>DVSHEDPEVKFNWYVDGVEVHNAKTKPREEQY<br>ASTYRVVSVLTVLHQDWLNGKEYKCKVSNKALP<br>APIEKTISKAKGQPREPQVYTLPPSREEMTKNQV<br>SLTCLVKGFYPSDIAVEWESNGQPENNYKTTPP<br>VLDSDGSFFLYSKLTVDKSRWQQGNVFSCSVM<br>HEALHNHYTQKSLSLSPGK (SEQ ID NO: 74) |
| | ② Linker | GSGSGSGSGSGSGSGSGS (SEQ ID NO: 86) |
| | ③ scFv VL<br>of anti-<br>4-1BB<br>antibody | QSVLTQPPSASGTPGRRVTISCSGSSSNIGNNYV<br>TWYQQLPGTAPKLLIYADSHRPSGVPDRFSGSK<br>SGTSASLAISGLRSEDEADYYCATWDYSLSGYVF<br>GCGTKLTVL (SEQ ID NO: 33) |
| | Linker | GGGGSGGGGSGGGGSGGGGS (SEQ ID NO: 87) |
| | VH | EVQLLESGGGLVQPGGSLRLSCAASGFTFSGYD<br>MSWVRQAPGKCLEWVSVIYPDDGNTYYADSVK<br>GRFTISRDNSKNTLYLQMNSLRAEDAAVYYCAK<br>HGGQKPTTKSSSAYGMDWGQGTLVTVSS<br>(SEQ ID NO: 27) |
| | Heavy component<br>(① + ② + ③) | QVQLKQSGPGLVQPSQSLSITCTVSGFSLTNYG<br>VHWVRQSPGKGLEWLGVIWSGGNTDYNTPFTS<br>RLSINKDNSKSQVFFKMNSLQSNDTAIYYCARAL<br>TYYDYEFAYWGQGTLVTVSSASTKGPSVFPLAP<br>SSKSTSGGTAALGCLVKDYFPEPVTVSWNSGAL<br>TSGVHTFPAVLQSSGLYSLSSVVTVPSSSLGTQT<br>YICNVNHKPSNTKVDKKVEPKSCDKTHTCPPCP<br>APELLGGPSVFLFPPKPKDTLMISRTPEVTCVVV<br>DVSHEDPEVKFNWYVDGVEVHNAKTKPREEQY<br>ASTYRVVSVLTVLHQDWLNGKEYKCKVSNKALP<br>APIEKTISKAKGQPREPQVYTLPPSREEMTKNQV<br>SLTCLVKGFYPSDIAVEWESNGQPENNYKTTPP<br>VLDSDGSFFLYSKLTVDKSRWQQGNVFSCSVM<br>HEALHNHYTQKSLSLSPGKGSGSGSGSGSGSG<br>SGSGSQSVLTQPPSASGTPGRRVTISCSGSSSNI<br>GNNYVTWYQQLPGTAPKLLIYADSHRPSGVPDR<br>FSGSKSGTSASLAISGLRSEDEADYYCATWDYSL<br>SGYVFGCGTKLTVLGGGGSGGGGSGGGGSGG<br>GGSEVQLLESGGGLVQPGGSLRLSCAASGFTFS<br>GYDMSWVRQAPGKCLEWVSVIYPDDGNTYYAD<br>SVKGRFTISRDNSKNTLYLQMNSLRAEDAAVYY<br>CAKHGGQKPTTKSSSAYGMDWGQGTLVTVSS<br>(SEQ ID NO: 81) |

TABLE 27-continued

EGFR(NA)x1A12 bispecific antibody-2

Amino acid sequence (N'→C')

| | | |
|---|---|---|
| Light component | Light chain of anti-EGFR antibody | DILLTQSPVILSVSPGERVSFSCRASQSIGTNIHW YQQRTNGSPRLLIKYASESISGIPSRFSGSGSGT DFTLSINSVESEDIADYYCQQNNNWPTTFGAGT KLELKRTVAAPSVFIFPPSDEQLKSGTASVVCLL NNFYPREAKVQWKVDNALQSGNSQESVTEQDS KDSTYSLSSTLTLSKADYEKHKVYACEVTHQGLS SPVTKSFNRGEC (SEQ ID NO: 75) |

TABLE 28

EGFR(NA)x1A12M1 bispecific antibody

Amino acid sequence (N'→C')

| | | |
|---|---|---|
| Heavy component | ① Heavy chain of anti-EGFR antibody | QVQLKQSGPGLVQPSQSLSITCTVSGFSLTNYG VHWVRQSPGKGLEWLGVIWSGGNTDYNTPFTS RLSINKDNSKSQVFFKMNSLQSNDTAIYYCARAL TYYDYEFAYWGQGTLVTVSSASTKGPSVFPLAP SSKSTSGGTAALGCLVKDYFPEPVTVSWNSGAL TSGVHTFPAVLQSSGLYSLSSVVTVPSSSLGTQT YICNVNHKPSNTKVDKKVEPKSCDKTHTCPPCP APELLGGPSVFLFPPKPKDTLMISRTPEVTCVVV DVSHEDPEVKFNWYVDGVEVHNAKTKPREEQY ASTYRVVSVLTVLHQDWLNGKEYKCKVSNKALP APIEKTISKAKGQPREPQVYTLPPSREEMTKNQV SLTCLVKGFYPSDIAVEWESNGQPENNYKTTPP VLDSDGSFFLYSKLTVDKSRWQQGNVFSCSVM HEALHNHYTQKSLSLSPGK (SEQ ID NO: 74) |
| | ② Linker | GSGSGSGSGSGSGSGS (SEQ ID NO: 86) |
| | ③ scFv VL of anti-4-1BB antibody | QSVLTQPPSASGTPGQRVTISCSGSSSNIGNNY VTWYQQLPGTAPKLLIYADSHRPSGVPDRFSGS KSGTSASLAISGLRSEDEADYYCATWDYSLSGY VFGCGTKLTVL (SEQ ID NO: 34) |
| | Linker VH | GGGGSGGGGSGGGGSGGGGS (SEQ ID NO: 87) EVQLLESGGGLVQPGGSLRLSCAASGFTFSGYD MSWVRQAPGKCLEWVSVIYPDDGNTYYADSVK GRFTISRDNSKNTLYLQMNSLRAEDTAVYYCAK HGGQKPTTKSSSAYGMDGWGQGTLVTVSS (SEQ ID NO: 28) |
| | Heavy component (① + ② + ③) | QVQLKQSGPGLVQPSQSLSITCTVSGFSLTNYG VHWVRQSPGKGLEWLGVIWSGGNTDYNTPFTS RLSINKDNSKSQVFFKMNSLQSNDTAIYYCARAL TYYDYEFAYWGQGTLVTVSSASTKGPSVFPLAP SSKSTSGGTAALGCLVKDYFPEPVTVSWNSGAL TSGVHTFPAVLQSSGLYSLSSVVTVPSSSLGTQT YICNVNHKPSNTKVDKKVEPKSCDKTHTCPPCP APELLGGPSVFLFPPKPKDTLMISRTPEVTCVVV DVSHEDPEVKFNWYVDGVEVHNAKTKPREEQY ASTYRVVSVLTVLHQDWLNGKEYKCKVSNKALP APIEKTISKAKGQPREPQVYTLPPSREEMTKNQV SLTCLVKGFYPSDIAVEWESNGQPENNYKTTPP VLDSDGSFFLYSKLTVDKSRWQQGNVFSCSVM HEALHNHYTQKSLSLSPGKGSGSGSGSGSGSG SGSGSQSVLTQPPSASGTPGQRVTISCSGSSSN IGNNYVTWYQQLPGTAPKLLIYADSHRPSGVPD RFSGSKSGTSASLAISGLRSEDEADYYCATWDY SLSGYVFGCGTKLTVLGGGGSGGGGSGGGGS GGGGSEVQLLESGGGLVQPGGSLRLSCAASGF TFSGYDMSWVRQAPGKCLEWVSVIYPDDGNTY YADSVKGRFTISRDNSKNTLYLQMNSLRAEDTA VYYCAKHGGQKPTTKSSSAYGMDGWGQGTLVT VSS (SEQ ID NO: 82) |
| Light component | Light chain of anti-EGFR antibody | DILLTQSPVILSVSPGERVSFSCRASQSIGTNIHW YQQRTNGSPRLLIKYASESISGIPSRFSGSGSGT DFTLSINSVESEDIADYYCQQNNNWPTTFGAGT KLELKRTVAAPSVFIFPPSDEQLKSGTASVVCLL NNFYPREAKVQWKVDNALQSGNSQESVTEQDS KDSTYSLSSTLTLSKADYEKHKVYACEVTHQGLS SPVTKSFNRGEC (SEQ ID NO: 75) |

TABLE 29

EGFR(WT)x1A10 M12 bispecific antibody

Amino acid sequence (N'→C')

| Heavy component | ① Heavy chain of anti-EGFR antibody | QVQLKQSGPGLVQPSQSLSITCTVSGFSLTNYG VHWVRQSPGKGLEWLGVIWSGGNTDYNTPFTS RLSINKDNSKSQVFFKMNSLQSNDTAIYYCARAL TYYDYEFAYWGQGTLVTVSSASTKGPSVFPLAP SSKSTSGGTAALGCLVKDYFPEPVTVSWNSGAL TSGVHTFPAVLQSSGLYSLSSVVTVPSSSLGTQT YICNVNHKPSNTKVDKKVEPKSCDKTHTCPPCP APELLGGPSVFLFPPKPKDTLMISRTPEVTCVVV DVSHEDPEVKFNWYVDGVEVHNAKTKPREEQY NSTYRVVSVLTVLHQDWLNGKEYKCKVSNKALP APIEKTISKAKGQPREPQVYTLPPSREEMTKNQV SLTCLVKGFYPSDIAVEWESNGQPENNYKTTPP VLDSDGSFFLYSKLTVDKSRWQQGNVFSCSVM HEALHNHYTQKSLSLSPGK (SEQ ID NO: 73) |
| --- | --- | --- |
| | ② Linker | GSGSGSGSGSGSGSGS (SEQ ID NO: 86) |
| | ③ scFv VL of anti-4-1BB antibody | QSVLTQPPSASGTPGQRVTISCSGSSSNIGNNY VTWYQQLPGTAPKLLIYADSHRPSGVPDRFSGS KSGTSASLAISGLRSEDEADYYCATWDYSLSGY VFGCGTKLTVL (SEQ ID NO: 34) |
| | Linker | GGGGSGGGGSGGGGSGGGGS (SEQ ID NO: 87) |
| | VH | EVQLLESGGGLVQPGGSLRLSCAASGFTFSSYD MSWVRQAPGKCLEWVSWISYSGGSIYYADSVK GRFTISRDNSKNTLYLQMNSLRAEDTAVYYCAR DAQRNSMREFDYWGQGTLVTVSS (SEQ ID NO: 25) |
| | Heavy component (① + ② + ③) | QVQLKQSGPGLVQPSQSLSITCTVSGFSLTNYG VHWVRQSPGKGLEWLGVIWSGGNTDYNTPFTS RLSINKDNSKSQVFFKMNSLQSNDTAIYYCARAL TYYDYEFAYWGQGTLVTVSSASTKGPSVFPLAP SSKSTSGGTAALGCLVKDYFPEPVTVSWNSGAL TSGVHTFPAVLQSSGLYSLSSVVTVPSSSLGTQT YICNVNHKPSNTKVDKKVEPKSCDKTHTCPPCP APELLGGPSVFLFPPKPKDTLMISRTPEVTCVVV DVSHEDPEVKFNWYVDGVEVHNAKTKPREEQY NSTYRVVSVLTVLHQDWLNGKEYKCKVSNKALP APIEKTISKAKGQPREPQVYTLPPSREEMTKNQV SLTCLVKGFYPSDIAVEWESNGQPENNYKTTPP VLDSDGSFFLYSKLTVDKSRWQQGNVFSCSVM HEALHNHYTQKSLSLSPGKGSGSGSGSGSGSG SGSGSGQSVLTQPPSASGTPGQRVTISCSGSSSN IGNNYVTWYQQLPGTAPKLLIYADSHRPSGVPD RFSGSKSGTSASLAISGLRSEDEADYYCATWDY SLSGYVFGCGTKLTVLGGGGSGGGGSGGGGS GGGGSEVQLLESGGGLVQPGGSLRLSCAASGF TFSSYDMSWVRQAPGKCLEWVSWISYSGGSIY YADSVKGRFTISRDNSKNTLYLQMNSLRAEDTA VYYCARDAQRNSMREFDYWGQGTLVTVSS (SEQ ID NO: 83) |
| Light component | Light chain of anti-EGFR antibody | DILLTQSPVILSVSPGERVSFSCRASQSIGTNIHW YQQRTNGSPRLLIKYASESISGIPSRFSGSGSGT DFTLSINSVESEDIADYYCQQNNNWPTTFGAGT KLELKRTVAAPSVFIFPPSDEQLKSGTASVVCLL NNFYPREAKVQWKVDNALQSGNSQESVTEQDS KDSTYSLSSTLTLSKADYEKHKVYACEVTHQGLS SPVTKSFNRGEC (SEQ ID NO: 75) |

TABLE 30

EGFR(WT)x1A12 M1 bispecific antibody

Amino acid sequence (N'→C')

| Heavy component | ① Heavy chain of anti-EGFR antibody | QVQLKQSGPGLVQPSQSLSITCTVSGFSLTNYG VHWVRQSPGKGLEWLGVIWSGGNTDYNTPFTS RLSINKDNSKSQVFFKMNSLQSNDTAIYYCARAL TYYDYEFAYWGQGTLVTVSSASTKGPSVFPLAP SSKSTSGGTAALGCLVKDYFPEPVTVSWNSGAL TSGVHTFPAVLQSSGLYSLSSVVTVPSSSLGTQT YICNVNHKPSNTKVDKKVEPKSCDKTHTCPPCP APELLGGPSVFLFPPKPKDTLMISRTPEVTCVVV DVSHEDPEVKFNWYVDGVEVHNAKTKPREEQY NSTYRVVSVLTVLHQDWLNGKEYKCKVSNKALP |
| --- | --- | --- |

TABLE 30-continued

EGFR(WT)x1A12 M1 bispecific antibody

Amino acid sequence (N'→C')

| | | |
|---|---|---|
| | ② Linker | APIEKTISKAKGQPREPQVYTLPPSREEMTKNQV SLTCLVKGFYPSDIAVEWESNGQPENNYKTTPP VLDSDGSFFLYSKLTVDKSRWQQGNVFSCSVM HEALHNHYTQKSLSLSPGK (SEQ ID NO: 73) GSGSGSGSGSGSGSGSGS (SEQ ID NO: 86) |
| | ③ scFv VL of anti-4-1BB antibody | QSVLTQPPSASGTPGQRVTISCSGSSSNIGNNY VTWYQQLPGTAPKLLIYADSHRPSGVPDRFSGS KSGTSASLAISGLRSEDEADYYCATWDYSLSGY VFGCGTKLTVL (SEQ ID NO: 34) |
| | Linker VH | GGGGSGGGGSGGGGSGGGGS (SEQ ID NO: 67) EVQLLESGGGLVQPGGSLRLSCAASGFTFSGYD MSWVRQAPGKCLEWVSVIYPDDGNTYYADSVK GRFTISRDNSKNTLYLQMNSLRAEDTAVYYCAK HGGQKPTTKSSSAYGMDGWGQGTLVTVSS (SEQ ID NO: 28) |
| | Heavy component (① + ② + ③) | QVQLKQSGPGLVQPSQSLSITCTVSGFSLTNYG VHWVRQSPGKGLEWLGVIWSGGNTDYNTPFTS RLSINKDNSKSQVFFKMNSLQSNDTAIYYCARAL TYYDYEFAYWGQGTLVTVSSASTKGPSVFPLAP SSKSTSGGTAALGCLVKDYFPEPVTVSWNSGAL TSGVHTFPAVLQSSGLYSLSSVVTVPSSSLGTQT YICNVNHKPSNTKVDKKVEPKSCDKTHTCPPCP APELLGGPSVFLFPPKPKDTLMISRTPEVTCVVV DVSHEDPEVKFNWYVDGVEVHNAKTKPREEQY NSTYRVVSVLTVLHQDWLNGKEYKCKVSNKALP APIEKTISKAKGQPREPQVYTLPPSREEMTKNQV SLTCLVKGFYPSDIAVEWESNGQPENNYKTTPP VLDSDGSFFLYSKLTVDKSRWQQGNVFSCSVM HEALHNHYTQKSLSLSPGKGSGSGSGSGSGSG SGSGSQSVLTQPPSASGTPGQRVTISCSGSSSN IGNNYVTWYQQLPGTAPKLLIYADSHRPSGVPD RFSGSKSGTSASLAISGLRSEDEADYYCATWDY SLSGYVFGCGTKLTVLGGGGSGGGGSGGGGS GGGGSEVQLLESGGGLVQPGGSLRLSCAASGF TFSGYDMSWVRQAPGKCLEWVSVIYPDDGNTY YADSVKGRFTISRDNSKNTLYLQMNSLRAEDTA VYYCAKHGGQKPTTKSSSAYGMDGWGQGTLVT VSS (SEQ ID NO: 84) |
| Light component | Light chain of anti-EGFR antibody | DILLTQSPVILSVSPGERVSFSCRASQSIGTNIHW YQQRTNGSPRLLIKYASESISGIPSRFSGSGSGT DFTLSINSVESEDIADYYCQQNNNWPTTFGAGT KLELKRTVAAPSVFIFPPSDEQLKSGTASVVCLL NNFYPREAKVQWKVDNALQSGNSQESVTEQDS KDSTYSLSSTLTLSKADYEKHKVYACEVTHQGLS SPVTKSFNRGEC (SEQ ID NO: 75) |

Example 4. Test of Binding Affinity of Bispecific Antibodies (BsAbs)

4.1. Binding to Human EGFR

The EGFR binding affinity of the bispecific antibodies were conducted by ELISA referring to Example 1.3(1).

In brief, 96-well microtiter plates (Nunc-Immuno Plates, NUNC) were coated with human EGFR-His protein (Sino Biological, 10001-H08B) at 1 μg/ml in PBS, 100 μl/well at 4° C. overnight, and then blocked with blocking buffer (200 μl/well of 1% BSA (bovine serum albumin (Gibco, 30063572)) in PBS) for 2 hours at 37° C. Six-fold dilutions of anti-EGFR/anti-4-1BB bispecific antibodies prepared in Example 3 starting from 0.1 μM were added to each well and incubated for 1 hour at 37° C. The plates were washed with PBS/0.05% Tween20 and then incubate with HRP-conjugated Fab multiclonal antibody reagent (Pierce, 31414) for 1 hour at 37° C. After washing, the plates were developed with TMB (Tetramethylbenzidine, Sigma, T0440) substrate and analyzed by spectrophotometer at OD 450-650 nm.

The obtained results are shown in FIGS. 2a and 2b. As shown in FIGS. 2a and 2b, all the anti-EGFR/anti-4-1BB bispecific antibodies tested can bind to human EGFR proteins with high affinity, which is similar to that of the control anti-EGFR antibody.

4.2. Binding to Human 4-1BB

The 4-1BB binding affinity of the bispecific antibodies were conducted by ELISA referring to Example 1.3(1).

Briefly, 96-well microtiter plates (Nunc-Immuno Plates, NUNC) were coated with human 4-1BB-His protein (Sino Biological, 10041-H08H) at 1 μg/ml in PBS, 100 μl/well at 4° C. overnight, then blocked with 100 μl/well of 1% BSA (bovine serum albumin (Gibco, 30063572)) in PBS for 2 hours at 37° C. Six-fold dilutions of anti-EGFR/anti-4-1BB bispecific antibodies prepared in Example 3 starting from 0.1 μM were added to each well and incubated for 1 hours at 37° C. The plates were washed with PBS/0.05% Tween20 and then incubate with HRP-conjugated Fab multiclonal antibody reagent (Pierce, 31414) for 1 hour at 37° C. After washing, the plates were developed with TMB (Tetramethylbenzidine, Sigma, T0440) substrate and analyzed by spectrophotometer at OD 450-650 nm.

The obtained results are shown in FIGS. 3a and 3b. As shown in FIGS. 3a and 3b, all the anti-EGFR/anti-4-1BB bispecific antibodies tested can bind to human 4-1BB protein with high affinity, whereas the anti-EGFR antibody does not bind to human 4-1BB protein.

The results of FIGS. 2a, 2b, 3a, and 3b are quantified and summarized in following Table 31:

TABLE 31

| EC50 (nM) | EGFR | 4-1BB |
|---|---|---|
| Anti-EGFR | 0.054 | NA |
| EGFR(WT)x1A10 M12 | 0.063 | 0.033 |
| EGFR(NA)x1A10 | 0.067 | 0.042 |
| EGFR(NA)x1A10 M4 | 0.063 | 0.033 |
| EGFR(NA)x1A10 M12 | 0.060 | 0.037 |
| EGFR(WT)x1A12 M1 | 0.068 | 0.058 |
| EGFR(NA)x1A12 | 0.065 | 0.050 |
| EGFR(NA)x1A12 M1 | 0.055 | 0.060 |

As shown in Table 31, all the anti-EGFR/anti-4-1BB bispecific antibodies tested can bind to both human EGFR and human 4-1BB proteins with high affinities.

4.3. Binding to Various Cell Surface Expressed Human EGFR

The binding affinities of the bispecific antibodies to various cells expressing EGFR on their surface were conducted by FACS analysis referring to Example 1.3(2).

EGFR is expressed in various cancer cells, and it has been reported that it is overexpressed in various solid cancers such as skin cancer, breast cancer, cervix cancer, colon cancer, gastric cancer, pancreatic cancer, Head & neck cancer, etc.

For this experiment, various kinds of cancer cell lines were used as follows: A431 (ATCC® CRL-1555™, epidermoid carcinoma), BT474 (ATCC® HTB-20™, ductal carcinoma), HCC1954 (ATCC® CRL-2338™, TNM stage IIA, grade 3, ductal carcinoma), Jimt-1 (DSMZ ACC 589, Breast carcinoma), Hela (ATCC® CCL-2™, cervix adenocarcinoma), DLD-1 (ATCC® CCL-221™, Dukes' type C, colorectal adenocarcinoma), Kato III (ATCC® HTB-103™, Gastric carcinoma), NCI-N87 (ATCC® CRL-5822™, human gastric carcinoma), MDA-MB-231 (ATCC® HTB-26™, human breast cancer), CFPAC-1 (ATCC® CRL-1918™, Pancreas ductal adenocarcinoma), Panc-1 (ATCC® CRL-1469™, Pancreas epithelioid carcinoma), A253 (ATCC® HTB-41™, submaxillary salivary gland epidermoid carcinoma), Detroit562 (ATCC® CCL-138™, Pharyngeal carcinoma), FaDu (ATCC® HTB-43™, Pharynx squamous cell carcinoma), SCC9 (ATCC® CRL-1629™, Tongue squamous cell carcinoma), SCC15 (ATCC® CRL-1623™, Tongue squamous cell carcinoma), SCC25 (ATCC® CRL-1628™, Tongue squamous cell carcinoma). For the cell lines, the binding to EGFR was analyzed with FACS (FACSCalibur, BD Biosciences) by using the antibodies of the present invention.

Specifically, after disassociating each cell line and washing in PBS, the number of cells was counted and set as $2 \times 10^5$ cells/200 μl FACS buffer, and then anti-EGFRx4-1BB antibodies were treated in 10 μg/mL, and it were reacted at 4° C. for 1 hour. After reaction, cells were washed in FACS buffer, and then the FITC labeled constant region (Fc)-specific antibody (Goat anti-human IgG FITC conjugate, Fc specific, Sigma, F9512, concentration: 2.0 mg/ml) was suspended in 2 μl/$1 \times 10^5$ cells/200 μl FACS buffer, and it was reacted at 4° C. for 1 hour. After reaction, cells were washed in FACS buffer, it was analyzed using a FACSCalibur device. The negative control group was treated only with the FITC-labeled constant region (Fc)-specific antibody. To compare the expression degrees of EGFR among the cancer cell lines, the value of the result for the peak shift in the experimental group was divided by the result for the peak shift in the negative control group (Mean Fluorescence intensity Ratio MFI Ratio: MFI of test antibody/MFI of 2nd Ab).

The obtained results are shown in following Table 32:

TABLE 32

| | | MFI Ratio | | |
|---|---|---|---|---|
| Cancer cell lines | | Anti-EGFR | EGFR × 1A10 | EGFR × 1A12 |
| Skin cancer | A431 | 153 | 148 | 148 |
| Breast Cancer | BT474 | 4 | 4 | 4 |
| | HCC1954 | 11 | 11 | 11 |
| | Jimt-1 | 14 | 14 | 14 |
| | MDA-MB-231 | 24 | 24 | 24 |
| Cervix cancer | Hela | 10 | 10 | 10 |
| Colon cancer | DLD-1 | 8 | 8 | 8 |
| Gastric cancer | Kato III | 7 | 7 | 7 |
| | NCI-N87 | 7 | 7 | 7 |
| Pancreatic cancer | CFPAC-1 | 13 | 12 | 12 |
| | Panc-1 | 22 | 21 | 21 |
| H&N cancer | A253 | 40 | 41 | 40 |
| | Detroit562 | 14 | 14 | 13 |
| | FaDu | ND | 32 | 34 |
| | SCC9 | 17 | 19 | 18 |
| | SCC15 | 49 | 51 | 50 |
| | SCC25 | 25 | 25 | 24 |

(MFI Ratio: MFI of $1^{st}$ Ab/MFI of $2^{nd}$ Ab)
(ND: not determined)

As shown in Table 32, all the anti-EGFR/anti-4-1BB bispecific antibodies tested can bind to cell surface expressed human EGFR proteins.

Example 5. Binding Affinity of BsAbs to 4-1BB (SPR)

In the SPR experiment, the anti-EGFR/anti-4-1BB bispecific antibodies were individually captured on flow-cells 2, 3 and 4, keeping the flow-cell 1 as reference, on a Biocore® Series S Sensor Chip CM5 (GE Healthcare, BR100530) on which an anti-human Fab antibody (GE Healthcare, 28958325) had been immobilized by amine coupling. Recombinant Human 4-1BB protein (ACROBiosystems, 41B-H5227) was flowed across the chip at concentration of 400, 200, 100, 50, 25, 12.5, 6.25, 3.13, 1.56 and 0.78 nM at 30 μl/min for 300 seconds, followed by a dissociation phase of 400 seconds. Regeneration was performed with 10 mM Glycine-HCl (pH 2.0) (GE Healthcare, BR100355).

The obtained results are shown in following Table 33:

TABLE 33

| Antibody | KD (M) | kon(1/Ms) | kdis(1/s) |
|---|---|---|---|
| EGFR(WT)x1A10 M12 | 2.43E−09 | 2.89E+05 | 7.03E−04 |
| EGFR(NA)x1A10 M12 | 2.85E−09 | 2.87E+05 | 8.15E−04 |
| EGFR(WT)x1A12 M1 | 1.34E−08 | 5.15E+04 | 6.89E−04 |
| EGFR(NA)x1A12 M1 | 1.97E−08 | 3.35E+04 | 6.58E−04 |

As shown in Table 33, the anti-EGFR/anti-4-1BB bispecific antibodies tested show high 4-1BB binding affinities.

Example 6. 4-1BB Signal Activation 6.1. BsAbs Vs. Monospecific Antibodies

In this example, for measuring 4-1BB signal activation, GloResponse™ NFκB-luc2/4-1BB Jurkat cell line (Promega), genetically modified to stably express human 4-1BB and luciferase downstream of a response element, was used as effector cell and cancer cells expressing or not expressing EGFR were used as target cells. In brief, as target cells, MDA-MB-231 (expressing EGFR; 2.5×10⁴ cells) or BT-474 (not expressing EGFR; 2.5×10⁴ cells) were plated in a 96-well assay plate and cultured overnight. On the day of assay, the anti-EGFR/anti-4-1BB bispecific antibodies (Example 3; 100 nM or 4 nM, 5-fold-dilution) to be tested and effector Jurkat cells (2.5×10⁴ cells) were added to the plate. After 6 hrs incubation, Bio-Glo™ Reagent (Promega) was added and luminescence was measured using a microplate reader.

The obtained results are shown in following FIGS. 4a (MDA-MB-231 cell line) and 4b (BT-474 cell line). In FIGS. 4a and 4b, BMUR (BMS's Urelumab, U.S. Pat. No. 7,288,638) indicates an anti-4-1BB antibody used for comparing agonistic activity. As shown in FIGS. 4a and 4b, anti-EGFR/anti-4-1BB bispecific antibodies lead to strong activation of 4-1BB signal only when co-cultured with EGFR high expressing cell. Fc crosslinked anti-4-1BB monoclonal antibodies showed minimal activity.

6.2. 4-1BB Activation in Various EGFR-Expressing Cells

In this example, for measuring 4-1BB signal activation, GloResponse™ NFκB-luc2/4-1BB Jurkat cell line (Promega), genetically modified to stably express human 4-1BB and luciferase downstream of a response element, was used as effector cell, and cancer cells expressing or not expressing EGFR were used as target cells. In brief, EGFR-expressing (A-431, HCC1954, Calu-3, DLD-1, SK-BR-3, NCI-N87, MDA-MB-231, Panc-1) or EGFR-non-expressing (CHO-k1, SW620, MC38, Jurkat)) cancer cells (each 2.5×10⁴ cells/well) were plated in a 96-well assay plate and cultured overnight. On the day of assay, the anti-EGFR/anti-4-1BB bispecific antibodies (Example 3; 100 nM or 2 nM, 5-fold-dilution) to be tested and effector Jurkat cells were added to the plate. After 6 hours of incubation, Bio-Glo™ Reagent was added and luminescence was measured using a microplate reader.

The obtained results are shown in FIGS. 5a-5h (EGFR-expressing cells) and FIGS. 6a-6d (EGFR-non-expressing cells) As shown in FIGS. 5a-5h and 6a-6d, anti-EGFR/anti-4-1BB bispecific antibodies lead to strong activation of 4-1BB signal only when co-cultured with EGFR-expressing cells.

6.3. EGFR Quantitation

EGFR cell surface expression level was quantified on various cancer cell lines using QIFIKIT quantification kit (Dako) according to manufacturer's recommendation. Briefly, cells were stained with unlabeled anti-EGFR mouse monoclonal antibody (Abcam) or purified mouse IgG2b isotype control (Abcam) at saturating concentration. After washing, the stained cells and calibration beads from the kit were simultaneously labeled with the same FITC-conjugated goat anti-mouse IgG secondary antibody from the kit. Labeled cells and calibration beads were analyzed on a flow cytometer. A linear regression was performed using MFI values from the calibration beads. ABC (Antibody-Binding Capacity) was extrapolated from this regression line and sABC (specific ABC) was determined by subtracting ABC of the isotype control antibody from ABC of anti-EGFR antibody.

The obtained results are shown in Table 34.

TABLE 34

| Cell lines | | EGFR sABC |
|---|---|---|
| A-431 | ATCC, CRL-1555 | 682,147 |
| PANC-1 | ATCC, CRL-1469 | 197,813 |
| MDA-MB-231 | ATCC, HTB-26 | 134,628 |
| HCC1954 | ATCC, CRL-2338 | 48,486 |
| Calu-3 | ATCC, HTB-55 | 45,666 |
| DLD-1 | ATCC, CCL-221 | 20,509 |
| SK-BR-3 | ATCC, HTB-30 | 19,778 |
| NCI-N87 | ATCC, CRL-5822 | 9,968 |
| SW620 | ATCC, CCL-227 | 137 |
| CHO-K1 | ATCC, CCL-61 | 22 |
| JURKAT | ATCC, TIB-152 | 13 |
| MC38 | Kerafast, NH204 | 4 |

As shown in Table 34, the sABC of 9 cancer cell lines was determined.

6.4. Correlation Between the EGFR sABC and 4-1BB-Induced NF-kB Signaling

The EGFR levels measured in Example 6.3 were standardized to EGFR levels expressed by MDA-MB231. The levels of 4-1BB activation by the bispecific antibody were determined as maximum level of fold change compared with control in 4-1BB NF-kB luciferase reporter assay of Example 6.2. Shared area indicates confidence interval for a linear fit.

The obtained results are shown in FIGS. 7a-7c. As shown in FIGS. 7a-7c, 4-1BB activation by anti-EGFR/anti-4-1BB bispecific antibody showed a strong correlation with EGFR cell surface expression compared to BMUR (FIG. 7c).

Example 7. T Cell Immune Response 7.1. Effect on Release of Cytokine

To test the ability of bispecific antibodies to stimulated human peripheral blood mononuclear cells (PBMCs) response, the concentration of IFN-gamma in supernatant was measured. Human PBMCs stimulated with anti-human CD3 antibody (BioLegend, 5 ug/mL) were used as the effector cells. DLD-1 cells which expressed EGFR was used as the target cells. In this system, PBMCs were co-cultured with DLD-1 in the presence of human anti-CD3 antibody. Bispecific antibodies (Example 3, EGFR(WT)×1A10 M12, EGFR(NA)×1A10 M12) (starting from 20 nM (=4 ug/mL) diluted for 10 dose) and monospecific antibodies (Example 1 and 2, Anti-EGFR(WT), Anti-EGFR(NA), 1A10) (starting from 26.67 nM (=4 ug/mL) diluted for 10 dose) were added to the mixed culture. After culture in a humidified chamber with 5% CO₂ at 37° C. for 72 hours, the concentration of IFN-gamma in supernatant was measured by Human IFN-gamma Quantikine Kit (R&D system, SIF50).

The obtained results are shown in FIGS. 8a and 8b. As shown in FIGS. 8a and 8b, all the tested bispecific antibodies induced cytokine release more than the combination of each monoclonal antibody in presence of EGFR high expressing cells.

7.2. Effect on Target Cell Growth

To test the ability of bispecific antibodies to stimulated human PBMCs response, target cell lysis assay was used. Human PBMCs stimulated with human anti-CD3 antibody were used as the effector cells. DLD-1 cells which expressed EGFR was used as the target cells. In this system, PBMCs were co-cultured with DLD-1 in the presence of human anti-CD3 antibody (BioLegend, 5 ug/mL). Bispecific antibodies (Example 3, EGFR(WT)×1A10 M12, EGFR(NA)×1A10 M12, EGFR(WT)×1A12 M1, EGFR(NA)×1A12 M1) (starting from 20 nM (=4 ug/mL) diluted for 10 dose) and monospecific antibodies (Example 1 and 2, Anti-EGFR (WT), Anti-EGFR (NA), 1A10, 1A12) (starting from 26.67 nM (=4 ug/mL) diluted for 10 dose) were added to the mixed culture. After culture, the survival of DLD-1 was measured by cell counting kit-8 (Dojindo, CK04-20).

The obtained results are shown in FIGS. 9a-9d. As shown in FIGS. 9a-9d, all the tested bispecific antibodies showed superior cancer cell death activities compared to the combination of each monospecific antibody in presence of EGFR high expressing cells.

Example 8. In Vivo Anti-Tumor Efficacy in OLD-1 Bearing hPBMC Engrafted Mice To test in vivo anti-tumor efficacy of anti-EGFR/anti-4-1BB bispecific antibodies, PBMC-humanized NPG mice were used. 6-8 weeks NPG mice were intravenously injected with $1\times10^7$ human PBMC and $5\times10^6$ DLD-1 cancer cells were inoculated into right flank of the mice at 5 day after PBMC injection. DLD-1 bearing humanized mice were randomized to each test group (n=8/group) at day 6 post tumor implantation based on tumor volume and average tumor volume of each group was about 85 mm³. Human IgG1 control antibody, Cetuximab, urelumab and anti-EGFR/anti-4-1BB bispecific antibody ET(NA)×1A10 were intraperitoneally administered twice a week at doses of 10 or 60 mg/kg. During the experiment, the tumor size was measured with a digital caliper and the animals had been euthanized when tumor volume reached 3000 mm³ or body weight loss exceeded 20% from the initial treatment occurs.

The survival results are shown in FIG. 10. As shown in FIG. 10, Urelumab induced adverse effects including body weight loss as well as slight anti-tumor effect. While, the mice treated with ET(NA)×1A10 at dose of 60 mg/kg showed superior survival than the mice applied with other treatment.

Example 9. In Vivo Anti-Tumor Efficacy in 4-1BB Knock-In Mice 9.1. The Anti-Tumor Activity In vivo anti-tumor efficacy of anti-EGFR/anti-4-1BB bispecific antibodies have been evaluated in human EGFR/MC38 tumor bearing 4-1BB knock-in mice (Biocytogen). Human EGFR/MC38 cell line was generated by SIRION BIOTECH based on MC38-WT, and EGFR expression was confirmed by. $5\times10^5$ EGFR/MC38 cells were inoculated into right flank of mice. The mice were randomized to each test group (n=5/group) at day 8 post tumor inoculation based on tumor volume (approximately 80 mm³). Human IgG1 antibody, Cetuximab and anti-EGFR/anti-4-1BB bispecific antibodies (ET(WT)×1A10 M12, ET(NA)×1A10 M12) were intraperitoneally administered twice a week at dose of 10 mg/kg into the mice for 4 weeks. Tumor size was measured with a digital caliper.

The obtained results are shown in FIG. 11. As shown in FIG. 11, anti-EGFR/anti-4-1BB bispecific antibodies showed superior anti-tumor efficacy compared to Cetuximab in human EGFR/MC38 tumor. Most mice who were treated with ET(WT)×1A10 M12 and ET(NA)×1A10 M12 have been cured.

9.2. Evaluation on the Effect of Tumor Specific Memory T Cell

The mice cured by ET(WT)×1A10 M12 and ET(NA)×1A10 M12 were re-challenged with human EGFR/MC38 tumor cells (Biocytogen) and B16F10 tumor cells (ATCC) in both flanks at 100 days post tumor injection. Mice were not administered with any drug during re-challenge study period. Tumor size was measured with a digital caliper.

The obtained results are shown in FIG. 12. As shown in FIG. 12, human EGFR/MC38 tumor development was not observed. In addition, B16F10 tumor growth was suppressed by EGFR(WT)×1A10 M12 and EGFR(NA)×1A10 M12 treatment.

Example 10. Antibody-Dependent Cellular Cytotoxicity (ADCC) Activity (NA Backbone Vs. WT)

10.1. NK Cell-Mediated ADCC

In this example, human peripheral blood-derived CD56⁺ NK cells were used as effector cells and CellTrace Violet (Thermo Fisher Scientific)-labeled DLD-1 cells (ATCC) expressing EGFR were used as target cells. Cells were co-cultured at an effector:target ratio of 5:1 with 50 nM of anti-EGFR/anti-4-1BB bispecific antibodies (Example 3) at 37° C. After 4 hours, cells were stained with Fixable Viability Dye (eBioscience™) and then the ratio of dead target cells was analyzed by flow cytometry.

The obtained results are shown in following FIG. 13. As shown in FIG. 13, IgG1 type (WT) of anti-EGFR/anti-4-1BB bispecific antibodies showed a prominent ADCC effect mediated by NK cells.

10.2. 4-1BB Signal Activation Dependent on FcγRIIb Engagement

In this example, CHO-K1 cells expressing FcγRIIb (Promega) were plated in a 96-well assay plate and cultured overnight. On the day of assay, Jurkat/4-1BB cells (Promega) were plated in 96 well plate. Cells were incubated with a titration of anti-EGFR/anti-4-1BB bispecific antibodies in the presence (FcγRIIb dependent) or absence (FcγRIIb independent) of CHO-K1 cells expressing FcγRIIb (Promega). After 6 hours of induction, Bio-Glo™ Luciferase Assay reagent was added and luminescence was determined using a SpectraMax L luminometer (Molecular Devices). Four-parameter logistic curve analysis was performed with GraphPad Prism® software.

The obtained results are shown in following Tables 35 (FcγRIIb-dependent 4-1BB bioassay) and 36 (FcγRIIb-independent 4-1BB bioassay), and FIGS. 14a (FcγRIIb-dependent 4-1BB bioassay) and 14b (FcγRIIb-independent 4-1BB bioassay).

TABLE 35

| FcγRIIb-dependent 4-1BB bioassay | | |
|---|---|---|
| | Fold of induction (RLU) | EC$_{50}$ (nM) |
| Urelumab | 189.7 | 0.2395 |
| EGFR(WT)X1A10 M12 | <2 | Not applicable |
| EGFR(NA)X1A10 M12 | <2 | Not applicable |
| EGFR(WT)X1A12 M1 | <2 | Not applicable |
| EGFR(NA)X1A12 M1 | <2 | Not applicable |

TABLE 36

| | Fold of induction (RLU) | $EC_{50}$ (nM) |
|---|---|---|
| Urelumab | 14.11 | 0.5369 |
| EGFR(WT)X1A10 M12 | <2 | Not applicable |
| EGFR(NA)X1A10 M12 | <2 | Not applicable |
| EGFR(WT)X1A12 M1 | <2 | Not applicable |
| EGFR(NA)X1A12 M1 | <2 | Not applicable |

FcγRIIb-independent 4-1BB bioassay

As shown in Tables 35 and 36, and FIGS. 14a and 14b, Urelumab-treated group showed 14.2-fold difference in top RLU and 2.3-fold difference in $EC_{50}$ according to the presence of FcγRIIb CHO-K1 cells. Four anti-EGFR/anti-4-1BB bispecific antibodies showed very low RLU compared to Urelumab regardless of the presence or absence of FcγRIIb CHO-K1 cells. These data showed that all the tested anti-EGFR/anti-4-1BB bispecific antibodies have potential benefits compared to urelumab, which has severe toxicity in clinical studies (NCT00309023, NCT00612664, NCT014712210).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and "one or more" and similar referents in the context of describing the invention (especially in the context of the following claims) are to be construed to cover both the singular and the plural, unless otherwise indicated herein or clearly contradicted by context. The use of the term "at least one" (or "one or more") followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "comprising, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law.

Moreover, any combination of the above-described elements in all possible variations thereof is encompassed by the invention unless otherwise indicated herein or otherwise clearly contradicted by context.

What is claimed is:

1. An anti-4-1BB/anti-EGFR bispecific antibody comprising:
(a) a 4-1BB targeting moiety which is an anti-4-1BB scFv, and
(b) an EGFR targeting moiety which is a full-length form of an anti-EGFR antibody, and
wherein the anti-4-1BB scFv comprises:
(1) an H-CDR1 comprising the amino acid sequence of SEQ ID NO: 1, an H-CDR2 comprising the amino acid sequence of SEQ ID NO: 4, an H-CDR3 comprising the amino acid sequence of SEQ ID NO: 7, an L-CDR1 comprising the amino acid sequence of SEQ ID NO: 12, an L-CDR2 comprising the amino acid sequence of SEQ ID NO: 14, and an L-CDR3 comprising the amino acid sequence of SEQ ID NO: 16;
(2) an H-CDR1 comprising the amino acid sequence of SEQ ID NO: 1, an H-CDR2 comprising the amino acid sequence of SEQ ID NO: 4, an H-CDR3 comprising the amino acid sequence of SEQ ID NO: 8, an L-CDR1 comprising the amino acid sequence of SEQ ID NO: 12, an L-CDR2 comprising the amino acid sequence of SEQ ID NO: 14, and an L-CDR3 comprising the amino acid sequence of SEQ ID NO: 16; or
(3) an H-CDR1 comprising the amino acid sequence of SEQ ID NO: 1, an H-CDR2 comprising the amino acid sequence of SEQ ID NO: 4, an H-CDR3 comprising the amino acid sequence of SEQ ID NO: 9, an L-CDR1 comprising the amino acid sequence of SEQ ID NO: 12, an L-CDR2 comprising the amino acid sequence of SEQ ID NO: 14, and an L-CDR3 comprising the amino acid sequence of SEQ ID NO: 16, and
wherein the anti-EGFR antibody comprises:
a heavy chain comprising the amino acid sequence of SEQ ID NO: 73, or 74; and
a light chain comprising the amino acid sequence of SEQ ID NO: 75.

2. The anti-4-1BB/anti-EGFR bispecific antibody of claim 1, wherein
the anti-4-1BB antibody of claim 1(1) comprises
a heavy chain variable region comprising the amino acid sequence of SEQ ID NO: 18 and a light chain variable region comprising the amino acid sequence of SEQ ID NO: 30, or
a heavy chain variable region comprising the amino acid sequence of SEQ ID NO: 24 and a light chain variable region comprising the amino acid sequence of SEQ ID NO: 33;
the anti-4-1BB antibody of claim 1(2) comprises
a heavy chain variable region comprising the amino acid sequence of SEQ ID NO: 19 and a light chain variable region comprising the amino acid sequence of SEQ ID NO: 30 or 31, or
a heavy chain variable region comprising the amino acid sequence of SEQ ID NO: 25 and a light chain variable region comprising the amino acid sequence of SEQ ID NO: 33 or 34; or the anti-4-1BB antibody of claim 1(3) comprises
a heavy chain variable region comprising the amino acid sequence of SEQ ID NO: 20 and a light chain variable region comprising the amino acid sequence of SEQ ID NO: 30 or 31.

3. The anti-4-1BB/anti-EGFR bispecific antibody of claim 1, wherein the anti-4-1BB scFv comprises a peptide linker between the heavy chain variable region and the light chain variable region.

4. A pharmaceutical composition comprising the anti-4-1BB/anti-EGFR bispecific antibody of claim 1 and a pharmaceutically acceptable carrier.

5. The anti-4-1BB/anti-EGFR bispecific antibody of claim 1, wherein the anti-4-1BB/anti-EGFR bispecific antibody comprises:
a polypeptide comprising the amino acid sequence of SEQ ID NO: 76, 77, 78, 79, or 83; and
a polypeptide comprising the amino acid sequence of SEQ ID NO: 75.

6. The anti-4-1BB/anti-EGFR bispecific antibody of claim 1, wherein the anti-4-1BB/anti-EGFR bispecific antibody comprises:
a polypeptide comprising the amino acid sequence of SEQ ID NO: 79; and
a polypeptide comprising the amino acid sequence of SEQ ID NO: 75.

\* \* \* \* \*

SEQUENCE LISTING

```
<160> NUMBER OF SEQ ID NOS: 91

<210> SEQ ID NO 1
<211> LENGTH: 5
<212> TYPE: PRT
<213> ORGANISM: Artificial Sequence
<220> FEATURE:
<223> OTHER INFORMATION: Synthetic_H-CDR1 of anti-4-1BB antibody

<400> SEQUENCE: 1

Ser Tyr Asp Met Ser
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic_H-CDR1 of anti-4-1BB antibody

<400> SEQUENCE: 2

Gly Tyr Asp Met Ser
1               5

<210> SEQ ID NO 3
<211> LENGTH: 5
<212> TYPE: PRT
<213> ORGANISM: Artificial Sequence
```

```
<220> FEATURE:
<223> OTHER INFORMATION: Synthetic_H-CDR1 of anti-4-1BB antibody

<400> SEQUENCE: 3

Ser Tyr Trp Met His
1               5

<210> SEQ ID NO 4
<211> LENGTH: 17
<212> TYPE: PRT
<213> ORGANISM: Artificial Sequence
<220> FEATURE:
<223> OTHER INFORMATION: Synthetic_H-CDR2 of anti-4-1BB antibody

<400> SEQUENCE: 4

Trp Ile Ser Tyr Ser Gly Gly Ser Ile Tyr Tyr Ala Asp Ser Val Lys
1               5                   10                  15

Gly

<210> SEQ ID NO 5
<211> LENGTH: 17
<212> TYPE: PRT
<213> ORGANISM: Artificial Sequence
<220> FEATURE:
<223> OTHER INFORMATION: Synthetic_H-CDR2 of anti-4-1BB antibody

<400> SEQUENCE: 5

Val Ile Tyr Pro Asp Asp Gly Asn Thr Tyr Tyr Ala Asp Ser Val Lys
1               5                   10                  15

Gly

<210> SEQ ID NO 6
<211> LENGTH: 17
<212> TYPE: PRT
<213> ORGANISM: Artificial Sequence
<220> FEATURE:
<223> OTHER INFORMATION: Synthetic_H-CDR2 of anti-4-1BB antibody

<400> SEQUENCE: 6

Glu Ile Asn Pro Gly Asn Gly His Thr Asn Tyr Asn Glu Lys Phe Lys
1               5                   10                  15

Ser

<210> SEQ ID NO 7
<211> LENGTH: 12
<212> TYPE: PRT
<213> ORGANISM: Artificial Sequence
<220> FEATURE:
<223> OTHER INFORMATION: Synthetic_H-CDR3 of anti-4-1BB antibody

<400> SEQUENCE: 7

Asp Gly Gln Arg Asn Ser Met Arg Glu Phe Asp Tyr
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Synthetic_H-CDR3 of anti-4-1BB antibody

<400> SEQUENCE: 8

Asp Ala Gln Arg Asn Ser Met Arg Glu Phe Asp Tyr
1               5                   10
```

```
<210> SEQ ID NO 9
<211> LENGTH: 12
<212> TYPE: PRT
<213> ORGANISM: Artificial Sequence
<220> FEATURE:
<223> OTHER INFORMATION: Synthetic_H-CDR3 of anti-4-1BB antibody

<400> SEQUENCE: 9

Asp Ala Gln Arg Gln Ser Met Arg Glu Phe Asp Tyr
1               5                   10

<210> SEQ ID NO 10
<211> LENGTH: 18
<212> TYPE: PRT
<213> ORGANISM: Artificial Sequence
<220> FEATURE:
<223> OTHER INFORMATION: Synthetic_H-CDR3 of anti-4-1BB antibody

<400> SEQUENCE: 10

His Gly Gly Gln Lys Pro Thr Thr Lys Ser Ser Ser Ala Tyr Gly Met
1               5                   10                  15

Asp Gly

<210> SEQ ID NO 11
<211> LENGTH: 10
<212> TYPE: PRT
<213> ORGANISM: Artificial Sequence
<220> FEATURE:
<223> OTHER INFORMATION: Synthetic_H-CDR3 of anti-4-1BB antibody

<400> SEQUENCE: 11

Ser Phe Thr Thr Ala Arg Ala Phe Ala Tyr
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Synthetic_L-CDR1 of anti-4-1BB antibody

<400> SEQUENCE: 12

Ser Gly Ser Ser Ser Asn Ile Gly Asn Asn Tyr Val Thr
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Synthetic_L-CDR1 of anti-4-1BB antibody

<400> SEQUENCE: 13

Arg Ala Ser Gln Thr Ile Ser Asp Tyr Leu His
1               5                   10

<210> SEQ ID NO 14
<211> LENGTH: 7
<212> TYPE: PRT
<213> ORGANISM: Artificial Sequence
<220> FEATURE:
<223> OTHER INFORMATION: Synthetic_L-CDR2 of anti-4-1BB antibody

<400> SEQUENCE: 14

Ala Asp Ser His Arg Pro Ser
1               5
```

<210> SEQ ID NO 15
<211> LENGTH: 7
<212> TYPE: PRT
<213> ORGANISM: Artificial Sequence
<220> FEATURE:
<223> OTHER INFORMATION: Synthetic_L-CDR2 of anti-4-1BB antibody

<400> SEQUENCE: 15

Tyr Ala Ser Gln Ser Ile Ser
1               5

<210> SEQ ID NO 16
<211> LENGTH: 11
<212> TYPE: PRT
<213> ORGANISM: Artificial Sequence
<220> FEATURE:
<223> OTHER INFORMATION: Synthetic_L-CDR3 of anti-4-1BB antibody

<400> SEQUENCE: 16

Ala Thr Trp Asp Tyr Ser Leu Ser Gly Tyr Val
1               5                   10

<210> SEQ ID NO 17
<211> LENGTH: 9
<212> TYPE: PRT
<213> ORGANISM: Artificial Sequence
<220> FEATURE:
<223> OTHER INFORMATION: Synthetic_L-CDR3 of anti-4-1BB antibody

<400> SEQUENCE: 17

Gln Asp Gly His Ser Phe Pro Pro Thr
1               5

<210> SEQ ID NO 18
<211> LENGTH: 121
<212> TYPE: PRT
<213> ORGANISM: Artificial Sequence
<220> FEATURE:
<223> OTHER INFORMATION: Synthetic_heavy chain variable region of
      anti-4-1BB antibody (1A10)

<400> SEQUENCE: 18

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Trp Ile Ser Tyr Ser Gly Gly Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Gln Arg Asn Ser Met Arg Glu Phe Asp Tyr Trp Gly
            100                 105                 110

Gln Gly Thr Leu Val Thr Val Ser Ser
        115                 120

<210> SEQ ID NO 19
<211> LENGTH: 121
<212> TYPE: PRT

<213> ORGANISM: Artificial Sequence
<220> FEATURE:
<223> OTHER INFORMATION: Synthetic_heavy chain variable region of
    anti-4-1BB antibody (1A10 M4, 1A10 M12)

<400> SEQUENCE: 19

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Trp Ile Ser Tyr Ser Gly Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Gln Arg Asn Ser Met Arg Glu Phe Asp Tyr Trp Gly
            100                 105                 110

Gln Gly Thr Leu Val Thr Val Ser Ser
        115                 120

<210> SEQ ID NO 20
<211> LENGTH: 121
<212> TYPE: PRT
<213> ORGANISM: Artificial Sequence
<220> FEATURE:
<223> OTHER INFORMATION: Synthetic_heavy chain variable region of
    anti-4-1BB antibody (1A10 M11, 1A10 M13)

<400> SEQUENCE: 20

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Trp Ile Ser Tyr Ser Gly Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Gln Arg Gln Ser Met Arg Glu Phe Asp Tyr Trp Gly
            100                 105                 110

Gln Gly Thr Leu Val Thr Val Ser Ser
        115                 120

<210> SEQ ID NO 21
<211> LENGTH: 127
<212> TYPE: PRT
<213> ORGANISM: Artificial Sequence
<220> FEATURE:
<223> OTHER INFORMATION: Synthetic_heavy chain variable region of
    anti-4-1BB antibody (1A12)

<400> SEQUENCE: 21

Glu Val Gln Leu Leu Glu Ser Gly Gly Gly Leu Val Gln Pro Gly Gly
1               5                   10                  15

```
Ser Leu Arg Leu Ser Cys Ala Ala Ser Gly Phe Thr Phe Ser Gly Tyr
         20                  25                  30

Asp Met Ser Trp Val Arg Gln Ala Pro Gly Lys Gly Leu Glu Trp Val
             35                  40                  45

Ser Val Ile Tyr Pro Asp Asp Gly Asn Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Ala Ala Val Tyr Tyr Cys
                 85                  90                  95

Ala Lys His Gly Gly Gln Lys Pro Thr Thr Lys Ser Ser Ser Ala Tyr
                100                 105                 110

Gly Met Asp Gly Trp Gly Gln Gly Thr Leu Val Thr Val Ser Ser
            115                 120                 125

<210> SEQ ID NO 22
<211> LENGTH: 127
<212> TYPE: PRT
<213> ORGANISM: Artificial Sequence
<220> FEATURE:
<223> OTHER INFORMATION: Synthetic_heavy chain variable region of
      anti-4-1BB antibody (1A12M1)

<400> SEQUENCE: 22

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Gly Tyr
         20                  25                  30

Asp Met Ser Trp Val Arg Gln Ala Pro Gly Lys Gly Leu Glu Trp Val
             35                  40                  45

Ser Val Ile Tyr Pro Asp Asp Gly Asn Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys His Gly Gly Gln Lys Pro Thr Thr Lys Ser Ser Ser Ala Tyr
                100                 105                 110

Gly Met Asp Gly Trp Gly Gln Gly Thr Leu Val Thr Val Ser Ser
            115                 120                 125

<210> SEQ ID NO 23
<211> LENGTH: 119
<212> TYPE: PRT
<213> ORGANISM: Artificial Sequence
<220> FEATURE:
<223> OTHER INFORMATION: Synthetic_heavy chain variable region of
      anti-4-1BB antibody (AB41)

<400> SEQUENCE: 23

Gln Val Gln Leu Gln Gln Ser Gly Ala Glu Val Ile Lys Pro Gly Ala
 1               5                  10                  15

Ser Val Lys Leu Ser Cys Lys Ala Ser Gly Tyr Thr Phe Ser Ser Tyr
         20                  25                  30

Trp Met His Trp Val Arg Gln Ala Pro Gly Gln Gly Leu Glu Trp Ile
             35                  40                  45

Gly Glu Ile Asn Pro Gly Asn Gly His Thr Asn Tyr Asn Glu Lys Phe
 50                  55                  60
```

```
Lys Ser Arg Ala Thr Leu Thr Gly Asp Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Ser Phe Thr Thr Ala Arg Ala Phe Ala Tyr Trp Gly Gln Gly
            100                 105                 110

Thr Leu Val Thr Val Ser Ser
        115

<210> SEQ ID NO 24
<211> LENGTH: 121
<212> TYPE: PRT
<213> ORGANISM: Artificial Sequence
<220> FEATURE:
<223> OTHER INFORMATION: Synthetic_heavy chain variable region of
      anti-4-1BB antibody (mutated 1A10)

<400> SEQUENCE: 24

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Asp Met Ser Trp Val Arg Gln Ala Pro Gly Lys Cys Leu Glu Trp Val
         35                  40                  45

Ser Trp Ile Ser Tyr Ser Gly Gly Ser Ile Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Gly Gln Arg Asn Ser Met Arg Glu Phe Asp Tyr Trp Gly
            100                 105                 110

Gln Gly Thr Leu Val Thr Val Ser Ser
        115                 120

<210> SEQ ID NO 25
<211> LENGTH: 121
<212> TYPE: PRT
<213> ORGANISM: Artificial Sequence
<220> FEATURE:
<223> OTHER INFORMATION: Synthetic_heavy chain variable region of
      anti-4-1BB antibody (mutated 1A10 M4, 1A10 M12)

<400> SEQUENCE: 25

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Asp Met Ser Trp Val Arg Gln Ala Pro Gly Lys Cys Leu Glu Trp Val
         35                  40                  45

Ser Trp Ile Ser Tyr Ser Gly Gly Ser Ile Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Ala Gln Arg Asn Ser Met Arg Glu Phe Asp Tyr Trp Gly
            100                 105                 110
```

Gln Gly Thr Leu Val Thr Val Ser Ser
        115                 120

<210> SEQ ID NO 26
<211> LENGTH: 121
<212> TYPE: PRT
<213> ORGANISM: Artificial Sequence
<220> FEATURE:
<223> OTHER INFORMATION: Synthetic_heavy chain variable region of
      anti-4-1BB antibody (mutated 1A10 M11, 1A10 M13)

<400> SEQUENCE: 26

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Cys Leu Glu Trp Val
        35                  40                  45

Ser Trp Ile Ser Tyr Ser Gly Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Gln Arg Gln Ser Met Arg Glu Phe Asp Tyr Trp Gly
            100                 105                 110

Gln Gly Thr Leu Val Thr Val Ser Ser
        115                 120

<210> SEQ ID NO 27
<211> LENGTH: 127
<212> TYPE: PRT
<213> ORGANISM: Artificial Sequence
<220> FEATURE:
<223> OTHER INFORMATION: Synthetic_heavy chain variable region of
      anti-4-1BB antibody (mutated 1A12)

<400> SEQUENCE: 27

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Asp Met Ser Trp Val Arg Gln Ala Pro Gly Lys Cys Leu Glu Trp Val
        35                  40                  45

Ser Val Ile Tyr Pro Asp Asp Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Ala Ala Val Tyr Tyr Cys
                85                  90                  95

Ala Lys His Gly Gly Gln Lys Pro Thr Thr Lys Ser Ser Ala Tyr
            100                 105                 110

Gly Met Asp Gly Trp Gly Gln Gly Thr Leu Val Thr Val Ser Ser
        115                 120                 125

<210> SEQ ID NO 28
<211> LENGTH: 127
<212> TYPE: PRT
<213> ORGANISM: Artificial Sequence

```
<220> FEATURE:
<223> OTHER INFORMATION: Synthetic_heavy chain variable region of
      anti-4-1BB antibody (mutated 1A12M1)

<400> SEQUENCE: 28

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Asp Met Ser Trp Val Arg Gln Ala Pro Gly Lys Cys Leu Glu Trp Val
        35                  40                  45

Ser Val Ile Tyr Pro Asp Asp Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys His Gly Gly Gln Lys Pro Thr Thr Lys Ser Ser Ser Ala Tyr
            100                 105                 110

Gly Met Asp Gly Trp Gly Gln Gly Thr Leu Val Thr Val Ser Ser
        115                 120                 125

<210> SEQ ID NO 29
<211> LENGTH: 119
<212> TYPE: PRT
<213> ORGANISM: Artificial Sequence
<220> FEATURE:
<223> OTHER INFORMATION: Synthetic_heavy chain variable region of
      anti-4-1BB antibody (mutated AB41)

<400> SEQUENCE: 29

Gln Val Gln Leu Gln Gln Ser Gly Ala Glu Val Ile Lys Pro Gly Ala
1               5                   10                  15

Ser Val Lys Leu Ser Cys Lys Ala Ser Gly Tyr Thr Phe Ser Ser Tyr
            20                  25                  30

Trp Met His Trp Val Arg Gln Ala Pro Gly Gln Cys Leu Glu Trp Ile
        35                  40                  45

Gly Glu Ile Asn Pro Gly Asn Gly His Thr Asn Tyr Asn Glu Lys Phe
    50                  55                  60

Lys Ser Arg Ala Thr Leu Thr Gly Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Phe Thr Thr Ala Arg Ala Phe Ala Tyr Trp Gly Gln Gly
            100                 105                 110

Thr Leu Val Thr Val Ser Ser
        115

<210> SEQ ID NO 30
<211> LENGTH: 110
<212> TYPE: PRT
<213> ORGANISM: Artificial Sequence
<220> FEATURE:
<223> OTHER INFORMATION: Synthetic_light chain variable region of
      anti-4-1BB antibody (1A10, 1A10 M4, 1A10 M11, 1A12)

<400> SEQUENCE: 30

Gln Ser Val Leu Thr Gln Pro Pro Ser Ala Ser Gly Thr Pro Gly Arg
1               5                   10                  15
```

```
Arg Val Thr Ile Ser Cys Ser Gly Ser Ser Asn Ile Gly Asn Asn
            20                  25                  30

Tyr Val Thr Trp Tyr Gln Gln Leu Pro Gly Thr Ala Pro Lys Leu Leu
            35                  40                  45

Ile Tyr Ala Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Tyr Ser Leu
                85                  90                  95

Ser Gly Tyr Val Phe Gly Gly Gly Thr Lys Leu Thr Val Leu
            100                 105                 110

<210> SEQ ID NO 31
<211> LENGTH: 110
<212> TYPE: PRT
<213> ORGANISM: Artificial Sequence
<220> FEATURE:
<223> OTHER INFORMATION: Synthetic_light chain variable region of
      anti-4-1BB antibody (1A10 M12, 1A10 M13, 1A12M1)

<400> SEQUENCE: 31

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Asn Asn
            20                  25                  30

Tyr Val Thr Trp Tyr Gln Gln Leu Pro Gly Thr Ala Pro Lys Leu Leu
            35                  40                  45

Ile Tyr Ala Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Tyr Ser Leu
                85                  90                  95

Ser Gly Tyr Val Phe Gly Gly Gly Thr Lys Leu Thr Val Leu
            100                 105                 110

<210> SEQ ID NO 32
<211> LENGTH: 108
<212> TYPE: PRT
<213> ORGANISM: Artificial Sequence
<220> FEATURE:
<223> OTHER INFORMATION: Synthetic_light chain variable region of
      anti-4-1BB antibody (AB41)

<400> SEQUENCE: 32

Asp Ile Val Met Thr Gln Ser Pro Ala Phe Leu Ser Val Thr Pro Gly
1               5                   10                  15

Glu Lys Val Thr Ile Thr Cys Arg Ala Ser Gln Thr Ile Ser Asp Tyr
            20                  25                  30

Leu His Trp Tyr Gln Gln Lys Pro Asp Gln Ala Pro Lys Leu Leu Ile
            35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Asp Gly His Ser Phe Pro Pro
                85                  90                  95
```

Thr Phe Gly Gln Gly Thr Lys Leu Glu Ile Lys Arg
            100                 105

<210> SEQ ID NO 33
<211> LENGTH: 110
<212> TYPE: PRT
<213> ORGANISM: Artificial Sequence
<220> FEATURE:
<223> OTHER INFORMATION: Synthetic_light chain variable region of
      anti-4-1BB antibody (mutated 1A10, 1A10 M4, 1A10 M11, 1A12)

<400> SEQUENCE: 33

Gln Ser Val Leu Thr Gln Pro Pro Ser Ala Ser Gly Thr Pro Gly Arg
1               5                   10                  15

Arg Val Thr Ile Ser Cys Ser Gly Ser Ser Asn Ile Gly Asn Asn
            20                  25                  30

Tyr Val Thr Trp Tyr Gln Gln Leu Pro Gly Thr Ala Pro Lys Leu Leu
        35                  40                  45

Ile Tyr Ala Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Tyr Ser Leu
                85                  90                  95

Ser Gly Tyr Val Phe Gly Cys Gly Thr Lys Leu Thr Val Leu
            100                 105                 110

<210> SEQ ID NO 34
<211> LENGTH: 110
<212> TYPE: PRT
<213> ORGANISM: Artificial Sequence
<220> FEATURE:
<223> OTHER INFORMATION: Synthetic_light chain variable region of
      anti-4-1BB antibody (mutated 1A10 M12, 1A10 M13, 1A12M1)

<400> SEQUENCE: 34

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Asn Asn
            20                  25                  30

Tyr Val Thr Trp Tyr Gln Gln Leu Pro Gly Thr Ala Pro Lys Leu Leu
        35                  40                  45

Ile Tyr Ala Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Tyr Ser Leu
                85                  90                  95

Ser Gly Tyr Val Phe Gly Cys Gly Thr Lys Leu Thr Val Leu
            100                 105                 110

<210> SEQ ID NO 35
<211> LENGTH: 30
<212> TYPE: PRT
<213> ORGANISM: Artificial Sequence
<220> FEATURE:
<223> OTHER INFORMATION: Synthetic_H-FR1 of anti-4-1BB antibody

<400> SEQUENCE: 35

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 36
<211> LENGTH: 30
<212> TYPE: PRT
<213> ORGANISM: Artificial Sequence
<220> FEATURE:
<223> OTHER INFORMATION: Synthetic_H-FR1 of anti-4-1BB antibody

<400> SEQUENCE: 36

Gln Val Gln Leu Gln Gln Ser Gly Ala Glu Val Ile Lys Pro Gly Ala
1               5                   10                  15

Ser Val Lys Leu Ser Cys Lys Ala Ser Gly Tyr Thr Phe Ser
            20                  25                  30

<210> SEQ ID NO 37
<211> LENGTH: 14
<212> TYPE: PRT
<213> ORGANISM: Artificial Sequence
<220> FEATURE:
<223> OTHER INFORMATION: Synthetic_H-FR2 of anti-4-1BB antibody

<400> SEQUENCE: 37

Trp Val Arg Gln Ala Pro Gly Lys Gly Leu Glu Trp Val Ser
1               5                   10

<210> SEQ ID NO 38
<211> LENGTH: 14
<212> TYPE: PRT
<213> ORGANISM: Artificial Sequence
<220> FEATURE:
<223> OTHER INFORMATION: Synthetic_H-FR2 of anti-4-1BB antibody

<400> SEQUENCE: 38

Trp Val Arg Gln Ala Pro Gly Gln Gly Leu Glu Trp Ile Gly
1               5                   10

<210> SEQ ID NO 39
<211> LENGTH: 14
<212> TYPE: PRT
<213> ORGANISM: Artificial Sequence
<220> FEATURE:
<223> OTHER INFORMATION: Synthetic_H-FR2 of anti-4-1BB antibody

<400> SEQUENCE: 39

Trp Val Arg Gln Ala Pro Gly Lys Cys Leu Glu Trp Val Ser
1               5                   10

<210> SEQ ID NO 40
<211> LENGTH: 14
<212> TYPE: PRT
<213> ORGANISM: Artificial Sequence
<220> FEATURE:
<223> OTHER INFORMATION: Synthetic_H-FR2 of anti-4-1BB antibody

<400> SEQUENCE: 40

Trp Val Arg Gln Ala Pro Gly Gln Cys Leu Glu Trp Ile Gly
1               5                   10

<210> SEQ ID NO 41
<211> LENGTH: 32
<212> TYPE: PRT
<213> ORGANISM: Artificial Sequence
<220> FEATURE:
<223> OTHER INFORMATION: Synthetic_H-FR3 of anti-4-1BB antibody

<400> SEQUENCE: 41

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 42
<211> LENGTH: 32
<212> TYPE: PRT
<213> ORGANISM: Artificial Sequence
<220> FEATURE:
<223> OTHER INFORMATION: Synthetic_H-FR3 of anti-4-1BB antibody

<400> SEQUENCE: 42

Arg Phe Thr Ile Ser Arg Asp Asn Ser Lys Asn Thr Leu Tyr Leu Gln
1               5                   10                  15

Met Asn Ser Leu Arg Ala Glu Asp Ala Ala Val Tyr Tyr Cys Ala Lys
            20                  25                  30

<210> SEQ ID NO 43
<211> LENGTH: 32
<212> TYPE: PRT
<213> ORGANISM: Artificial Sequence
<220> FEATURE:
<223> OTHER INFORMATION: Synthetic_H-FR3 of anti-4-1BB antibody

<400> SEQUENCE: 43

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Lys
            20                  25                  30

<210> SEQ ID NO 44
<211> LENGTH: 32
<212> TYPE: PRT
<213> ORGANISM: Artificial Sequence
<220> FEATURE:
<223> OTHER INFORMATION: Synthetic_H-FR3 of anti-4-1BB antibody

<400> SEQUENCE: 44

Arg Ala Thr Leu Thr Gly Asp Thr Ser Thr Ser Thr Val Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 45
<211> LENGTH: 11
<212> TYPE: PRT
<213> ORGANISM: Artificial Sequence
<220> FEATURE:
<223> OTHER INFORMATION: Synthetic_H-FR4 of anti-4-1BB antibody

<400> SEQUENCE: 45

Trp Gly Gln Gly Thr Leu Val Thr Val Ser Ser
1               5                   10

<210> SEQ ID NO 46
<211> LENGTH: 22
<212> TYPE: PRT
<213> ORGANISM: Artificial Sequence
<220> FEATURE:
<223> OTHER INFORMATION: Synthetic_L-FR1 of anti-4-1BB antibody

<400> SEQUENCE: 46

```
Gln Ser Val Leu Thr Gln Pro Pro Ser Ala Ser Gly Thr Pro Gly Arg
1               5                   10                  15

Arg Val Thr Ile Ser Cys
            20

<210> SEQ ID NO 47
<211> LENGTH: 22
<212> TYPE: PRT
<213> ORGANISM: Artificial Sequence
<220> FEATURE:
<223> OTHER INFORMATION: Synthetic_L-FR1 of anti-4-1BB antibody

<400> SEQUENCE: 47

Gln Ser Val Leu Thr Gln Pro Pro Ser Ala Ser Gly Thr Pro Gly Gln
1               5                   10                  15

Arg Val Thr Ile Ser Cys
            20

<210> SEQ ID NO 48
<211> LENGTH: 23
<212> TYPE: PRT
<213> ORGANISM: Artificial Sequence
<220> FEATURE:
<223> OTHER INFORMATION: Synthetic_L-FR1 of anti-4-1BB antibody

<400> SEQUENCE: 48

Asp Ile Val Met Thr Gln Ser Pro Ala Phe Leu Ser Val Thr Pro Gly
1               5                   10                  15

Glu Lys Val Thr Ile Thr Cys
            20

<210> SEQ ID NO 49
<211> LENGTH: 15
<212> TYPE: PRT
<213> ORGANISM: Artificial Sequence
<220> FEATURE:
<223> OTHER INFORMATION: Synthetic_L-FR2 of anti-4-1BB antibody

<400> SEQUENCE: 49

Trp Tyr Gln Gln Leu Pro Gly Thr Ala Pro Lys Leu Leu Ile Tyr
1               5                   10                  15

<210> SEQ ID NO 50
<211> LENGTH: 15
<212> TYPE: PRT
<213> ORGANISM: Artificial Sequence
<220> FEATURE:
<223> OTHER INFORMATION: Synthetic_L-FR2 of anti-4-1BB antibody

<400> SEQUENCE: 50

Trp Tyr Gln Gln Lys Pro Asp Gln Ala Pro Lys Leu Leu Ile Lys
1               5                   10                  15

<210> SEQ ID NO 51
<211> LENGTH: 32
<212> TYPE: PRT
<213> ORGANISM: Artificial Sequence
<220> FEATURE:
<223> OTHER INFORMATION: Synthetic_L-FR3 of anti-4-1BB antibody

<400> SEQUENCE: 51

Gly Val Pro Asp Arg Phe Ser Gly Ser Lys Ser Gly Thr Ser Ala Ser
1               5                   10                  15

Leu Ala Ile Ser Gly Leu Arg Ser Glu Asp Glu Ala Asp Tyr Tyr Cys
```

<210> SEQ ID NO 52
<211> LENGTH: 32
<212> TYPE: PRT
<213> ORGANISM: Artificial Sequence
<220> FEATURE:
<223> OTHER INFORMATION: Synthetic_L-FR3 of anti-4-1BB antibody

<400> SEQUENCE: 52

Gly Ile Pro Ser Arg Phe Ser Gly Ser Gly Ser Gly Thr Asp Phe Thr
1               5                   10                  15

Phe Thr Ile Ser Ser Leu Glu Ala Glu Asp Ala Ala Thr Tyr Tyr Cys
            20                  25                  30

<210> SEQ ID NO 53
<211> LENGTH: 10
<212> TYPE: PRT
<213> ORGANISM: Artificial Sequence
<220> FEATURE:
<223> OTHER INFORMATION: Synthetic_L-FR4 of anti-4-1BB antibody

<400> SEQUENCE: 53

Phe Gly Gly Gly Thr Lys Leu Thr Val Leu
1               5                   10

<210> SEQ ID NO 54
<211> LENGTH: 11
<212> TYPE: PRT
<213> ORGANISM: Artificial Sequence
<220> FEATURE:
<223> OTHER INFORMATION: Synthetic_L-FR4 of anti-4-1BB antibody

<400> SEQUENCE: 54

Phe Gly Gln Gly Thr Lys Leu Glu Ile Lys Arg
1               5                   10

<210> SEQ ID NO 55
<211> LENGTH: 10
<212> TYPE: PRT
<213> ORGANISM: Artificial Sequence
<220> FEATURE:
<223> OTHER INFORMATION: Synthetic_L-FR4 of anti-4-1BB antibody

<400> SEQUENCE: 55

Phe Gly Cys Gly Thr Lys Leu Thr Val Leu
1               5                   10

<210> SEQ ID NO 56
<211> LENGTH: 448
<212> TYPE: PRT
<213> ORGANISM: Artificial Sequence
<220> FEATURE:
<223> OTHER INFORMATION: Synthetic_heavy chain of anti-4-1BB antibody

<400> SEQUENCE: 56

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Trp Ile Ser Tyr Ser Gly Gly Ser Ile Tyr Tyr Ala Asp Ser Val
    50                  55                  60

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Gly Gln Arg Asn Ser Met Arg Glu Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

<210> SEQ ID NO 57
<211> LENGTH: 448
<212> TYPE: PRT
<213> ORGANISM: Artificial Sequence
<220> FEATURE:
<223> OTHER INFORMATION: Synthetic_heavy chain of anti-4-1BB antibody
```

<400> SEQUENCE: 57

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Trp Ile Ser Tyr Ser Gly Gly Ser Ile Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Gln Arg Asn Ser Met Arg Glu Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
```

```
                    405                 410                 415
Arg Trp Gln Glu Gly Asn Val Phe Ser Cys Ser Val Met His Glu Ala
                420                 425                 430

Leu His Asn His Tyr Thr Gln Lys Ser Leu Ser Leu Ser Leu Gly Lys
            435                 440                 445

<210> SEQ ID NO 58
<211> LENGTH: 448
<212> TYPE: PRT
<213> ORGANISM: Artificial Sequence
<220> FEATURE:
<223> OTHER INFORMATION: Synthetic_heavy chain of anti-4-1BB antibody

<400> SEQUENCE: 58

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Trp Ile Ser Tyr Ser Gly Gly Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Gln Arg Gln Ser Met Arg Glu Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
```

```
                   325                 330                 335
Ile Ser Lys Ala Lys Gly Gln Pro Arg Glu Pro Gln Val Tyr Thr Leu
                340                 345                 350

Pro Pro Ser Gln Glu Glu Met Thr Lys Asn Gln Val Ser Leu Thr Cys
                355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
                420                 425                 430

Leu His Asn His Tyr Thr Gln Lys Ser Leu Ser Leu Ser Leu Gly Lys
            435                 440                 445

<210> SEQ ID NO 59
<211> LENGTH: 454
<212> TYPE: PRT
<213> ORGANISM: Artificial Sequence
<220> FEATURE:
<223> OTHER INFORMATION: Synthetic_heavy chain of anti-4-1BB antibody

<400> SEQUENCE: 59

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
                20                  25                  30

Asp Met Ser Trp Val Arg Gln Ala Pro Gly Lys Gly Leu Glu Trp Val
            35                  40                  45

Ser Val Ile Tyr Pro Asp Asp Gly Asn Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Ala Ala Val Tyr Tyr Cys
                85                  90                  95

Ala Lys His Gly Gly Gln Lys Pro Thr Thr Lys Ser Ser Ala Tyr
                100                 105                 110

Gly Met Asp Gly Trp Gly Gln Gly Thr Leu Val Thr Val Ser Ser Ala
            115                 120                 125

Ser Thr Lys Gly Pro Ser Val Phe Pro Leu Ala Pro Cys Ser Arg Ser
        130                 135                 140

Thr Ser Glu Ser Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Lys Thr Tyr
        195                 200                 205

Thr Cys Asn Val Asp His Lys Pro Ser Asn Thr Lys Val Asp Lys Arg
    210                 215                 220

Val Glu Ser Lys Tyr Gly Pro Pro Cys Pro Pro Cys Pro Ala Pro Glu
225                 230                 235                 240

Phe Leu Gly Gly Pro Ser Val Phe Leu Phe Pro Pro Lys Pro Lys Asp
```

```
                   245                 250                 255
Thr Leu Met Ile Ser Arg Thr Pro Glu Val Thr Cys Val Val Asp
                260                 265                 270

Val Ser Gln Glu Asp Pro Glu Val Gln Phe Asn Trp Tyr Val Asp Gly
            275                 280                 285

Val Glu Val His Asn Ala Lys Thr Lys Pro Arg Glu Glu Gln Phe Asn
            290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Gly Leu Pro
                325                 330                 335

Ser Ser Ile Glu Lys Thr Ile Ser Lys Ala Lys Gly Gln Pro Arg Glu
                340                 345                 350

Pro Gln Val Tyr Thr Leu Pro Pro Ser Gln Glu Glu Met Thr Lys Asn
            355                 360                 365

Gln Val Ser Leu Thr Cys Leu Val Lys Gly Phe Tyr Pro Ser Asp Ile
            370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Arg
                405                 410                 415

Leu Thr Val Asp Lys Ser Arg Trp Gln Glu Gly Asn Val Phe Ser Cys
                420                 425                 430

Ser Val Met His Glu Ala Leu His Asn His Tyr Thr Gln Lys Ser Leu
            435                 440                 445

Ser Leu Ser Leu Gly Lys
        450

<210> SEQ ID NO 60
<211> LENGTH: 454
<212> TYPE: PRT
<213> ORGANISM: Artificial Sequence
<220> FEATURE:
<223> OTHER INFORMATION: Synthetic_heavy chain of anti-4-1BB antibody

<400> SEQUENCE: 60

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Asp Met Ser Trp Val Arg Gln Ala Pro Gly Lys Gly Leu Glu Trp Val
        35                  40                  45

Ser Val Ile Tyr Pro Asp Asp Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys His Gly Gly Gln Lys Pro Thr Thr Lys Ser Ser Ser Ala Tyr
            100                 105                 110

Gly Met Asp Gly Trp Gly Gln Gly Thr Leu Val Thr Val Ser Ser Ala
        115                 120                 125

Ser Thr Lys Gly Pro Ser Val Phe Pro Leu Ala Pro Cys Ser Arg Ser
    130                 135                 140

Thr Ser Glu Ser Thr Ala Ala Leu Gly Cys Leu Val Lys Asp Tyr Phe
```

```
                145                 150                 155                 160
        Pro Glu Pro Val Thr Val Ser Trp Asn Ser Gly Ala Leu Thr Ser Gly
                        165                 170                 175

Val His Thr Phe Pro Ala Val Leu Gln Ser Ser Gly Leu Tyr Ser Leu
                        180                 185                 190

Ser Ser Val Val Thr Val Pro Ser Ser Ser Leu Gly Thr Lys Thr Tyr
                        195                 200                 205

Thr Cys Asn Val Asp His Lys Pro Ser Asn Thr Lys Val Asp Lys Arg
                210                 215                 220

Val Glu Ser Lys Tyr Gly Pro Pro Cys Pro Pro Cys Pro Ala Pro Glu
        225                 230                 235                 240

Phe Leu Gly Gly Pro Ser Val Phe Leu Phe Pro Pro Lys Pro Lys Asp
                        245                 250                 255

Thr Leu Met Ile Ser Arg Thr Pro Glu Val Thr Cys Val Val Val Asp
                        260                 265                 270

Val Ser Gln Glu Asp Pro Glu Val Gln Phe Asn Trp Tyr Val Asp Gly
                        275                 280                 285

Val Glu Val His Asn Ala Lys Thr Lys Pro Arg Glu Glu Gln Phe Asn
                290                 295                 300

Ser Thr Tyr Arg Val Val Ser Val Leu Thr Val Leu His Gln Asp Trp
        305                 310                 315                 320

Leu Asn Gly Lys Glu Tyr Lys Cys Lys Val Ser Asn Lys Gly Leu Pro
                        325                 330                 335

Ser Ser Ile Glu Lys Thr Ile Ser Lys Ala Lys Gly Gln Pro Arg Glu
                        340                 345                 350

Pro Gln Val Tyr Thr Leu Pro Pro Ser Gln Glu Glu Met Thr Lys Asn
                        355                 360                 365

Gln Val Ser Leu Thr Cys Leu Val Lys Gly Phe Tyr Pro Ser Asp Ile
                370                 375                 380

Ala Val Glu Trp Glu Ser Asn Gly Gln Pro Glu Asn Asn Tyr Lys Thr
        385                 390                 395                 400

Thr Pro Pro Val Leu Asp Ser Asp Gly Ser Phe Phe Leu Tyr Ser Arg
                        405                 410                 415

Leu Thr Val Asp Lys Ser Arg Trp Gln Glu Gly Asn Val Phe Ser Cys
                        420                 425                 430

Ser Val Met His Glu Ala Leu His Asn His Tyr Thr Gln Lys Ser Leu
                435                 440                 445

Ser Leu Ser Leu Gly Lys
            450

<210> SEQ ID NO 61
<211> LENGTH: 446
<212> TYPE: PRT
<213> ORGANISM: Artificial Sequence
<220> FEATURE:
<223> OTHER INFORMATION: Synthetic_heavy chain of anti-4-1BB antibody

<400> SEQUENCE: 61

Gln Val Gln Leu Gln Gln Ser Gly Ala Glu Val Ile Lys Pro Gly Ala
        1               5                   10                  15

Ser Val Lys Leu Ser Cys Lys Ala Ser Gly Tyr Thr Phe Ser Ser Tyr
                        20                  25                  30

Trp Met His Trp Val Arg Gln Ala Pro Gly Gln Gly Leu Glu Trp Ile
                        35                  40                  45

Gly Glu Ile Asn Pro Gly Asn Gly His Thr Asn Tyr Asn Glu Lys Phe
```

```
            50                  55                  60
Lys Ser Arg Ala Thr Leu Thr Gly Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Ser Phe Thr Thr Ala Arg Ala Phe Ala Tyr Trp Gly Gln Gly
                100                 105                 110

Thr Leu Val Thr Val Ser Ser Ala Ser Thr Lys Gly Pro Ser Val Phe
                115                 120                 125

Pro Leu Ala Pro Cys Ser Arg Ser Thr Ser Glu Ser Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Lys Thr Tyr Thr Cys Asn Val Asp His Lys Pro
                195                 200                 205

Ser Asn Thr Lys Val Asp Lys Arg Val Glu Ser Lys Tyr Gly Pro Pro
210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
                260                 265                 270

Gln Phe Asn Trp Tyr Val Asp Gly Val Glu Val His Asn Ala Lys Thr
                275                 280                 285

Lys Pro Arg Glu Glu Gln Phe Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Gln Glu Glu Met Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
                370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
                420                 425                 430

Asn His Tyr Thr Gln Lys Ser Leu Ser Leu Ser Leu Gly Lys
                435                 440                 445

<210> SEQ ID NO 62
<211> LENGTH: 216
<212> TYPE: PRT
<213> ORGANISM: Artificial Sequence
```

<220> FEATURE:
<223> OTHER INFORMATION: Synthetic_light chain of anti-4-1BB antibody

<400> SEQUENCE: 62

Gln Ser Val Leu Thr Gln Pro Pro Ser Ala Ser Gly Thr Pro Gly Arg
1               5                   10                  15

Arg Val Thr Ile Ser Cys Ser Gly Ser Ser Asn Ile Gly Asn Asn
            20                  25                  30

Tyr Val Thr Trp Tyr Gln Gln Leu Pro Gly Thr Ala Pro Lys Leu Leu
        35                  40                  45

Ile Tyr Ala Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Tyr Ser Leu
                85                  90                  95

Ser Gly Tyr Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Ala Glu Cys Ser
    210                 215

<210> SEQ ID NO 63
<211> LENGTH: 216
<212> TYPE: PRT
<213> ORGANISM: Artificial Sequence
<220> FEATURE:
<223> OTHER INFORMATION: Synthetic_light chain of anti-4-1BB antibody

<400> SEQUENCE: 63

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Asn Asn
            20                  25                  30

Tyr Val Thr Trp Tyr Gln Gln Leu Pro Gly Thr Ala Pro Lys Leu Leu
        35                  40                  45

Ile Tyr Ala Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Tyr Ser Leu
                85                  90                  95

Ser Gly Tyr Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu

```
            115                 120                 125
Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
                180                 185                 190

Arg Ser Tyr Ser Cys Gln Val Thr His Glu Gly Ser Thr Val Glu Lys
                195                 200                 205

Thr Val Ala Pro Ala Glu Cys Ser
    210                 215

<210> SEQ ID NO 64
<211> LENGTH: 214
<212> TYPE: PRT
<213> ORGANISM: Artificial Sequence
<220> FEATURE:
<223> OTHER INFORMATION: Synthetic_light chain of anti-4-1BB antibody

<400> SEQUENCE: 64

Asp Ile Val Met Thr Gln Ser Pro Ala Phe Leu Ser Val Thr Pro Gly
1               5                   10                  15

Glu Lys Val Thr Ile Thr Cys Arg Ala Ser Gln Thr Ile Ser Asp Tyr
                20                  25                  30

Leu His Trp Tyr Gln Gln Lys Pro Asp Gln Ala Pro Lys Leu Leu Ile
            35                  40                  45

Lys Tyr Ala Ser Gln Ser Ile Ser Gly Ile Pro Ser Arg Phe Ser Gly
50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Asp Gly His Ser Phe Pro Pro
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210

<210> SEQ ID NO 65
<211> LENGTH: 5
<212> TYPE: PRT
<213> ORGANISM: Artificial Sequence
<220> FEATURE:
<223> OTHER INFORMATION: Synthetic_H-CDR1 of anti-EGFR antibody
```

<400> SEQUENCE: 65

Asn Tyr Gly Val His
1               5

<210> SEQ ID NO 66
<211> LENGTH: 16
<212> TYPE: PRT
<213> ORGANISM: Artificial Sequence
<220> FEATURE:
<223> OTHER INFORMATION: Synthetic_H-CDR2 of anti-EGFR antibody

<400> SEQUENCE: 66

Val Ile Trp Ser Gly Gly Asn Thr Asp Tyr Asn Thr Pro Phe Thr Ser
1               5                   10                  15

<210> SEQ ID NO 67
<211> LENGTH: 11
<212> TYPE: PRT
<213> ORGANISM: Artificial Sequence
<220> FEATURE:
<223> OTHER INFORMATION: Synthetic_H-CDR3 of anti-EGFR antibody

<400> SEQUENCE: 67

Ala Leu Thr Tyr Tyr Asp Tyr Glu Phe Ala Tyr
1               5                   10

<210> SEQ ID NO 68
<211> LENGTH: 11
<212> TYPE: PRT
<213> ORGANISM: Artificial Sequence
<220> FEATURE:
<223> OTHER INFORMATION: Synthetic_L-CDR1 of anti-EGFR antibody

<400> SEQUENCE: 68

Arg Ala Ser Gln Ser Ile Gly Thr Asn Ile His
1               5                   10

<210> SEQ ID NO 69
<211> LENGTH: 7
<212> TYPE: PRT
<213> ORGANISM: Artificial Sequence
<220> FEATURE:
<223> OTHER INFORMATION: Synthetic_L-CDR2 of anti-EGFR antibody

<400> SEQUENCE: 69

Tyr Ala Ser Glu Ser Ile Ser
1               5

<210> SEQ ID NO 70
<211> LENGTH: 9
<212> TYPE: PRT
<213> ORGANISM: Artificial Sequence
<220> FEATURE:
<223> OTHER INFORMATION: Synthetic_L-CDR3 of anti-EGFR antibody

<400> SEQUENCE: 70

Gln Gln Asn Asn Asn Trp Pro Thr Thr
1               5

<210> SEQ ID NO 71
<211> LENGTH: 118
<212> TYPE: PRT
<213> ORGANISM: Artificial Sequence
<220> FEATURE:
<223> OTHER INFORMATION: Synthetic_heavy chain variable region of
      anti-EGFR antibody

<400> SEQUENCE: 71

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser
        115

<210> SEQ ID NO 72
<211> LENGTH: 108
<212> TYPE: PRT
<213> ORGANISM: Artificial Sequence
<220> FEATURE:
<223> OTHER INFORMATION: Synthetic_light chain variable region of
      anti-EGFR antibody

<400> SEQUENCE: 72

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg
            100                 105

<210> SEQ ID NO 73
<211> LENGTH: 449
<212> TYPE: PRT
<213> ORGANISM: Artificial Sequence
<220> FEATURE:
<223> OTHER INFORMATION: Synthetic_heavy chain of anti-EGFR antibody
      (Cetuximab WT)

<400> SEQUENCE: 73

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

-continued

```
Gly Val Ile Trp Ser Gly Gly Asn Thr Asp Tyr Asn Thr Pro Phe Thr
 50                  55                  60

Ser Arg Leu Ser Ile Asn Lys Asp Asn Ser Lys Ser Gln Val Phe Phe
 65                  70                  75                  80

Lys Met Asn Ser Leu Gln Ser Asn Asp Thr Ala Ile Tyr Tyr Cys Ala
                 85                  90                  95

Arg Ala Leu Thr Tyr Tyr Asp Tyr Glu Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

<210> SEQ ID NO 74

```
<211> LENGTH: 449
<212> TYPE: PRT
<213> ORGANISM: Artificial Sequence
<220> FEATURE:
<223> OTHER INFORMATION: Synthetic_heavy chain of anti-EGFR antibody
      (N297A)

<400> SEQUENCE: 74

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Ala Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
```

```
                    370                 375                 380
Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys

<210> SEQ ID NO 75
<211> LENGTH: 214
<212> TYPE: PRT
<213> ORGANISM: Artificial Sequence
<220> FEATURE:
<223> OTHER INFORMATION: Synthetic_light chain of anti-EGFR antibody

<400> SEQUENCE: 75

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
                20                  25                  30

Ile His Trp Tyr Gln Gln Arg Thr Asn Gly Ser Pro Arg Leu Leu Ile
            35                  40                  45

Lys Tyr Ala Ser Glu Ser Ile Ser Gly Ile Pro Ser Arg Phe Ser Gly
50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 76
<211> LENGTH: 715
<212> TYPE: PRT
<213> ORGANISM: Artificial Sequence
<220> FEATURE:
<223> OTHER INFORMATION: Synthetic_heavy chain of bispecific antibody

<400> SEQUENCE: 76

Gln Val Gln Leu Lys Gln Ser Gly Pro Gly Leu Val Gln Pro Ser Gln
```

-continued

```
1               5                   10                  15
Ser Leu Ser Ile Thr Cys Thr Val Ser Gly Phe Ser Leu Thr Asn Tyr
                20                  25                  30
Gly Val His Trp Val Arg Gln Ser Pro Gly Lys Gly Leu Glu Trp Leu
                35                  40                  45
Gly Val Ile Trp Ser Gly Gly Asn Thr Asp Tyr Asn Thr Pro Phe Thr
                50                  55                  60
Ser Arg Leu Ser Ile Asn Lys Asp Asn Ser Lys Ser Gln Val Phe Phe
65                  70                  75                  80
Lys Met Asn Ser Leu Gln Ser Asn Asp Thr Ala Ile Tyr Tyr Cys Ala
                85                  90                  95
Arg Ala Leu Thr Tyr Tyr Asp Tyr Glu Phe Ala Tyr Trp Gly Gln Gly
                100                 105                 110
Thr Leu Val Thr Val Ser Ser Ala Ser Thr Lys Gly Pro Ser Val Phe
                115                 120                 125
Pro Leu Ala Pro Ser Ser Lys Ser Thr Ser Gly Gly Thr Ala Ala Leu
                130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
                180                 185                 190
Ser Ser Leu Gly Thr Gln Thr Tyr Ile Cys Asn Val Asn His Lys Pro
                195                 200                 205
Ser Asn Thr Lys Val Asp Lys Lys Val Glu Pro Lys Ser Cys Asp Lys
210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
                260                 265                 270
Pro Glu Val Lys Phe Asn Trp Tyr Val Asp Gly Val Glu Val His Asn
                275                 280                 285
Ala Lys Thr Lys Pro Arg Glu Glu Gln Tyr Ala Ser Thr Tyr Arg Val
                290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
                340                 345                 350
Leu Pro Pro Ser Arg Glu Glu Met Thr Lys Asn Gln Val Ser Leu Thr
                355                 360                 365
Cys Leu Val Lys Gly Phe Tyr Pro Ser Asp Ile Ala Val Glu Trp Glu
                370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
                420                 425                 430
```

```
Ala Leu His Asn His Tyr Thr Gln Lys Ser Leu Ser Leu Ser Pro Gly
            435                 440                 445

Lys Gly Gly Gly Ser Gly Gly Gly Ser Gly Gly Gly Ser
450                 455                 460

Gln Ser Val Leu Thr Gln Pro Pro Ser Ala Ser Gly Thr Pro Gly Arg
465                 470                 475                 480

Arg Val Thr Ile Ser Cys Ser Gly Ser Ser Asn Ile Gly Asn Asn
            485                 490                 495

Tyr Val Thr Trp Tyr Gln Gln Leu Pro Gly Thr Ala Pro Lys Leu Leu
            500                 505                 510

Ile Tyr Ala Asp Ser His Arg Pro Ser Gly Val Pro Asp Arg Phe Ser
            515                 520                 525

Gly Ser Lys Ser Gly Thr Ser Ala Ser Leu Ala Ile Ser Gly Leu Arg
            530                 535                 540

Ser Glu Asp Glu Ala Asp Tyr Tyr Cys Ala Thr Trp Asp Tyr Ser Leu
545                 550                 555                 560

Ser Gly Tyr Val Phe Gly Cys Gly Thr Lys Leu Thr Val Leu Gly Gly
            565                 570                 575

Gly Gly Ser Gly Gly Gly Ser Gly Gly Gly Ser Gly Gly Gly
            580                 585                 590

Gly Ser Glu Val Gln Leu Leu Glu Ser Gly Gly Leu Val Gln Pro
            595                 600                 605

Gly Gly Ser Leu Arg Leu Ser Cys Ala Ala Ser Gly Phe Thr Phe Ser
            610                 615                 620

Ser Tyr Asp Met Ser Trp Val Arg Gln Ala Pro Gly Lys Cys Leu Glu
625                 630                 635                 640

Trp Val Ser Trp Ile Ser Tyr Ser Gly Gly Ser Ile Tyr Tyr Ala Asp
            645                 650                 655

Ser Val Lys Gly Arg Phe Thr Ile Ser Arg Asp Asn Ser Lys Asn Thr
            660                 665                 670

Leu Tyr Leu Gln Met Asn Ser Leu Arg Ala Glu Asp Thr Ala Val Tyr
            675                 680                 685

Tyr Cys Ala Arg Asp Gly Gln Arg Asn Ser Met Arg Glu Phe Asp Tyr
            690                 695                 700

Trp Gly Gln Gly Thr Leu Val Thr Val Ser Ser
705                 710                 715

<210> SEQ ID NO 77
<211> LENGTH: 718
<212> TYPE: PRT
<213> ORGANISM: Artificial Sequence
<220> FEATURE:
<223> OTHER INFORMATION: Synthetic_heavy chain of bispecific antibody

<400> SEQUENCE: 77

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80
```

-continued

```
Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Ala Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys Gly Ser Gly Ser Gly Ser Gly Ser Gly Ser Gly Ser Gly Ser Gly
    450                 455                 460

Ser Gly Ser Gln Ser Val Leu Thr Gln Pro Pro Ser Ala Ser Gly Thr
465                 470                 475                 480

Pro Gly Arg Arg Val Thr Ile Ser Cys Ser Gly Ser Ser Ser Asn Ile
                485                 490                 495
```

```
Gly Asn Asn Tyr Val Thr Trp Tyr Gln Gln Leu Pro Gly Thr Ala Pro
                500                 505                 510

Lys Leu Leu Ile Tyr Ala Asp Ser His Arg Pro Ser Gly Val Pro Asp
            515                 520                 525

Arg Phe Ser Gly Ser Lys Ser Gly Thr Ser Ala Ser Leu Ala Ile Ser
        530                 535                 540

Gly Leu Arg Ser Glu Asp Glu Ala Asp Tyr Tyr Cys Ala Thr Trp Asp
545                 550                 555                 560

Tyr Ser Leu Ser Gly Tyr Val Phe Gly Cys Gly Thr Lys Leu Thr Val
                565                 570                 575

Leu Gly Gly Gly Gly Ser Gly Gly Gly Ser Gly Gly Gly Gly Ser
            580                 585                 590

Gly Gly Gly Gly Ser Glu Val Gln Leu Leu Glu Ser Gly Gly Gly Leu
            595                 600                 605

Val Gln Pro Gly Gly Ser Leu Arg Leu Ser Cys Ala Ala Ser Gly Phe
            610                 615                 620

Thr Phe Ser Ser Tyr Asp Met Ser Trp Val Arg Gln Ala Pro Gly Lys
625                 630                 635                 640

Cys Leu Glu Trp Val Ser Trp Ile Ser Tyr Ser Gly Gly Ser Ile Tyr
                645                 650                 655

Tyr Ala Asp Ser Val Lys Gly Arg Phe Thr Ile Ser Arg Asp Asn Ser
                660                 665                 670

Lys Asn Thr Leu Tyr Leu Gln Met Asn Ser Leu Arg Ala Glu Asp Thr
            675                 680                 685

Ala Val Tyr Tyr Cys Ala Arg Asp Gly Gln Arg Asn Ser Met Arg Glu
            690                 695                 700

Phe Asp Tyr Trp Gly Gln Gly Thr Leu Val Thr Val Ser Ser
705                 710                 715

<210> SEQ ID NO 78
<211> LENGTH: 718
<212> TYPE: PRT
<213> ORGANISM: Artificial Sequence
<220> FEATURE:
<223> OTHER INFORMATION: Synthetic_heavy chain of bispecific antibody

<400> SEQUENCE: 78

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140
```

-continued

```
Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Val Glu Pro Lys Ser Cys Asp Lys
                210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Ala Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
                355                 360                 365

Cys Leu Val Lys Gly Phe Tyr Pro Ser Asp Ile Ala Val Glu Trp Glu
                370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys Gly Ser Gly Ser Gly Ser Gly Ser Gly Ser Gly Ser Gly Ser Gly
                450                 455                 460

Ser Gly Ser Gln Ser Val Leu Thr Gln Pro Pro Ser Ala Ser Gly Thr
465                 470                 475                 480

Pro Gly Arg Arg Val Thr Ile Ser Cys Ser Gly Ser Ser Ser Asn Ile
                485                 490                 495

Gly Asn Asn Tyr Val Thr Trp Tyr Gln Gln Leu Pro Gly Thr Ala Pro
                500                 505                 510

Lys Leu Leu Ile Tyr Ala Asp Ser His Arg Pro Ser Gly Val Pro Asp
                515                 520                 525

Arg Phe Ser Gly Ser Lys Ser Gly Thr Ser Ala Ser Leu Ala Ile Ser
                530                 535                 540

Gly Leu Arg Ser Glu Asp Glu Ala Asp Tyr Tyr Cys Ala Thr Trp Asp
545                 550                 555                 560

Tyr Ser Leu Ser Gly Tyr Val Phe Gly Cys Gly Thr Lys Leu Thr Val
```

```
                        565                 570                 575
Leu Gly Gly Gly Gly Ser Gly Gly Gly Ser Gly Gly Gly Ser
                580                 585                 590
Gly Gly Gly Gly Ser Glu Val Gln Leu Leu Glu Ser Gly Gly Gly Leu
                595                 600                 605
Val Gln Pro Gly Gly Ser Leu Arg Leu Ser Cys Ala Ala Ser Gly Phe
        610                 615                 620
Thr Phe Ser Ser Tyr Asp Met Ser Trp Val Arg Gln Ala Pro Gly Lys
625                 630                 635                 640
Cys Leu Glu Trp Val Ser Trp Ile Ser Tyr Ser Gly Gly Ser Ile Tyr
                645                 650                 655
Tyr Ala Asp Ser Val Lys Gly Arg Phe Thr Ile Ser Arg Asp Asn Ser
                660                 665                 670
Lys Asn Thr Leu Tyr Leu Gln Met Asn Ser Leu Arg Ala Glu Asp Thr
                675                 680                 685
Ala Val Tyr Tyr Cys Ala Arg Asp Ala Gln Arg Asn Ser Met Arg Glu
        690                 695                 700
Phe Asp Tyr Trp Gly Gln Gly Thr Leu Val Thr Val Ser Ser
705                 710                 715
```

<210> SEQ ID NO 79
<211> LENGTH: 718
<212> TYPE: PRT
<213> ORGANISM: Artificial Sequence
<220> FEATURE:
<223> OTHER INFORMATION: Synthetic_heavy chain of bispecific antibody

<400> SEQUENCE: 79

```
Gln Val Gln Leu Lys Gln Ser Gly Pro Gly Leu Val Gln Pro Ser Gln
1               5                   10                  15
Ser Leu Ser Ile Thr Cys Thr Val Ser Gly Phe Ser Leu Thr Asn Tyr
                20                  25                  30
Gly Val His Trp Val Arg Gln Ser Pro Gly Lys Gly Leu Glu Trp Leu
            35                  40                  45
Gly Val Ile Trp Ser Gly Gly Asn Thr Asp Tyr Asn Thr Pro Phe Thr
        50                  55                  60
Ser Arg Leu Ser Ile Asn Lys Asp Asn Ser Lys Ser Gln Val Phe Phe
65                  70                  75                  80
Lys Met Asn Ser Leu Gln Ser Asn Asp Thr Ala Ile Tyr Tyr Cys Ala
                85                  90                  95
Arg Ala Leu Thr Tyr Tyr Asp Tyr Glu Phe Ala Tyr Trp Gly Gln Gly
            100                 105                 110
Thr Leu Val Thr Val Ser Ser Ala Ser Thr Lys Gly Pro Ser Val Phe
        115                 120                 125
Pro Leu Ala Pro Ser Ser Lys Ser Thr Ser Gly Gly Thr Ala Ala Leu
    130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Lys Val Glu Pro Lys Ser Cys Asp Lys
```

-continued

```
            210                 215                 220
Thr His Thr Cys Pro Pro Cys Pro Ala Pro Glu Leu Gly Gly Pro
225                 230                 235                 240

Ser Val Phe Leu Phe Pro Pro Lys Pro Lys Asp Thr Leu Met Ile Ser
                    245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Ala Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                    325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                    405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Lys Gly Ser Gly Ser Gly Ser Gly Ser Gly Ser Gly Ser Gly Ser Gly
450                 455                 460

Ser Gly Ser Gln Ser Val Leu Thr Gln Pro Pro Ser Ala Ser Gly Thr
465                 470                 475                 480

Pro Gly Gln Arg Val Thr Ile Ser Cys Ser Gly Ser Ser Ser Asn Ile
                    485                 490                 495

Gly Asn Asn Tyr Val Thr Trp Tyr Gln Gln Leu Pro Gly Thr Ala Pro
                500                 505                 510

Lys Leu Leu Ile Tyr Ala Asp Ser His Arg Pro Ser Gly Val Pro Asp
            515                 520                 525

Arg Phe Ser Gly Ser Lys Ser Gly Thr Ser Ala Ser Leu Ala Ile Ser
530                 535                 540

Gly Leu Arg Ser Glu Asp Glu Ala Asp Tyr Tyr Cys Ala Thr Trp Asp
545                 550                 555                 560

Tyr Ser Leu Ser Gly Tyr Val Phe Gly Cys Gly Thr Lys Leu Thr Val
                    565                 570                 575

Leu Gly Gly Gly Gly Ser Gly Gly Gly Gly Ser Gly Gly Gly Gly Ser
                580                 585                 590

Gly Gly Gly Gly Ser Glu Val Gln Leu Leu Glu Ser Gly Gly Gly Leu
            595                 600                 605

Val Gln Pro Gly Gly Ser Leu Arg Leu Ser Cys Ala Ala Ser Gly Phe
610                 615                 620

Thr Phe Ser Ser Tyr Asp Met Ser Trp Val Arg Gln Ala Pro Gly Lys
625                 630                 635                 640
```

```
Cys Leu Glu Trp Val Ser Trp Ile Ser Tyr Ser Gly Ser Ile Tyr
            645                 650                 655

Tyr Ala Asp Ser Val Lys Gly Arg Phe Thr Ile Ser Arg Asp Asn Ser
        660                 665                 670

Lys Asn Thr Leu Tyr Leu Gln Met Asn Ser Leu Arg Ala Glu Asp Thr
    675                 680                 685

Ala Val Tyr Tyr Cys Ala Arg Asp Ala Gln Arg Asn Ser Met Arg Glu
690                 695                 700

Phe Asp Tyr Trp Gly Gln Gly Thr Leu Val Thr Val Ser Ser
705                 710                 715

<210> SEQ ID NO 80
<211> LENGTH: 721
<212> TYPE: PRT
<213> ORGANISM: Artificial Sequence
<220> FEATURE:
<223> OTHER INFORMATION: Synthetic_heavy chain of bispecific antibody

<400> SEQUENCE: 80

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285
```

```
Ala Lys Thr Lys Pro Arg Glu Glu Gln Tyr Ala Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys Gly Gly Gly Gly Ser Gly Gly Gly Ser Gly Gly Gly Gly Ser
    450                 455                 460

Gln Ser Val Leu Thr Gln Pro Pro Ser Ala Ser Gly Thr Pro Gly Arg
465                 470                 475                 480

Arg Val Thr Ile Ser Cys Ser Gly Ser Ser Ser Asn Ile Gly Asn Asn
                485                 490                 495

Tyr Val Thr Trp Tyr Gln Gln Leu Pro Gly Thr Ala Pro Lys Leu Leu
            500                 505                 510

Ile Tyr Ala Asp Ser His Arg Pro Ser Gly Val Pro Asp Arg Phe Ser
        515                 520                 525

Gly Ser Lys Ser Gly Thr Ser Ala Ser Leu Ala Ile Ser Gly Leu Arg
    530                 535                 540

Ser Glu Asp Glu Ala Asp Tyr Tyr Cys Ala Thr Trp Asp Tyr Ser Leu
545                 550                 555                 560

Ser Gly Tyr Val Phe Gly Cys Gly Thr Lys Leu Thr Val Leu Gly Gly
                565                 570                 575

Gly Gly Ser Gly Gly Gly Gly Ser Gly Gly Gly Gly Ser Gly Gly Gly
            580                 585                 590

Gly Ser Glu Val Gln Leu Leu Glu Ser Gly Gly Gly Leu Val Gln Pro
        595                 600                 605

Gly Gly Ser Leu Arg Leu Ser Cys Ala Ala Ser Gly Phe Thr Phe Ser
    610                 615                 620

Gly Tyr Asp Met Ser Trp Val Arg Gln Ala Pro Gly Lys Cys Leu Glu
625                 630                 635                 640

Trp Val Ser Val Ile Tyr Pro Asp Asp Gly Asn Thr Tyr Tyr Ala Asp
                645                 650                 655

Ser Val Lys Gly Arg Phe Thr Ile Ser Arg Asp Asn Ser Lys Asn Thr
            660                 665                 670

Leu Tyr Leu Gln Met Asn Ser Leu Arg Ala Glu Asp Ala Ala Val Tyr
        675                 680                 685

Tyr Cys Ala Lys His Gly Gly Gln Lys Pro Thr Thr Lys Ser Ser Ser
    690                 695                 700
```

```
Ala Tyr Gly Met Asp Gly Trp Gly Gln Gly Thr Leu Val Thr Val Ser
705                 710                 715                 720

Ser
```

```
<210> SEQ ID NO 81
<211> LENGTH: 724
<212> TYPE: PRT
<213> ORGANISM: Artificial Sequence
<220> FEATURE:
<223> OTHER INFORMATION: Synthetic heavy chain of bispecific antibody

<400> SEQUENCE: 81

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
                20                  25                  30

Gly Val His Trp Val Arg Gln Ser Pro Gly Lys Gly Leu Glu Trp Leu
            35                  40                  45

Gly Val Ile Trp Ser Gly Gly Asn Thr Asp Tyr Asn Thr Pro Phe Thr
        50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Ala Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
```

```
                    340                 345                 350
Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys Gly Ser Gly Ser Gly Ser Gly Ser Gly Ser Gly Ser Gly Ser Gly
450                 455                 460

Ser Gly Ser Gln Ser Val Leu Thr Gln Pro Pro Ser Ala Ser Gly Thr
465                 470                 475                 480

Pro Gly Arg Arg Val Thr Ile Ser Cys Ser Gly Ser Ser Ser Asn Ile
                485                 490                 495

Gly Asn Asn Tyr Val Thr Trp Tyr Gln Gln Leu Pro Gly Thr Ala Pro
            500                 505                 510

Lys Leu Leu Ile Tyr Ala Asp Ser His Arg Pro Ser Gly Val Pro Asp
        515                 520                 525

Arg Phe Ser Gly Ser Lys Ser Gly Thr Ser Ala Ser Leu Ala Ile Ser
530                 535                 540

Gly Leu Arg Ser Glu Asp Glu Ala Asp Tyr Tyr Cys Ala Thr Trp Asp
545                 550                 555                 560

Tyr Ser Leu Ser Gly Tyr Val Phe Gly Cys Gly Thr Lys Leu Thr Val
                565                 570                 575

Leu Gly Gly Gly Gly Ser Gly Gly Gly Ser Gly Gly Gly Gly Ser
            580                 585                 590

Gly Gly Gly Gly Ser Glu Val Gln Leu Leu Glu Ser Gly Gly Gly Leu
        595                 600                 605

Val Gln Pro Gly Gly Ser Leu Arg Leu Ser Cys Ala Ala Ser Gly Phe
        610                 615                 620

Thr Phe Ser Gly Tyr Asp Met Ser Trp Val Arg Gln Ala Pro Gly Lys
625                 630                 635                 640

Cys Leu Glu Trp Val Ser Val Ile Tyr Pro Asp Asp Gly Asn Thr Tyr
                645                 650                 655

Tyr Ala Asp Ser Val Lys Gly Arg Phe Thr Ile Ser Arg Asp Asn Ser
            660                 665                 670

Lys Asn Thr Leu Tyr Leu Gln Met Asn Ser Leu Arg Ala Glu Asp Ala
        675                 680                 685

Ala Val Tyr Tyr Cys Ala Lys His Gly Gly Gln Lys Pro Thr Thr Lys
        690                 695                 700

Ser Ser Ser Ala Tyr Gly Met Asp Gly Trp Gly Gln Gly Thr Leu Val
705                 710                 715                 720

Thr Val Ser Ser

<210> SEQ ID NO 82
<211> LENGTH: 724
<212> TYPE: PRT
<213> ORGANISM: Artificial Sequence
<220> FEATURE:
```

<223> OTHER INFORMATION: Synthetic_heavy chain of bispecific antibody

<400> SEQUENCE: 82

```
Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Ala Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400
```

-continued

```
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
        435                 440                 445
Lys Gly Ser Gly Ser Gly Ser Gly Ser Gly Ser Gly Ser Gly Ser Gly
    450                 455                 460
Ser Gly Ser Gln Ser Val Leu Thr Gln Pro Pro Ser Ala Ser Gly Thr
465                 470                 475                 480
Pro Gly Gln Arg Val Thr Ile Ser Cys Ser Gly Ser Ser Ser Asn Ile
                485                 490                 495
Gly Asn Asn Tyr Val Thr Trp Tyr Gln Gln Leu Pro Gly Thr Ala Pro
            500                 505                 510
Lys Leu Leu Ile Tyr Ala Asp Ser His Arg Pro Ser Gly Val Pro Asp
        515                 520                 525
Arg Phe Ser Gly Ser Lys Ser Gly Thr Ser Ala Ser Leu Ala Ile Ser
    530                 535                 540
Gly Leu Arg Ser Glu Asp Glu Ala Asp Tyr Tyr Cys Ala Thr Trp Asp
545                 550                 555                 560
Tyr Ser Leu Ser Gly Tyr Val Phe Gly Cys Gly Thr Lys Leu Thr Val
                565                 570                 575
Leu Gly Gly Gly Gly Ser Gly Gly Gly Gly Ser Gly Gly Gly Gly Ser
            580                 585                 590
Gly Gly Gly Gly Ser Glu Val Gln Leu Leu Glu Ser Gly Gly Gly Leu
        595                 600                 605
Val Gln Pro Gly Gly Ser Leu Arg Leu Ser Cys Ala Ala Ser Gly Phe
    610                 615                 620
Thr Phe Ser Gly Tyr Asp Met Ser Trp Val Arg Gln Ala Pro Gly Lys
625                 630                 635                 640
Cys Leu Glu Trp Val Ser Val Ile Tyr Pro Asp Gly Asn Thr Tyr
                645                 650                 655
Tyr Ala Asp Ser Val Lys Gly Arg Phe Thr Ile Ser Arg Asp Asn Ser
            660                 665                 670
Lys Asn Thr Leu Tyr Leu Gln Met Asn Ser Leu Arg Ala Glu Asp Thr
        675                 680                 685
Ala Val Tyr Tyr Cys Ala Lys His Gly Gly Gln Lys Pro Thr Thr Lys
    690                 695                 700
Ser Ser Ser Ala Tyr Gly Met Asp Gly Trp Gln Gly Thr Leu Val
705                 710                 715                 720
Thr Val Ser Ser

<210> SEQ ID NO 83
<211> LENGTH: 718
<212> TYPE: PRT
<213> ORGANISM: Artificial Sequence
<220> FEATURE:
<223> OTHER INFORMATION: Synthetic_heavy chain of bispecific antibody

<400> SEQUENCE: 83

Gln Val Gln Leu Lys Gln Ser Gly Pro Gly Leu Val Gln Pro Ser Gln
1               5                   10                  15
Ser Leu Ser Ile Thr Cys Thr Val Ser Gly Phe Ser Leu Thr Asn Tyr
            20                  25                  30
Gly Val His Trp Val Arg Gln Ser Pro Gly Lys Gly Leu Glu Trp Leu
```

```
                    35                  40                  45
Gly Val Ile Trp Ser Gly Gly Asn Thr Asp Tyr Asn Thr Pro Phe Thr
 50                  55                  60

Ser Arg Leu Ser Ile Asn Lys Asp Asn Ser Lys Ser Gln Val Phe Phe
 65                  70                  75                  80

Lys Met Asn Ser Leu Gln Ser Asn Asp Thr Ala Ile Tyr Tyr Cys Ala
                 85                  90                  95

Arg Ala Leu Thr Tyr Tyr Asp Tyr Glu Phe Ala Tyr Trp Gly Gln Gly
                100                 105                 110

Thr Leu Val Thr Val Ser Ala Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys Gly Ser Gly Ser Gly Ser Gly Ser Gly Ser Gly Ser Gly Ser Gly
    450                 455                 460
```

Ser Gly Ser Gln Ser Val Leu Thr Gln Pro Pro Ser Ala Ser Gly Thr
465                 470                 475                 480

Pro Gly Gln Arg Val Thr Ile Ser Cys Ser Gly Ser Ser Asn Ile
            485                 490                 495

Gly Asn Asn Tyr Val Thr Trp Tyr Gln Gln Leu Pro Gly Thr Ala Pro
                500                 505                 510

Lys Leu Leu Ile Tyr Ala Asp Ser His Arg Pro Ser Gly Val Pro Asp
            515                 520                 525

Arg Phe Ser Gly Ser Lys Ser Gly Thr Ser Ala Ser Leu Ala Ile Ser
            530                 535                 540

Gly Leu Arg Ser Glu Asp Glu Ala Asp Tyr Tyr Cys Ala Thr Trp Asp
545                 550                 555                 560

Tyr Ser Leu Ser Gly Tyr Val Phe Gly Cys Gly Thr Lys Leu Thr Val
                565                 570                 575

Leu Gly Gly Gly Ser Gly Gly Gly Ser Gly Gly Gly Gly Ser
                580                 585                 590

Gly Gly Gly Gly Ser Glu Val Gln Leu Leu Glu Ser Gly Gly Gly Leu
            595                 600                 605

Val Gln Pro Gly Gly Ser Leu Arg Leu Ser Cys Ala Ala Ser Gly Phe
            610                 615                 620

Thr Phe Ser Ser Tyr Asp Met Ser Trp Val Arg Gln Ala Pro Gly Lys
625                 630                 635                 640

Cys Leu Glu Trp Val Ser Trp Ile Ser Tyr Ser Gly Ser Ile Tyr
                645                 650                 655

Tyr Ala Asp Ser Val Lys Gly Arg Phe Thr Ile Ser Arg Asp Asn Ser
                660                 665                 670

Lys Asn Thr Leu Tyr Leu Gln Met Asn Ser Leu Arg Ala Glu Asp Thr
            675                 680                 685

Ala Val Tyr Tyr Cys Ala Arg Asp Ala Gln Arg Asn Ser Met Arg Glu
690                 695                 700

Phe Asp Tyr Trp Gly Gln Gly Thr Leu Val Thr Val Ser Ser
705                 710                 715

<210> SEQ ID NO 84
<211> LENGTH: 724
<212> TYPE: PRT
<213> ORGANISM: Artificial Sequence
<220> FEATURE:
<223> OTHER INFORMATION: Synthetic_heavy chain of bispecific antibody

<400> SEQUENCE: 84

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

```
Thr Leu Val Thr Val Ser Ala Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys Gly Ser Gly Ser Gly Ser Gly Ser Gly Ser Gly Ser Gly Ser Gly
    450                 455                 460

Ser Gly Ser Gln Ser Val Leu Thr Gln Pro Pro Ser Ala Ser Gly Thr
465                 470                 475                 480

Pro Gly Gln Arg Val Thr Ile Ser Cys Ser Gly Ser Ser Ser Asn Ile
                485                 490                 495

Gly Asn Asn Tyr Val Thr Trp Tyr Gln Gln Leu Pro Gly Thr Ala Pro
            500                 505                 510

Lys Leu Leu Ile Tyr Ala Asp Ser His Arg Pro Ser Gly Val Pro Asp
        515                 520                 525
```

```
Arg Phe Ser Gly Ser Lys Ser Gly Thr Ser Ala Ser Leu Ala Ile Ser
            530                 535                 540

Gly Leu Arg Ser Glu Asp Glu Ala Asp Tyr Tyr Cys Ala Thr Trp Asp
545                 550                 555                 560

Tyr Ser Leu Ser Gly Tyr Val Phe Gly Cys Gly Thr Lys Leu Thr Val
                565                 570                 575

Leu Gly Gly Gly Gly Ser Gly Gly Gly Gly Ser Gly Gly Gly Gly Ser
            580                 585                 590

Gly Gly Gly Gly Ser Glu Val Gln Leu Leu Glu Ser Gly Gly Gly Leu
            595                 600                 605

Val Gln Pro Gly Gly Ser Leu Arg Leu Ser Cys Ala Ala Ser Gly Phe
610                 615                 620

Thr Phe Ser Gly Tyr Asp Met Ser Trp Val Arg Gln Ala Pro Gly Lys
625                 630                 635                 640

Cys Leu Glu Trp Val Ser Val Ile Tyr Pro Asp Gly Asn Thr Tyr
                645                 650                 655

Tyr Ala Asp Ser Val Lys Gly Arg Phe Thr Ile Ser Arg Asp Asn Ser
            660                 665                 670

Lys Asn Thr Leu Tyr Leu Gln Met Asn Ser Leu Arg Ala Glu Asp Thr
            675                 680                 685

Ala Val Tyr Tyr Cys Ala Lys His Gly Gly Gln Lys Pro Thr Thr Lys
690                 695                 700

Ser Ser Ser Ala Tyr Gly Met Asp Gly Trp Gly Gln Gly Thr Leu Val
705                 710                 715                 720

Thr Val Ser Ser

<210> SEQ ID NO 85
<211> LENGTH: 15
<212> TYPE: PRT
<213> ORGANISM: Artificial Sequence
<220> FEATURE:
<223> OTHER INFORMATION: Synthetic_peptide linker

<400> SEQUENCE: 85

Gly Gly Gly Gly Ser Gly Gly Gly Gly Ser Gly Gly Gly Gly Ser
1               5                   10                  15

<210> SEQ ID NO 86
<211> LENGTH: 18
<212> TYPE: PRT
<213> ORGANISM: Artificial Sequence
<220> FEATURE:
<223> OTHER INFORMATION: Synthetic_peptide linker

<400> SEQUENCE: 86

Gly Ser Gly Ser Gly Ser Gly Ser Gly Ser Gly Ser Gly Ser Gly Ser
1               5                   10                  15

Gly Ser

<210> SEQ ID NO 87
<211> LENGTH: 20
<212> TYPE: PRT
<213> ORGANISM: Artificial Sequence
<220> FEATURE:
<223> OTHER INFORMATION: Synthetic_peptide linker

<400> SEQUENCE: 87

Gly Gly Gly Gly Ser Gly Gly Gly Gly Ser Gly Gly Gly Gly Ser Gly
1               5                   10                  15
```

Gly Gly Gly Ser
        20

<210> SEQ ID NO 88
<211> LENGTH: 108
<212> TYPE: PRT
<213> ORGANISM: Artificial Sequence
<220> FEATURE:
<223> OTHER INFORMATION: Synthetic_light chain variable region of
      anti-4-1BB antibody (mutated AB41)

<400> SEQUENCE: 88

Asp Ile Val Met Thr Gln Ser Pro Ala Phe Leu Ser Val Thr Pro Gly
1               5                   10                  15

Glu Lys Val Thr Ile Thr Cys Arg Ala Ser Gln Thr Ile Ser Asp Tyr
            20                  25                  30

Leu His Trp Tyr Gln Gln Lys Pro Asp Gln Ala Pro Lys Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Asp Gly His Ser Phe Pro Pro
                85                  90                  95

Thr Phe Gly Cys Gly Thr Lys Leu Glu Ile Lys Arg
            100                 105

<210> SEQ ID NO 89
<211> LENGTH: 255
<212> TYPE: PRT
<213> ORGANISM: Artificial Sequence
<220> FEATURE:
<223> OTHER INFORMATION: Synthetic_human 4-1BB (NP_001552.2)

<400> SEQUENCE: 89

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
        35                  40                  45

Pro Pro Asn Ser Phe Ser Ser Ala Gly Gly Gln Arg Thr Cys Asp Ile
    50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
    130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu

```
                180              185              190
Ala Leu Thr Ser Thr Ala Leu Leu Phe Leu Leu Phe Phe Leu Thr Leu
                    195              200              205

Arg Phe Ser Val Val Lys Arg Gly Arg Lys Lys Leu Leu Tyr Ile Phe
    210              215              220

Lys Gln Pro Phe Met Arg Pro Val Gln Thr Thr Gln Glu Glu Asp Gly
225              230              235              240

Cys Ser Cys Arg Phe Pro Glu Glu Glu Glu Gly Gly Cys Glu Leu
                    245              250              255

<210> SEQ ID NO 90
<211> LENGTH: 449
<212> TYPE: PRT
<213> ORGANISM: Artificial Sequence
<220> FEATURE:
<223> OTHER INFORMATION: Synthetic_heavy chain of anti-EGFR antibody
      (Cetuximab)

<400> SEQUENCE: 90

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285
```

```
Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
        435                 440                 445

Lys

<210> SEQ ID NO 91
<211> LENGTH: 10
<212> TYPE: PRT
<213> ORGANISM: Artificial Sequence
<220> FEATURE:
<223> OTHER INFORMATION: Synthetic_peptide linker

<400> SEQUENCE: 91

Gly Gly Gly Gly Ser Gly Gly Gly Gly Ser
1               5                   10
```